US010017829B2

(12) United States Patent
Fabrizius et al.

(10) Patent No.: US 10,017,829 B2
(45) Date of Patent: Jul. 10, 2018

(54) GENETIC LOCI ASSOCIATED WITH FROGEYE LEAF SPOT RESISTANCE AND BROWN STEM ROT RESISTANCE AND METHODS OF USE

(71) Applicant: PIONEER HI-BRED INTERNATIONAL, INC., Johnston, IA (US)

(72) Inventors: Martin A. Fabrizius, Willmar, MN (US); Feng Han, Hockessin, DE (US); Donald Kyle, Princeton, IL (US); Joshua M. Shendelman, Ankeny, IA (US); Jordan D. Spear, Algona, IA (US); Paul A. Stephens, Urbandale, IA (US); Yun Xia, Canfield, OH (US)

(73) Assignee: PIONEER HI-BRED INTERNATIONAL, INC. IA (US)

( * ) Notice: Subject to any disclaimer, the term of this patent is extended or adjusted under 35 U.S.C. 154(b) by 82 days.

(21) Appl. No.: 14/776,282

(22) PCT Filed: Mar. 10, 2014

(86) PCT No.: PCT/US2014/022631
§ 371 (c)(1),
(2) Date: Sep. 14, 2015

(87) PCT Pub. No.: WO2014/150226
PCT Pub. Date: Sep. 25, 2014

(65) Prior Publication Data

US 2016/0032409 A1 Feb. 4, 2016

Related U.S. Application Data

(60) Provisional application No. 61/787,515, filed on Mar. 15, 2013.

(51) Int. Cl.

| | |
|---|---|
| ***C12N 15/82*** | (2006.01) |
| ***C12Q 1/68*** | (2018.01) |
| ***A01H 5/10*** | (2018.01) |
| ***C12Q 1/6895*** | (2018.01) |
| ***A01H 1/04*** | (2006.01) |

(52) U.S. Cl.
CPC ............ *C12Q 1/6895* (2013.01); *A01H 1/04* (2013.01); *C12Q 2600/13* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | | |
|---|---|---|---|---|
| 5,689,035 | A | 11/1997 | Webb | |
| 5,948,953 | A | 9/1999 | Webb | |
| 7,642,403 | B2 | 1/2010 | Godwin et al. | |
| 7,919,675 | B2 * | 4/2011 | Godwin .................. | A01H 1/04 435/6.13 |
| 8,193,411 | B2 | 6/2012 | Godwin et al. | |
| 2004/0031072 | A1 | 2/2004 | LaRosa et al. | |
| 2008/0166699 | A1 | 7/2008 | Baley et al. | |

OTHER PUBLICATIONS

M. S. Bachman et al., "Molecular Markers Linked to Brown Stem Rot Resistance Genes, $RbS_1$ and $Rbs_2$, in Soybean", Crop Science, Mar.-Apr. 2001, pp. 527-535, vol. 41

Bo-Keun Ha et al., "High-throughput SNP Genotyping by Melting Curve Analysis for Resistance to Southern Root-knot Nematode and Frogeye Leaf Spot in Soybean", J. Crop Sci. Biotech, Jun. 2008, pp. 91-100, vol. 11(2).

International Search Report and Written Opinion—PCT/US2014/022631—dated Jun. 27, 2014.

Ik-Young Choi et al., "A Soybean Transcript Map: Gene Distribution, Haplotype and Single-Nucleotide Polymorphism Analysis", Genetics, May 2007, pp. 685-696, vol. 176.

P. B. Cregan, et al., "An Integrated Genetic Linkage Map of the Soybean Genome"; Crop Science, 1999, pp. 1464-1490, vol. 39.

M. A. Graham, et al., "PRC Sampling of disease resistance-like sequences from a disease resistance gene cluster in soybean"; Theoretical and Applied Genetics, 2001, 105:50-57.

A. J. Hayes, et al., "Expression of two soybean resistance gene candidates shows divergence of paralogous single-copy genes"; Theoretical and Applied Genetics, 2000, 101:789-795.

David L. Hyten et al., A High Density Integrated Genetic Linkage Map of Soybean and the Development of a 1536 Universal Soy Linkage Panel for Quantitative Trait Locus Mapping, Crop Science, May-Jun. 2010, pp. 960-968, Vo. 50.

K. M. Polzin, et al.,; "Integration of Rps2, Rmd, and Rj2 Into Linkage Group J of the Soybean Molecular Map"; J. Hered 1994, 85:300-303—Abstract Only.

Q. J. Song, et al., "A new integrated genetic linkage map of the soybean"; Theoretical and Applied Genetics, 2004, 109:122-128.

(Continued)

*Primary Examiner* — Matthew R Keogh
*Assistant Examiner* — Bratislav Stankovic

(57) ABSTRACT

Various methods and compositions are provided for identifying and/or selecting soybean plants or soybean germplasm with improved resistance to Frogeye Leaf Spot and/or Brown Stem Rot. In certain embodiments, the method comprises detecting at least one marker locus that is associated with resistance to Frogeye Leaf Spot and/or Brown Stem Rot. In other embodiments, the method further comprises detecting at least one marker profile or haplotype associated with resistance to Frogeye Leaf Spot and/or Brown Stem Rot. In further embodiments, the method comprises crossing a selected soybean plant with a second soybean plant. Further provided are markers, primers, probes and kits useful for identifying and/or selecting soybean plants or soybean germplasm with improved resistance to Frogeye Leaf Spot and/or Brown Stem Rot.

4 Claims, 6 Drawing Sheets

(56) References Cited

OTHER PUBLICATIONS

W. Yang, et al., “Molecular mapping of new gene for resistance to frogeye leaf spot of soya bean in ’Peking”; Plant Breeding, 2001, 120:73-78.

* cited by examiner

Figure 2

| | | | Rbs3bf | Rbs3af | | HO | | FEYT | Rcs3 | | Rbs3b | Rbs3a |
|---|---|---|---|---|---|---|---|---|---|---|---|---|
| | | | 81.72 | 81.72 | | 82.4 | | 86.9 | 87 | | 87.8 | 87.8 |
| | Ge Name | | S01584-1 | S04821-1 | | S00008-4 | | S06363-1 | S00005-01 | | S07157-2 | S07157-1 |
| | XB19V06 | Rbs3a + FEYT | 3,3 | 1,1 | | Neg | | 2,2 | 16,16 | | 0,0 | 1,1 |
| | ZB31B07 | Rbs3b + Rcs3 | 3,3 | 3,3 | | Neg | | 2,2 | 15,15 | | 1,1 | 0,0 |
| | | | | | | | | | | | | |
| Future | NEW | Rbs3a + Rcs3 | 3,3 | 1,1 | | Neg | | 2,2 | 15,15 | | 0,0 | 1,1 |
| Current | NEW | Rbs3? + Rcs3 | 3,3 | 3,3 | | Neg | | 2,2 | 15,15 | | 0,0 | 1,1 |

Figure 3

| Marker Name | Locus Name | LG | Physical Position | Genetic Position (cM) |
|---|---|---|---|---|
| BARC-016027-02038 | BARC-016027-02038 | J (16) | 133,349 | 2.34 |
| BARC-028423-05867 | BARC-028423-05867 | J (16) | 724,502 | 4.91 |
| BARC-013639-01204 | BARC-013639-01204 | J (16) | 774,054 | 5.42 |
| BARC-063377-18348 | BARC-063377-18348 | J (16) | 1,061,926 | 8.18 |
| BARC-024473-04898 | BARC-024473-04898 | J (16) | 1,103,589 | 8.58 |
| BARCSOYSSR_16_0062 | BARCSOYSSR_16_0062 | J (16) | 1,141,072 | 10.55 |
| Satt249 | Satt249 | J (16) | 1,141,072 | 10.55 |
| BARC-013651-01218 | BARC-013651-01218 | J (16) | 1,348,520 | 11.40 |
| BARCSOYSSR_16_0083 | BARCSOYSSR_16_0083 | J (16) | 1,543,289 | 12.13 |
| Satt674 | Satt674 | J (16) | 1,543,289 | 12.13 |
| BARCSOYSSR_16_0090 | BARCSOYSSR_16_0090 | J (16) | 1,631,806 | 12.21 |
| Satt287 | Satt287 | J (16) | 1,631,806 | 12.21 |
| BARC-018981-03289 | BARC-018981-03289 | J (16) | 2,314,419 | 19.26 |
| BARCSOYSSR_16_0171 | BARCSOYSSR_16_0171 | J (16) | 2,893,992 | 22.52 |
| Sct_046 | Sct_046 | J (16) | 2,893,992 | 22.52 |
| BARCSOYSSR_16_0179 | BARCSOYSSR_16_0179 | J (16) | 3,050,011 | 22.97 |
| Sat_228 | Sat_228 | J (16) | 3,050,011 | 22.97 |
| BARC-028599-05966 | BARC-028599-05966 | J (16) | 3,137,659 | 23.17 |
| BARC-059355-15761 | BARC-059355-15761 | J (16) | 3,363,314 | 24.28 |
| BARC-042521-08287 | BARC-042521-08287 | J (16) | 3,534,838 | 24.37 |
| BARC-013299-00471 | BARC-013299-00471 | J (16) | 3,597,317 | 24.82 |
| BARC-014573-01581 | BARC-014573-01581 | J (16) | 3,597,402 | 24.82 |
| BARC-018093-02513 | BARC-018093-02513 | J (16) | 3,847,598 | 25,29 |
| BARC-045157-08897 | BARC-045157-08897 | J (16) | 3,900,245 | 25.35 |
| BARC-014467-01559 | BARC-014467-01559 | J (16) | 3,962,333 | 25.69 |
| BARC-029477-06200 | BARC-029477-06200 | J (16) | 4,763,389 | 31.14 |
| BARC-031525-07106 | BARC-031525-07106 | J (16) | 4,924,406 | 34.78 |
| BARC-031195-07010 | BARC-031195-07010 | J (16) | 4,924,462 | 34.78 |
| BARC-028307-05823 | BARC-028307-05823 | J (16) | 4,936,902 | 34.78 |
| BARC-031951-07227 | BARC-031951-07227 | J (16) | 4,936,964 | 34.94 |
| BARC-065799-19753 | BARC-065799-19753 | J (16) | 5,040,869 | 35.44 |
| BARCSOYSSR_16_0377 | BARCSOYSSR_16_0377 | J (16) | 6,273,768 | 38.03 |
| Satt693 | Satt693 | J (16) | 6,273,768 | 38.03 |

Figure 3 (continued)

| Marker Name | Locus Name | LG | Physical Position | Genetic Position (cM) |
|---|---|---|---|---|
| BARC-018889-03032 | BARC-018889-03032 | J (16) | 6,474,327 | 38.62 |
| BARCSOYSSR_16_0424 | BARCSOYSSR_16_0424 | J (16) | 7,054,261 | 40.67 |
| Sat_370 | Sat_370 | J (16) | 7,054,261 | 40.67 |
| BARC-028159-05778 | BARC-028159-05778 | J (16) | 7,070,781 | 41.63 |
| BARC-059919-16214 | BARC-059919-16214 | J (16) | 7,165,978 | 42.08 |
| BARC-053335-11801 | BARC-053335-11801 | J (16) | 7,237,770 | 42.31 |
| BARC-048299-10543 | BARC-048299-10543 | J (16) | 9,593,463 | 44.34 |
| BARC-058125-15101 | BARC-058125-15101 | J (16) | 10,818,091 | 44.60 |
| BARC-058115-15097 | BARC-058115-15097 | J (16) | 13,368,263 | 44.60 |
| BARC-058941-15515 | BARC-058941-15515 | J (16) | 14,534,998 | 44.60 |
| BARC-060857-16934 | BARC-060857-16934 | J (16) | 14,887,272 | 44.61 |
| BARC-056593-14514 | BARC-056593-14514 | J (16) | 15,091,717 | 44.61 |
| BARC-052587-11515 | BARC-052587-11515 | J (16) | 15,536,387 | 44.61 |
| BARC-062281-17737 | BARC-062281-17737 | J (16) | 16,322,634 | 44.61 |
| BARC-025801-05075 | BARC-025801-05075 | J (16) | 16,552,294 | 44.61 |
| BARC-059701-16014 | BARC-059701-16014 | J (16) | 19,326,141 | 44.61 |
| BARC-038343-10046 | BARC-038343-10046 | J (16) | 19,423,620 | 44.61 |
| BARC-013151-01456 | BARC-013151-01456 | J (16) | 20,512,221 | 44.61 |
| BARC-010869-00787 | BARC-010869-00787 | J (16) | 21,152,273 | 44.61 |
| BARC-051521-11150 | BARC-051521-11150 | J (16) | 21,264,807 | 44.61 |
| BARCSOYSSR_16_0703 | BARCSOYSSR_16_0703 | J (16) | 23,096,039 | 45.66 |
| Satt529 | Satt529 | J (16) | 23,096,039 | 45.66 |
| BARC-059377-15777 | BARC-059377-15777 | J (16) | 25,697,824 | 46.05 |
| BARCSOYSSR_16_0803 | BARCSOYSSR_16_0803 | J (16) | 26,813,827 | 46.10 |
| Sat_165 | Sat_165 | J (16) | 26,813,827 | 46.10 |
| BARCSOYSSR_16_0840 | BARCSOYSSR_16_0840 | J (16) | 27,633,714 | 46.11 |
| Satt622 | Satt622 | J (16) | 27,633,714 | 46.11 |
| BARCSOYSSR_16_0885 | BARCSOYSSR_16_0885 | J (16) | 28,589,375 | 47.36 |
| Satt215 | Satt215 | J (16) | 28,589,375 | 47.36 |
| BARC-029037-06053 | BARC-029037-06053 | J (16) | 29,156,483 | 51.57 |
| BARC-038949-07404 | BARC-038949-07404 | J (16) | 30,065,357 | 57.70 |
| BARC-059837-16121 | BARC-059837-16121 | J (16) | 31,151,468 | 58.39 |
| BARC-042193-08207 | BARC-042193-08207 | J (16) | 30,395,923 | 62.96 |
| BARC-032663-09006 | BARC-032663-09006 | J (16) | 30,962,138 | 65.78 |
| BARC-017697-03107 | BARC-017697-03107 | J (16) | 31,075,508 | 66.45 |

Figure 3 (continued)

| Marker Name | Locus Name | LG | Physical Position | Genetic Position (cM) |
|---|---|---|---|---|
| BARC-024047-04716 | BARC-024047-04716 | J (16) | 31,105,844 | 66.47 |
| BARC-022077-04282 | BARC-022077-04282 | J (16) | 31,154,859 | 66.56 |
| BARC-014795-01662 | BARC-014795-01662 | J (16) | 31,155,317 | 66.56 |
| BARC-042895-08450 | BARC-042895-08450 | J (16) | 31,292,648 | 67.05 |
| BARC-043111-08534 | BARC-043111-08534 | J (16) | 31,461,544 | 67.48 |
| BARC-060179-16450 | BARC-060179-16450 | J (16) | 31,613,798 | 67.74 |
| BARC-011645-00322 | BARC-011645-00322 | J (16) | 31,635,367 | 67.90 |
| BARCSOYSSR_16_1073 | BARCSOYSSR_16_1073 | J (16) | 31,795,061 | 68.81 |
| Sctt001 | Sctt001 | J (16) | 31,795,061 | 68.81 |
| BARC-010297-00580 | BARC-010297-00580 | J (16) | 31,996,027 | 69.90 |
| S01584-1-Q5 | S01584-1 | J (16) | 32,308,049 | 70.73 |
| S04857-1-A | S04857-1 | J (16) | 32,308,250 | 70.73 |
| S04831-1-Q2 | S04831-1 | J (16) | 32,352,386 | 70.85 |
| BARC-017835-02393 | BARC-017835-02393 | J (16) | 32,526,995 | 71.32 |
| BARC-012971-00414 | BARC-012971-00414 | J (16) | 32,573,581 | 71.56 |
| BARC-024115-04764 | BARC-024115-04764 | J (16) | 32,962,414 | 71.92 |
| S06363-1-Q1 | S06363-1 | J (16) | 33,328,806 | 73.01 |
| S14236-1-Q3 | S14236-1 | J (16) | 33,368,242 | 73.13 |
| S00005-01-A | S00005-01 | J (16) | 33,387,560 | 73.19 |
| BARC-040393-07727 | BARC-040393-07727 | J (16) | 33,410,287 | 73.26 |
| BARC-025217-06463 | BARC-025217-06463 | J (16) | 33,513,918 | 73.90 |
| BARCSOYSSR_16_1165 | BARCSOYSSR_16_1165 | J (16) | 33,538,157 | 74.90 |
| Satt567 | Satt567 | J (16) | 33,538,157 | 74.90 |
| S16015-001-Q001 | S16015-001 | J (16) | 33,564,749 | 75.00 |
| S07157-1-Q1 | S07157-1 | J (16) | 33,636,569 | 75.28 |
| S07157-2-Q1 | S07157-2 | J (16) | 33,636,572 | 75.28 |
| S16023-001-Q002 | S16023-001 | J (16) | 33,636,969 | 75.29 |
| BARC-028589-05965 | BARC-028589-05965 | J (16) | 33,853,031 | 76.14 |
| BARC-053847-12078 | BARC-053847-12078 | J (16) | 34,475,602 | 77.27 |
| BARC-051715-11216 | BARC-051715-11216 | J (16) | 35,032,380 | 77.40 |
| BARC-045099-08885 | BARC-045099-08885 | J (16) | 35,208,435 | 78.97 |
| BARC-025851-05117 | BARC-025851-05117 | J (16) | 35,571,437 | 80.79 |
| BARC-044031-08587 | BARC-044031-08587 | J (16) | 35,587,464 | 81.41 |
| BARCSOYSSR_16_1234 | BARCSOYSSR_16_1234 | J (16) | 35,718,507 | 82.03 |
| Satt431 | Satt431 | J (16) | 35,718,507 | 82.03 |
| BARC-045133-08889 | BARC-045133-08889 | J (16) | 36,163,500 | 84.07 |

Figure 3 (continued)

| Marker Name | Locus Name | LG | Physical Position | Genetic Position (cM) |
|---|---|---|---|---|
| BARC-015307-02272 | BARC-015307-02272 | J (16) | 36,221,550 | 84.76 |
| BARC-011625-00310 | BARC-011625-00310 | J (16) | 36,544,211 | 85.58 |
| BARC-024229-04809 | BARC-024229-04809 | J (16) | 36,641,788 | 86.17 |
| BARC-048135-10500 | BARC-048135-10500 | J (16) | 36,732,539 | 86.82 |
| BARC-019219-03397 | BARC-019219-03397 | J (16) | 36,921,370 | 87.38 |
| BARC-030203-06832 | BARC-030203-06832 | J (16) | 37,108,010 | 87.58 |
| BARC-029163-06102 | BARC-029163-06102 | J (16) | 37,181,366 | 88.51 |
| BARC-030817-06946 | BARC-030817-06946 | J (16) | 37,289,136 | 88.93 |

SEQUENCE LISTING

<160> NUMBER OF SEQ ID NOS: 80

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gaatgggtgt gaccttcctg 20

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
cagtttgaaa agggttcagc a 21

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
agttgctgcc gtcatttgat 20

<210> SEQ ID NO 4
<211> LENGTH: 21
<212> TYPE: DNA
<213> ORGANISM: Artificial Sequence
<220> FEATURE:
<223> OTHER INFORMATION: Primer

<400> SEQUENCE: 4
aatgaggatt tggtcgttgt g 21

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ctccgctcag gatcctctaa a 21

<210> SEQ ID NO 6
<211> LENGTH: 24
<212> TYPE: DNA
<213> ORGANISM: Artificial Sequence
<220> FEATURE:
<223> OTHER INFORMATION: Primer

<400> SEQUENCE: 6
tcactattct ctgatgttga cacg 24

<210> SEQ ID NO 7
<211> LENGTH: 17
<212> TYPE: DNA
<213> ORGANISM: Artificial Sequence
<220> FEATURE:
<223> OTHER INFORMATION: Probe

<400> SEQUENCE: 7
agcttgagga taggata 17

<210> SEQ ID NO 8
<211> LENGTH: 19
<212> TYPE: DNA
<213> ORGANISM: Artificial Sequence
<220> FEATURE:
<223> OTHER INFORMATION: Probe

<400> SEQUENCE: 8
aagcttgaag attggatat 19

<210> SEQ ID NO 9
<211> LENGTH: 17
<212> TYPE: DNA
<213> ORGANISM: Artificial Sequence
<220> FEATURE:
<223> OTHER INFORMATION: Probe

<400> SEQUENCE: 9
actattcggt tctggac 17

<210> SEQ ID NO 10
<211> LENGTH: 16
<212> TYPE: DNA
<213> ORGANISM: Artificial Sequence
<220> FEATURE:
<223> OTHER INFORMATION: Probe

<400> SEQUENCE: 10
ccgactattt ggttct 16

<210> SEQ ID NO 11
<211> LENGTH: 17
<212> TYPE: DNA
<213> ORGANISM: Artificial Sequence
<220> FEATURE:
<223> OTHER INFORMATION: Probe

<400> SEQUENCE: 11
atcatccgtt tgaagaa 17

<210> SEQ ID NO 12
<211> LENGTH: 18
<212> TYPE: DNA
<213> ORGANISM: Artificial Sequence
<220> FEATURE:
<223> OTHER INFORMATION: Probe

<400> SEQUENCE: 12
atcatccatt tgaagaag 18

<210> SEQ ID NO 13
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 13
gatttggagt agagagcaca atttgataag tttttcctcc aaatatygtc aatctagaaa 60

-continued

```
gggtagaatt agatatrcgg aggacttgtg catcatcatg maaagaacaa cctataagca    120

tcaaagaatt taaaacaasa cagtttgaaa agggttcagc acagtcattg tcagttgcag    180

taaatttgaa atatcctatc ctcaagcttt ttaatgcagg caggttaaga gattttggaa    240

gtattatttc aggaaggtca cacccattcc aaatctcaag atatgtcaaa gacttagagr    300

aaaagattaa agggatggac tcaaagttgg gtctaaagcc tgaatatata cgcaatgtca    360

agtgctggac attrtgaaac acagcatatt taatgatcct a                        401
```

<210> SEQ ID NO 14
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 14

```
gatttggagt agagagcaca atttgataag tttttcctcc aaatatygtc aatctagaaa     60

gggtagaatt agatatrcgg aggacttgtg catcatcatg maaagaacaa cctataagca    120

tcaaagaatt taaaacaasa cagtttgaaa agggttcagc acagtcattg tcagttgcag    180

taaatttgaa atatccaatc ttcaagcttt ttaatgcagg caggttaaga gattttggaa    240

gtattatttc aggaaggtca cacccattcc aaatctcaag atatgtcaaa gacttagagr    300

aaaagattaa agggatggac tcaaagttgg gtctaaagcc tgaatatata cgcaatgtca    360

agtgctggac attrtgaaac acagcatatt taatgatcct a                        401
```

<210> SEQ ID NO 15
<211> LENGTH: 401
<212> TYPE: DNA
<213> ORGANISM: Artificial Sequence
<220> FEATURE:
<223> OTHER INFORMATION: Consensus Reference Sequence
<220> FEATURE:
<221> NAME/KEY: misc_feature
<222> LOCATION: 156, 176
<223> OTHER INFORMATION: n = A,T,C or G

<400> SEQUENCE: 15

```
atctaaagtt cacaatttta aggaataatt aattttdaag tccttgaatt tttctaaatt     60

ttaaatttca gttcctaaat aaagatttaa cttgtaaaag tgctcaaaat twtatttagt    120

tacaactttt agttgctgcc gtcatttgat gatgangtgg tgtcatgyga aacaanataa    180

gataatcaac cccgactatt cggttctgga cctcggctvt cagttgtcaa arcttgggtc    240

aacccttyca caacraccaa atcctcatta aatttataat tttakaattt atttttattt    300

ttactgtyca ctattcacca aataatgcac atgataaaaa gttatcaatg catcmtttgt    360

aactttatgt ttgtgatrct ttattctcct tgtattatac t                        401
```

<210> SEQ ID NO 16
<211> LENGTH: 401
<212> TYPE: DNA
<213> ORGANISM: Artificial Sequence
<220> FEATURE:
<223> OTHER INFORMATION: Consensus Reference Sequence
<220> FEATURE:
<221> NAME/KEY: misc_feature
<222> LOCATION: 156, 176
<223> OTHER INFORMATION: n = A,T,C or G

<400> SEQUENCE: 16

```
atctaaagtt cacaatttta aggaataatt aattttdaag tccttgaatt tttctaaatt     60
```

-continued

```
ttaaatttca gttcctaaat aaagatttaa cttgtaaaag tgctcaaaat twtatttagt    120

tacaactttt agttgctgcc gtcatttgat gatgangtgg tgtcatgyga aacaanataa    180

gataatcaac cccgactatt tggttctgga cctcggctvt cagttgtcaa arcttgggtc    240

aacccttyca caacraccaa atcctcatta aatttataat tttakaattt atttttattt    300

ttactgtyca ctattcacca aataatgcac atgataaaaa gttatcaatg catcmtttgt    360

aactttatgt ttgtgatrct ttattctcct tgtattatac t                        401
```

<210> SEQ ID NO 17
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 17

```
catgtctaga aagattaaat gttgttagag gaaatatata atggatgaat ataattacac     60

agggtaagaa gtaaaataaa ttcaggcact ccgttcacaa gaagaaacaa acttgtaaaa    120

aatagaatta gggcatcatc agagcatctg ggctcygctc aggatcctct aaagaaaaat    180

gagaagccat cctatcatcc atttgaagaa gttgccgtgt caacatcaga gaatagtgaa    240

gatgctacac tyactgcagc agaaacaagt agaacaatta ttgaggtact cagttgtatt    300

aattttgcta rtcaatgatg taatgtaacc tcacagaacg aggaaatttt ttttggcaaa    360

catttaggtt ttctcatttt agtgctatat ttttacaaca g                        401
```

<210> SEQ ID NO 18
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 18

```
catgtctaga aagattaaat gttgttagag gaaatatata atggatgaat ataattacac     60

agggtaagaa gtaaaataaa ttcaggcact ccgttcacaa gaagaaacaa acttgtaaaa    120

aatagaatta gggcatcatc agagcatctg ggctcygctc aggatcctct aaagaaaaat    180

gagaagccat cctatcatcc gtttgaagaa gttgccgtgt caacatcaga gaatagtgaa    240

gatgctacac tyactgcagc agaaacaagt agaacaatta ttgaggtact cagttgtatt    300

aattttgcta rtcaatgatg taatgtaacc tcacagaacg aggaaatttt ttttggcaaa    360

catttaggtt ttctcatttt agtgctatat ttttacaaca g                        401
```

<210> SEQ ID NO 19
<211> LENGTH: 129
<212> TYPE: DNA
<213> ORGANISM: Artificial Sequence
<220> FEATURE:
<223> OTHER INFORMATION: Amplicon

<400> SEQUENCE: 19

```
cagtttgaaa agggttcagc acagtcattg tcagttgcag taaatttgaa atatcctatc     60

ctcaagcttt ttaatgcagg caggttaaga gattttggaa gtattatttc aggaaggtca    120

cacccattc                                                            129
```

<210> SEQ ID NO 20

-continued

<211> LENGTH: 129
<212> TYPE: DNA
<213> ORGANISM: Artificial Sequence
<220> FEATURE:
<223> OTHER INFORMATION: Amplicon

<400> SEQUENCE: 20
cagtttgaaa agggttcagc acagtcattg tcagttgcag taaatttgaa atatccaatc 60
ttcaagcttt ttaatgcagg caggttaaga gattttggaa gtattatttc aggaaggtca 120
cacccattc 129

<210> SEQ ID NO 21
<211> LENGTH: 139
<212> TYPE: DNA
<213> ORGANISM: Artificial Sequence
<220> FEATURE:
<223> OTHER INFORMATION: Amplicon
<220> FEATURE:
<221> NAME/KEY: misc_feature
<222> LOCATION: 26, 46
<223> OTHER INFORMATION: n = A,T,C or G

<400> SEQUENCE: 21
agttgctgcc gtcatttgat gatgangtgg tgtcatgyga aacaanataa gataatcaac 60
cccgactatt cggttctgga cctcggctvt cagttgtcaa arcttgggtc aacccttyca 120
caacraccaa atcctcatt 139

<210> SEQ ID NO 22
<211> LENGTH: 139
<212> TYPE: DNA
<213> ORGANISM: Artificial Sequence
<220> FEATURE:
<223> OTHER INFORMATION: Amplicon
<220> FEATURE:
<221> NAME/KEY: misc_feature
<222> LOCATION: 26, 46
<223> OTHER INFORMATION: n = A,T,C or G

<400> SEQUENCE: 22
agttgctgcc gtcatttgat gatgangtgg tgtcatgyga aacaanataa gataatcaac 60
cccgactatt tggttctgga cctcggctvt cagttgtcaa arcttgggtc aacccttyca 120
caacraccaa atcctcatt 139

<210> SEQ ID NO 23
<211> LENGTH: 87
<212> TYPE: DNA
<213> ORGANISM: Artificial Sequence
<220> FEATURE:
<223> OTHER INFORMATION: Amplicon

<400> SEQUENCE: 23
ctcygctcag gatcctctaa agaaaaatga gaagccatcc tatcatccat ttgaagaagt 60
tgccgtgtca acatcagaga atagtga 87

<210> SEQ ID NO 24
<211> LENGTH: 87
<212> TYPE: DNA
<213> ORGANISM: Artificial Sequence
<220> FEATURE:
<223> OTHER INFORMATION: Amplicon

<400> SEQUENCE: 24
ctcygctcag gatcctctaa agaaaaatga gaagccatcc tatcatccgt ttgaagaagt 60
tgccgtgtca acatcagaga atagtga 87

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
tcaacttcaa acatggcctc t 21

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
gcctctccat ttgcaacaat 20

<210> SEQ ID NO 27
<211> LENGTH: 24
<212> TYPE: DNA
<213> ORGANISM: Artificial Sequence
<220> FEATURE:
<223> OTHER INFORMATION: Primer

<400> SEQUENCE: 27
ggagaacgag taacacacaa caag 24

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
aggcacaagg tgctcaagac 20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tgaaggcatt gctctccttt 20

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
ctgaccaaag accctgttga c 21

<210> SEQ ID NO 31
<211> LENGTH: 20
<212> TYPE: DNA

<213> ORGANISM: Artificial Sequence
<220> FEATURE:
<223> OTHER INFORMATION: Primer

<400> SEQUENCE: 31
tgaaggcatt gctctccttt 20

<210> SEQ ID NO 32
<211> LENGTH: 21
<212> TYPE: DNA
<213> ORGANISM: Artificial Sequence
<220> FEATURE:
<223> OTHER INFORMATION: Primer

<400> SEQUENCE: 32
ctgaccaaag accctgttga c 21

<210> SEQ ID NO 33
<211> LENGTH: 21
<212> TYPE: DNA
<213> ORGANISM: Artificial Sequence
<220> FEATURE:
<223> OTHER INFORMATION: Primer

<400> SEQUENCE: 33
tggaataggt gggtatggtg a 21

<210> SEQ ID NO 34
<211> LENGTH: 26
<212> TYPE: DNA
<213> ORGANISM: Artificial Sequence
<220> FEATURE:
<223> OTHER INFORMATION: Primer

<400> SEQUENCE: 34
gcctactcat gtagttgaag atgacc 26

<210> SEQ ID NO 35
<211> LENGTH: 22
<212> TYPE: DNA
<213> ORGANISM: Artificial Sequence
<220> FEATURE:
<223> OTHER INFORMATION: Primer

<400> SEQUENCE: 35
atcttgaatg ctgctgttca tc 22

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
gttggttcat ctgagtctta tcca 24

<210> SEQ ID NO 37
<211> LENGTH: 17
<212> TYPE: DNA
<213> ORGANISM: Artificial Sequence
<220> FEATURE:
<223> OTHER INFORMATION: Probe

<400> SEQUENCE: 37
tcctctaggt agacagc 17

<210> SEQ ID NO 38
<211> LENGTH: 17
<212> TYPE: DNA
<213> ORGANISM: Artificial Sequence
<220> FEATURE:
<223> OTHER INFORMATION: Probe

<400> SEQUENCE: 38
ttgttcctcc aggtaga 17

<210> SEQ ID NO 39
<211> LENGTH: 17
<212> TYPE: DNA
<213> ORGANISM: Artificial Sequence
<220> FEATURE:
<223> OTHER INFORMATION: Probe

<400> SEQUENCE: 39
ctccattcct acttact 17

<210> SEQ ID NO 40
<211> LENGTH: 16
<212> TYPE: DNA
<213> ORGANISM: Artificial Sequence
<220> FEATURE:
<223> OTHER INFORMATION: Probe

<400> SEQUENCE: 40
tccattccca cttact 16

<210> SEQ ID NO 41
<211> LENGTH: 15
<212> TYPE: DNA
<213> ORGANISM: Artificial Sequence
<220> FEATURE:
<223> OTHER INFORMATION: Probe

<400> SEQUENCE: 41
tacacgcatt acagc 15

<210> SEQ ID NO 42
<211> LENGTH: 16
<212> TYPE: DNA
<213> ORGANISM: Artificial Sequence
<220> FEATURE:
<223> OTHER INFORMATION: Probe

<400> SEQUENCE: 42
ctgtacacgc gttaca 16

<210> SEQ ID NO 43
<211> LENGTH: 16
<212> TYPE: DNA
<213> ORGANISM: Artificial Sequence
<220> FEATURE:
<223> OTHER INFORMATION: Probe

<400> SEQUENCE: 43
ctgtacatgc gttaca 16

<210> SEQ ID NO 44
<211> LENGTH: 16
<212> TYPE: DNA
<213> ORGANISM: Artificial Sequence
<220> FEATURE:

```
<223> OTHER INFORMATION: Probe

<400> SEQUENCE: 44

ctgtacacgc gttaca                                                   16


<210> SEQ ID NO 45
<211> LENGTH: 18
<212> TYPE: DNA
<213> ORGANISM: Artificial Sequence
<220> FEATURE:
<223> OTHER INFORMATION: Probe

<400> SEQUENCE: 45

ttaaacctac atcctttg                                                 18


<210> SEQ ID NO 46
<211> LENGTH: 16
<212> TYPE: DNA
<213> ORGANISM: Artificial Sequence
<220> FEATURE:
<223> OTHER INFORMATION: Probe

<400> SEQUENCE: 46

ttaaacctgc atcctt                                                   16


<210> SEQ ID NO 47
<211> LENGTH: 20
<212> TYPE: DNA
<213> ORGANISM: Artificial Sequence
<220> FEATURE:
<223> OTHER INFORMATION: Probe

<400> SEQUENCE: 47

caatttacta caatttcctc                                               20


<210> SEQ ID NO 48
<211> LENGTH: 19
<212> TYPE: DNA
<213> ORGANISM: Artificial Sequence
<220> FEATURE:
<223> OTHER INFORMATION: Probe

<400> SEQUENCE: 48

caatttacta cagtttcct                                                19


<210> SEQ ID NO 49
<211> LENGTH: 401
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 325, 400
<223> OTHER INFORMATION: n = A,T,C or G

<400> SEQUENCE: 49

tatcagcaaa attatawtga gtagttattt tctgacaaca ttttatgctc tgttcctgct     60

tttatttmat tcctcaggat ttamtctcgg attaaatggg tcacttaaaa gtyctdaggc    120

aaagtgcaga gagagggaga gacaagcact cctcaacttc aaacatggcc tctragatga    180

ctctggcatg ctgtctacct agaggaacaa tgacaataat agagattgtt gcaaatdgag    240

aggcattcaa tgcaaygatg aaactggtca cgtacaagta ctcaatcttc attgtccaga    300

tagacattat ttgacaggtg caatnaatct cacttcrttg attcacttgc aaaacattga    360
```

acatctgatc tcagcaataa tgatttttta cgatgttacn t 401

<210> SEQ ID NO 50
<211> LENGTH: 401
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 325, 400
<223> OTHER INFORMATION: n = A,T,C or G

<400> SEQUENCE: 50
tatcagcaaa attatawtga gtagttattt tctgacaaca ttttatgctc tgttcctgct 60
tttatttmat tcctcaggat ttamtctcgg attaaatggg tcacttaaaa gtyctdaggc 120
aaagtgcaga gagagggaga gacaagcact cctcaacttc aaacatggcc tctragatga 180
ctctggcatg ctgtctacct ggaggaacaa tgacaataat agagattgtt gcaaatdgag 240
aggcattcaa tgcaaygatg aaactggtca cgtacaagta ctcaatcttc attgtccaga 300
tagacattat ttgacaggtg caatnaatct cacttcrttg attcacttgc aaaacattga 360
acatctgatc tcagcaataa tgatttttta cgatgttacn t 401

<210> SEQ ID NO 51
<211> LENGTH: 401
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 246
<223> OTHER INFORMATION: n = A,T,C or G

<400> SEQUENCE: 51
ttttggattt actgcttcaa aatgttcaca rtasatgtcg tcacctttac aaagtaattt 60
tggcctgcag tttaattgac tacaatatag atataaatat aaacatcttc tttatrtcaa 120
atcttaaatc tatcactaat gtcctaggca caaggtgctc aagacagata caactaatag 180
ttgcaccttg tatagtaagt aggaatggag ctgatcattt tgctgctctc gttgrtcctt 240
tcctcnttag tgttaatggt tctcttcttg ttgtgtgtta ctcgttctcc taaagcaatg 300
gaaggcatcc ctggcagcct tggttggyct attgtgggag agagtttctc attcctctct 360
gatttttcaa gtccctcygg aatctttagc ttcatgaaca a 401

<210> SEQ ID NO 52
<211> LENGTH: 401
<212> TYPE: DNA
<213> ORGANISM: Artificial Sequence
<220> FEATURE:
<223> OTHER INFORMATION: Consensus reference sequence
<220> FEATURE:
<221> NAME/KEY: misc_feature
<222> LOCATION: 246
<223> OTHER INFORMATION: n = A,T,C or G

<400> SEQUENCE: 52
ttttggattt actgcttcaa aatgttcaca rtasatgtcg tcacctttac aaagtaattt 60
tggcctgcag tttaattgac tacaatatag atataaatat aaacatcttc tttatrtcaa 120
atcttaaatc tatcactaat gtcctaggca caaggtgctc aagacagata caactaatag 180

-continued

```
ttgcaccttg tatagtaagt gggaatggag ctgatcattt tgctgctctc gttgrtcctt    240

tcctcnttag tgttaatggt tctcttcttg ttgtgtgtta ctcgttctcc taaagcaatg    300

gaaggcatcc ctggcagcct tggttggyct attgtgggag agagtttctc attcctctct    360

gatttttcaa gtccctcygg aatctttagc ttcatgaaca a                        401
```

```
<210> SEQ ID NO 53
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 53

tcagacaatg gacatccaag caatgcaaca ttggttgatc acagagtttc atttgaatta     60

accggggaag atgttgcycg gtgtcttgca aataaaactg gggtattgct tcgaaacatg    120

tcagggtctt cacaaggtat actgaccaaa gaccctgttg acagagaaag ggtgcaaata    180

gacaccaata gtagctgtaa cgcrtgtaca gagaaaactg acgataagcc tgacaatcct    240

gtaggaaaag gagagcaatg ccttcacaag caaaattctg taaattcttc caaagaattc    300

aattttgaca acaggaaagg tgatgtttct gttactactg gcagtggcta tgagtggtgg    360

actaacagga aggttgctgg gaaggaaggt agatcagcca a                        401
```

```
<210> SEQ ID NO 54
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 54

tcagacaatg gacatccaag caatgcaaca ttggttgatc acagagtttc atttgaatta     60

accggggaag atgttgcycg gtgtcttgca aataaaactg gggtattgct tcgaaacatg    120

tcagggtctt cacaaggtat actgaccaaa gaccctgttg acagagaaag ggtgcaaata    180

gacaccaata gtagctgtaa tgcrtgtaca gagaaaactg acgataagcc tgacaatcct    240

gtaggaaaag gagagcaatg ccttcacaag caaaattctg taaattcttc caaagaattc    300

aattttgaca acaggaaagg tgatgtttct gttactactg gcagtggcta tgagtggtgg    360

actaacagga aggttgctgg gaaggaaggt agatcagcca a                        401
```

```
<210> SEQ ID NO 55
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 55

gacaatggac atccaagcaa tgcaacattg gttgatcaca gagtttcatt tgaattaacc     60

ggggaagatg ttgcycggtg tcttgcaaat aaaactgggg tattgcttcg aaacatgtca    120

gggtcttcac aaggtatact gaccaaagac cctgttgaca gagaaagggt gcaaatagac    180

accaatagta gctgtaaygc atgtacagag aaaactgacg ataagcctga caatcctgta    240

ggaaaaggag agcaatgcct tcacaagcaa aattctgtaa attcttccaa agaattcaat    300

tttgacaaca ggaaaggtga tgtttctgtt actactggca gtggctatga gtggtggact    360

aacaggaagg ttgctgggaa ggaaggtaga tcagccaaca g                        401
```

<210> SEQ ID NO 56
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 56
gacaatggac atccaagcaa tgcaacattg gttgatcaca gagtttcatt tgaattaacc 60
ggggaagatg ttgcycggtg tcttgcaaat aaaactgggg tattgcttcg aaacatgtca 120
gggtcttcac aaggtatact gaccaaagac cctgttgaca gagaaagggt gcaaatagac 180
accaatagta gctgtaaygc gtgtacagag aaaactgacg ataagcctga caatcctgta 240
ggaaaaggag agcaatgcct tcacaagcaa aattctgtaa attcttccaa agaattcaat 300
tttgacaaca ggaaaggtga tgtttctgtt actactggca gtggctatga gtggtggact 360
aacaggaagg ttgctgggaa ggaaggtaga tcagccaaca g 401

<210> SEQ ID NO 57
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 57
agacattctg attgttaact ccctccasaa tctcatctcc aaacacaact tctgaatcga 60
tcamcgagtt tttaataggc taggcagcat catttgcaac ttgtggtggt gttgatcact 120
tatgtctata taacagcttt gcccttcggt aagaaagaga taatagagtg gaatagrtgg 180
gtatggtgaa gcaaaggatg caggtttaat aacaggtact aagtcttggt ggtcatcttc 240
aactacatga gtaggcaaca atttggtatt aggcatatgg tgggtcttga ttcatacagc 300
aaggaacagg aaattataca aaattccgtt gataattgtt gatagtactc atttggagaa 360
tgattataga gatttaagtt aaaaaaatct ataaaataaa t 401

<210> SEQ ID NO 58
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 58
agacattctg attgttaact ccctccasaa tctcatctcc aaacacaact tctgaatcga 60
tcamcgagtt tttaataggc taggcagcat catttgcaac ttgtggtggt gttgatcact 120
tatgtctata taacagcttt gcccttcggt aagaaagaga taatagagtg gaatagrtgg 180
gtatggtgaa gcaaaggatg taggtttaat aacaggtact aagtcttggt ggtcatcttc 240
aactacatga gtaggcaaca atttggtatt aggcatatgg tgggtcttga ttcatacagc 300
aaggaacagg aaattataca aaattccgtt gataattgtt gatagtactc atttggagaa 360
tgattataga gatttaagtt aaaaaaatct ataaaataaa t 401

<210> SEQ ID NO 59
<211> LENGTH: 401
<212> TYPE: DNA
<213> ORGANISM: Artificial Sequence
<220> FEATURE:

<223> OTHER INFORMATION: Consensus reference sequence

<400> SEQUENCE: 59
acagctgggc tttcttccca atgttacagt cagaaatgaa ttgaggtttt agtgtattgc 60
aacatgactt aacctgtatg gtataaaagc aaaaaggatt ttccatttct ctgcagaacc 120
tttagtatac tgaaatgtat atttgaatat ttgaagacct tatcttgaat gctgctgttc 180
atcatatacc tttgaggaaa ctgtagtaaa ttgatgattg gataagactc agatgaacca 240
acagttgtta tattccttga ggacctaaag tagaatgcaa ggggagcata gtggtagtag 300
gtagggacca atagtgggtt atattatatt tatataattg tgaaacatta cttcttgcat 360
ttcatccttt caaatataca gaaatagcaa agtacaggta t 401

<210> SEQ ID NO 60
<211> LENGTH: 401
<212> TYPE: DNA
<213> ORGANISM: Artificial Sequence
<220> FEATURE:
<223> OTHER INFORMATION: Consensus reference sequence

<400> SEQUENCE: 60
acagctgggc tttcttccca atgttacagt cagaaatgaa ttgaggtttt agtgtattgc 60
aacatgactt aacctgtatg gtataaaagc aaaaaggatt ttccatttct ctgcagaacc 120
tttagtatac tgaaatgtat atttgaatat ttgaagacct tatcttgaat gctgctgttc 180
atcatatacc tttgaggaaa ttgtagtaaa ttgatgattg gataagactc agatgaacca 240
acagttgtta tattccttga ggacctaaag tagaatgcaa ggggagcata gtggtagtag 300
gtagggacca atagtgggtt atattatatt tatataattg tgaaacatta cttcttgcat 360
ttcatccttt caaatataca gaaatagcaa agtacaggta t 401

<210> SEQ ID NO 61
<211> LENGTH: 92
<212> TYPE: DNA
<213> ORGANISM: Artificial Sequence
<220> FEATURE:
<223> OTHER INFORMATION: Amplicon

<400> SEQUENCE: 61
tcaacttcaa acatggcctc tragatgact ctggcatgct gtctacctag aggaacaatg 60
acaataatag agattgttgc aaatdgagag gc 92

<210> SEQ ID NO 62
<211> LENGTH: 92
<212> TYPE: DNA
<213> ORGANISM: Artificial Sequence
<220> FEATURE:
<223> OTHER INFORMATION: Amplicon

<400> SEQUENCE: 62
tcaacttcaa acatggcctc tragatgact ctggcatgct gtctacctgg aggaacaatg 60
acaataatag agattgttgc aaatdgagag gc 92

<210> SEQ ID NO 63
<211> LENGTH: 145
<212> TYPE: DNA
<213> ORGANISM: Artificial Sequence
<220> FEATURE:
<223> OTHER INFORMATION: Amplicon
<220> FEATURE:
<221> NAME/KEY: misc_feature
<222> LOCATION: 101
<223> OTHER INFORMATION: n = A,T,C or G

<400> SEQUENCE: 63
aggcacaagg tgctcaagac agatacaact aatagttgca ccttgtatag taagtaggaa 60
tggagctgat cattttgctg ctctcgttgr tcctttcctc nttagtgtta atggttctct 120
tcttgttgtg tgttactcgt tctcc 145

<210> SEQ ID NO 64
<211> LENGTH: 145
<212> TYPE: DNA
<213> ORGANISM: Artificial Sequence
<220> FEATURE:
<223> OTHER INFORMATION: Amplicon
<220> FEATURE:
<221> NAME/KEY: misc_feature
<222> LOCATION: 101
<223> OTHER INFORMATION: n = A,T,C or G

<400> SEQUENCE: 64
aggcacaagg tgctcaagac agatacaact aatagttgca ccttgtatag taagtgggaa 60
tggagctgat cattttgctg ctctcgttgr tcctttcctc nttagtgtta atggttctct 120
tcttgttgtg tgttactcgt tctcc 145

<210> SEQ ID NO 65
<211> LENGTH: 125
<212> TYPE: DNA
<213> ORGANISM: Artificial Sequence
<220> FEATURE:
<223> OTHER INFORMATION: Amplicon

<400> SEQUENCE: 65
ctgaccaaag accctgttga cagagaaagg gtgcaaatag acaccaatag tagctgtaac 60
gcrtgtacag agaaaactga cgataagcct gacaatcctg taggaaaagg agagcaatgc 120
cttca 125

<210> SEQ ID NO 66
<211> LENGTH: 125
<212> TYPE: DNA
<213> ORGANISM: Artificial Sequence
<220> FEATURE:
<223> OTHER INFORMATION: Amplicon

<400> SEQUENCE: 66
ctgaccaaag accctgttga cagagaaagg gtgcaaatag acaccaatag tagctgtaat 60
gcrtgtacag agaaaactga cgataagcct gacaatcctg taggaaaagg agagcaatgc 120
cttca 125

<210> SEQ ID NO 67
<211> LENGTH: 125
<212> TYPE: DNA
<213> ORGANISM: Artificial Sequence
<220> FEATURE:
<223> OTHER INFORMATION: Amplicon

<400> SEQUENCE: 67
ctgaccaaag accctgttga cagagaaagg gtgcaaatag acaccaatag tagctgtaay 60
gcatgtacag agaaaactga cgataagcct gacaatcctg taggaaaagg agagcaatgc 120
cttca 125

<210> SEQ ID NO 68
<211> LENGTH: 125
<212> TYPE: DNA
<213> ORGANISM: Artificial Sequence
<220> FEATURE:
<223> OTHER INFORMATION: Amplicon

<400> SEQUENCE: 68
ctgaccaaag accctgttga cagagaaagg gtgcaaatag acaccaatag tagctgtaay 60
gcgtgtacag agaaaactga cgataagcct gacaatcctg taggaaaagg agagcaatgc 120
cttca 125

<210> SEQ ID NO 69
<211> LENGTH: 88
<212> TYPE: DNA
<213> ORGANISM: Artificial Sequence
<220> FEATURE:
<223> OTHER INFORMATION: Amplicon

<400> SEQUENCE: 69
tggaatagrt gggtatggtg aagcaaagga tgcaggttta ataacaggta ctaagtcttg 60
gtggtcatct tcaactacat gagtaggc 88

<210> SEQ ID NO 70
<211> LENGTH: 88
<212> TYPE: DNA
<213> ORGANISM: Artificial Sequence
<220> FEATURE:
<223> OTHER INFORMATION: Amplicon

<400> SEQUENCE: 70
tggaatagrt gggtatggtg aagcaaagga tgtaggttta ataacaggta ctaagtcttg 60
gtggtcatct tcaactacat gagtaggc 88

<210> SEQ ID NO 71
<211> LENGTH: 81
<212> TYPE: DNA
<213> ORGANISM: Artificial Sequence
<220> FEATURE:
<223> OTHER INFORMATION: Amplicon

<400> SEQUENCE: 71
atcttgaatg ctgctgttca tcatatacct ttgaggaaac tgtagtaaat tgatgattgg 60
ataagactca gatgaaccaa c 81

<210> SEQ ID NO 72
<211> LENGTH: 81
<212> TYPE: DNA
<213> ORGANISM: Artificial Sequence
<220> FEATURE:
<223> OTHER INFORMATION: Amplicon

<400> SEQUENCE: 72
atcttgaatg ctgctgttca tcatatacct ttgaggaaat tgtagtaaat tgatgattgg 60
ataagactca gatgaaccaa c 81

<210> SEQ ID NO 73
<211> LENGTH: 22
<212> TYPE: DNA
<213> ORGANISM: Artificial Sequence
<220> FEATURE:
<223> OTHER INFORMATION: Primer

<400> SEQUENCE: 73
ttcacttgca aaacattgaa ca 22

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
aaggaatcct cccaccaaat 20

<210> SEQ ID NO 75
<211> LENGTH: 18
<212> TYPE: DNA
<213> ORGANISM: Artificial Sequence
<220> FEATURE:
<223> OTHER INFORMATION: Probe

<400> SEQUENCE: 75
acgatgttac ataccgga 18

<210> SEQ ID NO 76
<211> LENGTH: 15
<212> TYPE: DNA
<213> ORGANISM: Artificial Sequence
<220> FEATURE:
<223> OTHER INFORMATION: Probe

<400> SEQUENCE: 76
ttacatcccg gaagc 15

<210> SEQ ID NO 77
<211> LENGTH: 408
<212> TYPE: DNA
<213> ORGANISM: Artificial Sequence
<220> FEATURE:
<223> OTHER INFORMATION: Consensus Reference Sequence

<400> SEQUENCE: 77
acatggcctc tragatgact ctggcatgct gtctacctrg aggaacaatg acaataatag 60
agattgttgc aaatggagag gcattcaatg caaygatgaa actggtcacg tacaagtact 120
caatcttcat tgtccagata gacattattt gacaggtgca atmaatctca cttcattgat 180
tcacttgcaa aacattgaac atctgatctc agcaataatg attttttacg atgttacatc 240
ccggaagcca tgggctcctt caccaactta agatatctca atctctcrta ttctgtattt 300
ggtgggagga ttccttctaa acttggaaat ctttcgcaac tacgatatct agaactcggg 360
ggaaatcatc tttgaggagc aattcctttt cagatgggga atctcatg 408

<210> SEQ ID NO 78
<211> LENGTH: 408
<212> TYPE: DNA
<213> ORGANISM: Artificial Sequence
<220> FEATURE:
<223> OTHER INFORMATION: Consensus Reference Sequence

<400> SEQUENCE: 78
acatggcctc tragatgact ctggcatgct gtctacctrg aggaacaatg acaataatag 60
agattgttgc aaatggagag gcattcaatg caaygatgaa actggtcacg tacaagtact 120

-continued

```
caatcttcat tgtccagata gacattattt gacaggtgca atmaatctca cttcattgat    180

tcacttgcaa aacattgaac atctgatctc agcaataatg atttttttacg atgttacata    240

ccggaagcca tgggctcctt caccaactta agatatctca atctctcrta ttctgtattt    300

ggtgggagga ttccttctaa acttggaaat ctttcgcaac tacgatatct agaactcggg    360

ggaaatcatc tttgaggagc aattcctttt cagatgggga atctcatg                408


<210> SEQ ID NO 79
<211> LENGTH: 137
<212> TYPE: DNA
<213> ORGANISM: Artificial Sequence
<220> FEATURE:
<223> OTHER INFORMATION: Amplicon

<400> SEQUENCE: 79

ttcacttgca aaacattgaa catctgatct cagcaataat gattttttac gatgttacat     60

cccggaagcc atgggctcct tcaccaactt aagatatctc aatctctcrt attctgtatt    120

tggtgggagg attcctt                                                   137


<210> SEQ ID NO 80
<211> LENGTH: 137
<212> TYPE: DNA
<213> ORGANISM: Artificial Sequence
<220> FEATURE:
<223> OTHER INFORMATION: Amplicon

<400> SEQUENCE: 80

ttcacttgca aaacattgaa catctgatct cagcaataat gattttttac gatgttacat     60

accggaagcc atgggctcct tcaccaactt aagatatctc aatctctcrt attctgtatt    120

tggtgggagg attcctt                                                   137
```

GENETIC LOCI ASSOCIATED WITH FROGEYE LEAF SPOT RESISTANCE AND BROWN STEM ROT RESISTANCE AND METHODS OF USE

FIELD OF THE INVENTION

This invention relates to methods of identifying and/or selecting soybean plants or germplasm that display improved resistance to Frogeye Leaf Spot and/or Brown Stem Rot in soybean.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 428801seqlist.txt, a creation date of Mar. 14, 2013 and a size of 26 KB. The sequence listing filed via EFS-Web is part of the specification and is hereby incorporated in its entirety by reference herein.

BACKGROUND

Soybeans (*Glycine max* L. Merr.) are a major cash crop and investment commodity in North America and elsewhere. Soybean oil is one of the most widely used edible oils, and soybeans are used worldwide both in animal feed and in human food production. Additionally, soybean utilization is expanding to industrial, manufacturing, and pharmaceutical applications.

Molecular markers have been used to selectively improve soybean crops through the use of marker assisted selection. Any detectible polymorphic trait can be used as a marker so long as it is inherited differentially and exhibits linkage disequilibrium with a phenotypic trait of interest. A number of soybean markers have been mapped and linkage groups created, as described in Cregan, P. B., et al., "An Integrated Genetic Linkage Map of the Soybean Genome" (1999) Crop Science 39:1464-90, and more recently in Choi, et al., "A Soybean Transcript Map: Gene Distribution, Haplotype and Single-Nucleotide Polymorphism Analysis" (2007) Genetics 176:685-96. Many soybean markers are publicly available at the USDA affiliated soybase website (soybase.org).

Most plant traits of agronomic importance are polygenic, otherwise known as quantitative, traits. A quantitative trait is controlled by several genes located at various locations, or loci, in the plant's genome. The multiple genes have a cumulative effect which contributes to the continuous range of phenotypes observed in many plant traits. These genes are referred to as quantitative trait loci (QTL). Recombination frequency measures the extent to which a molecular marker is linked with a QTL. Lower recombination frequencies, typically measured in centiMorgans (cM), indicate greater linkage between the QTL and the molecular marker. The extent to which two features are linked is often referred to as the genetic distance. The genetic distance is also typically related to the physical distance between the marker and the QTL; however, certain biological phenomenon (including recombinational "hot spots") can affect the relationship between physical distance and genetic distance. Generally, the usefulness of a molecular marker is determined by the genetic and physical distance between the marker and the selectable trait of interest.

In some cases, multiple closely linked markers, such as Single Nucleotide Polymorphism (SNP) markers, can be found to exist in a certain region of a plant genome encompassing one or more QTL. In such cases, by determining the allele present at each of those marker loci, a haplotype for that region of the plant genome can be determined. Further, by determining alleles or haplotypes present at multiple regions of the plant genome related to the same phenotypic trait, a marker profile for that trait can be determined. Such haplotype and marker profile information can be useful in identifying and selecting plants with certain desired traits.

Brown Stem Rot (BSR) of soybean [*Glycine max* (L.) Merrill] is caused by the fungal pathogen *Phialophora gregata*. Brown stem rot is widespread in Canada and in the Midwest and southeast United States. Yield losses up to 25% may occur primarily through the reduction in number and size of seeds. Frogeye Leaf Spot (FEY) is caused by *Cercospora sojina* and also threatens soybean production and can substantially reduce yields. Molecular characterization of both BSR and FEY would have important implications for soybean cultivar improvement.

There remains a need for soybean plants with improved resistance to Brown Stem Rot and/or Frogeye Leaf Spot and methods for identifying and selecting such plants.

SUMMARY

Various methods and compositions are provided for identifying and/or selecting soybean plants or soybean germplasm with improved resistance to Frogeye Leaf Spot (FEY) and/or Brown Stem Rot (BSR). In certain embodiments, the method comprises detecting at least one marker locus that is associated with resistance to Frogeye Leaf Spot and/or Brown Stem Rot. In other embodiments, the method further comprises detecting at least one marker profile or haplotype associated with resistance to Frogeye Leaf Spot and/or Brown Stem Rot. In further embodiments, the method comprises crossing a selected soybean plant with a second soybean plant. Further provided are markers, primers, probes and kits useful for identifying and/or selecting soybean plants or soybean germplasm with improved resistance to Frogeye Leaf Spot and/or Brown Stem Rot.

BRIEF DESCRIPTION OF THE FIGURES

FIG. 2 provides a visualization of the linkage and recombination for the Recombinant BSR isolines in Combination with Rcs3.

FIG. 3 provides a list of markers in linkage group J_(16) between genetic map position 2.34 to 88.93 of soybean.

DETAILED DESCRIPTION

Figure 1:
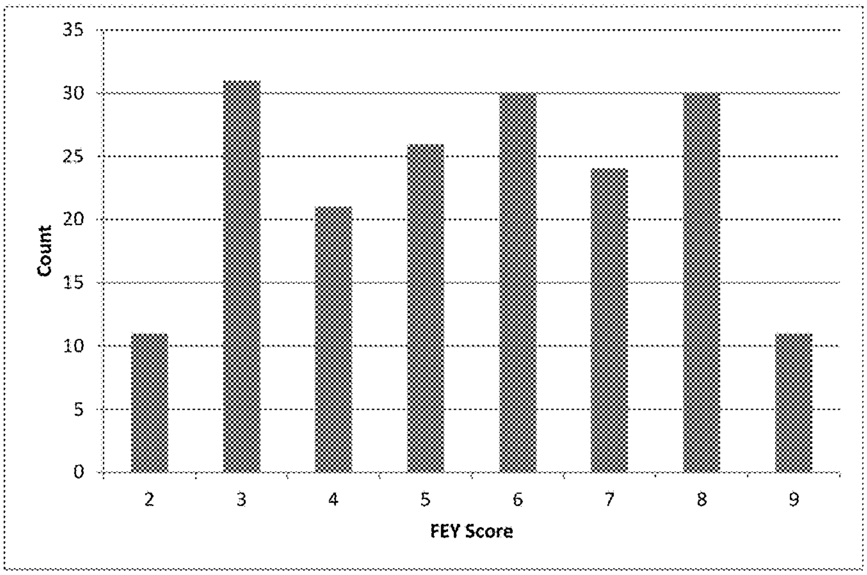
FIG. 1 shows the phenotypic distribution of marker S06363-1 among 184 progeny in the RIL mapping population are shown in FIG. 1.

Before describing the present invention in detail, it is to be understood that this invention is not limited to particular embodiments, which can, of course, vary. It is also to be understood that the terminology used herein is for the purpose of describing particular embodiments only, and is not intended to be limiting.

Certain definitions used in the specification and claims are provided below. In order to provide a clear and consistent understanding of the specification and claims, including the scope to be given such terms, the following definitions are provided:

As used in this specification and the appended claims, terms in the singular and the singular forms “a,” “an,” and “the,” for example, include plural referents unless the content clearly dictates otherwise. Thus, for example, reference to “plant,” “the plant,” or “a plant” also includes a plurality of plants; also, depending on the context, use of the term “plant” can also include genetically similar or identical progeny of that plant; use of the term “a nucleic acid” optionally includes, as a practical matter, many copies of that nucleic acid molecule; similarly, the term “probe” optionally (and typically) encompasses many similar or identical probe molecules.

Additionally, as used herein, “comprising” is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term “comprising” is intended to include examples encompassed by the terms “consisting essentially of” and “consisting of.” Similarly, the term “consisting essentially of” is intended to include examples encompassed by the term “consisting of.”

“Agronomics,” “agronomic traits,” and “agronomic performance” refer to the traits (and underlying genetic elements) of a given plant variety that contribute to yield over the course of a growing season. Individual agronomic traits include emergence vigor, vegetative vigor, stress resistance, disease resistance or resistance, insect resistance or resistance, herbicide resistance, branching, flowering, seed set, seed size, seed density, standability, threshability, and the like.

“Allele” means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term “amplifying” in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods, such as the ligase chain reaction (LCR), and RNA polymerase based amplification (e.g., by transcription) methods. An “amplicon” is an amplified nucleic acid, e.g., a nucleic acid that is produced by amplifying a template nucleic acid by any available amplification method (e.g., PCR, LCR, transcription, or the like).

An “ancestral line” is a parent line used as a source of genes, e.g., for the development of elite lines.

An “ancestral population” is a group of ancestors that have contributed the bulk of the genetic variation that was used to develop elite lines.

“Backcrossing” is a process in which a breeder crosses a progeny variety back to one of the parental genotypes one or more times.

The term “chromosome segment” designates a contiguous linear span of genomic DNA that resides in planta on a single chromosome.

“Cultivar” and “variety” are used synonymously and mean a group of plants within a species (e.g., *Glycine max*) that share certain genetic traits that separate them from other possible varieties within that species. Soybean cultivars are typically inbred lines produced after several generations of self-pollinations, however hybrid varieties may also be produced. Both inbred or hybrid varieties may be developing in a breeding program using doubled haploid technology. Individuals within a soybean cultivar are homogeneous, nearly genetically identical, with most loci in the homozygous state.

An “elite line” is an agronomically superior line that has resulted from many cycles of breeding and selection for superior agronomic performance. Numerous elite lines are available and known to those of skill in the art of soybean breeding.

An “elite population” is an assortment of elite individuals or lines that can be used to represent the state of the art in terms of agronomically superior genotypes of a given crop species, such as soybean.

An “exotic soybean strain” or an “exotic soybean germplasm” is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A “genetic map” is a description of genetic linkage relationships among loci on one or more chromosomes (or linkage groups) within a given species, generally depicted in a diagrammatic or tabular form.

“Genotype” is a description of the allelic state at one or more loci.

“Germplasm” means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is “homozygous” if the individual has only one type of allele at a given locus (e.g., a diploid individual has a copy of the same allele at a locus for each of two homologous chromosomes). An individual is “heterozygous” if more than one allele type is present at a given locus (e.g., a diploid individual with one copy each of two different alleles). The term “homogeneity” indicates that members of a group have the same genotype at one or more specific loci. In contrast, the term “heterogeneity” is used to indicate that individuals within the group differ in genotype at one or more specific loci.

“Introgression” means the entry or introduction of a gene, QTL, haplotype, marker profile, trait, or trait locus from the genome of one plant into the genome of another plant.

The terms “label” or “detectable label” refer to a molecule capable of detection. A detectable label can also include a combination of a reporter and a quencher, such as are employed in FRET probes or TaqMan™ probes. The term “reporter” refers to a substance or a portion thereof which is capable of exhibiting a detectable signal, which signal can be suppressed by a quencher. The detectable signal of the reporter is, e.g., fluorescence in the detectable range. The term “quencher” refers to a substance or portion thereof which is capable of suppressing, reducing, inhibiting, etc., the detectable signal produced by the reporter. As used herein, the terms “quenching” and “fluorescence energy transfer” refer to the process whereby, when a reporter and a quencher are in close proximity, and the reporter is excited by an energy source, a substantial portion of the energy of the excited state non-radiatively transfers to the quencher where it either dissipates non-radiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, resistance, etc.).

"Linkage" refers to a phenomenon wherein alleles tend to segregate together more often than expected by chance if their transmission was independent. Genetic recombination occurs with an assumed random frequency over the entire genome. Genetic maps are constructed by measuring the frequency of recombination between pairs of traits or markers. Traits or markers are considered herein to be associated or linked if they generally co-segregate. A 1/100 probability of recombination per generation is defined as a map distance of 1.0 centiMorgan (1.0 cM). The genetic elements or genes located on a single chromosome segment are physically linked. Two loci can be located in close proximity such that recombination between homologous chromosome pairs does not occur between the two loci during meiosis with high frequency, e.g., such that loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centiMorgans (cM), e.g., about 49, 40, 30, 20, 10, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 5%, 4%, 3%, 2%, 1%, 0.75%, 0.5%, or 0.25% or less. "Closely linked" markers display a cross over frequency with a given marker of about 10% or less (the given marker is within about 10 cM of a closely linked marker). In specific embodiments, a closely linked marker is with 10 cM, 9 cM, 8 cM, 7 cM, 6 cM, 5 cM, 4 cM, 3 cM, 2 cM or 1 cM of any given marker disclosed herein. In further embodiments, a marker associated with one of the markers disclosed herein can be within 75 Kb, 60 Kb, 50 Kb, 40 Kb, 30 Kb, 20K, 10 Kb, 5 Kb or less of the disclosed marker. Put another way, closely linked loci co-segregate at least about 90% of the time. Genetic linkage as evaluated by recombination frequency is impacted by the chromatin structure of the region comprising the loci. Typically, the region is assumed to have a euchromatin structure during initial evaluations. However, some regions, such are regions closer to centrosomes, have a heterochromatin structure. Without further information, the predicted physical distance between genetic map positions is based on the assumption that the region is euchromatic, however if the region comprises heterochromatin the markers may be physically closer together. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 2 Kb, about 1 Kb, about 500 nucleotides, about 250 nucleotides, or less.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

"Linkage disequilibrium" or "LD" is a non-random association of alleles at two or more loci and can occur between unlinked markers. It is based on allele frequencies within a population and is influenced by but not dependent on linkage.

"Linkage group" (LG) refers to traits or markers that generally co-segregate. A linkage group generally corresponds to a chromosomal region containing genetic material that encodes the traits or markers.

"Locus" is a defined segment of DNA.

A "map location" or "map position" is an assigned location on a genetic map relative to linked genetic markers where a specified marker can be found within a given species. Map positions are generally provided in centimorgans. A "physical position" or "physical location" or "physical map location" is the position, typically in nucleotides bases, of a particular nucleotide, such as a SNP nucleotide, on a chromosome.

"Mapping" is the process of defining the linkage relationships of loci through the use of genetic markers, populations segregating for the markers, and standard genetic principles of recombination frequency.

"Marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of soybean markers have been mapped and linkage groups created, as described in Cregan, P. B., et al., "An Integrated Genetic Linkage Map of the Soybean Genome" (1999) Crop Science 39:1464-90, and more recently in Choi, et al., "A Soybean Transcript Map: Gene Distribution, Haplotype and Single-Nucleotide Polymorphism Analysis" (2007) Genetics 176:685-96, and Hyten, et al. "A High Density Integrated Genetic Linkage Map of Soybean and the Development of a 1536 Universal Soy Linkage Panel for Quantitative Trait Locus Mapping" (2010) Crop Science 50:960-968. Many soybean markers are publicly available at the USDA affiliated soybase website (soybase.org). All markers are used to define a specific locus on the soybean genome. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in soybeans. "Marker assisted selection" refers to the process of selecting a desired trait or traits in a plant or plants by detecting one or more nucleic acids from the plant, where the nucleic acid is linked to the desired trait, and then selecting the plant or germplasm possessing those one or more nucleic acids.

"Haplotype" refers to a combination of particular alleles present within a particular plant's genome at two or more linked marker loci, for instance at two or more loci on a particular linkage group. For instance, in one example, two specific marker loci on Lg_(16) are used to define a haplotype for a particular plant. In still further examples, 3, 4, 5, 6, 7, 8, 9, 10, 11, 12, 13, 14, 15, 16, 17, 18, 19, 20, or more linked marker loci are used to define a haplotype for a particular plant.

In certain examples, multiple marker loci or haplotypes are used to define a "marker profile". As used herein, "marker profile" means the combination of two or more marker loci or haplotypes within a particular plant's genome. For instance, in one example, a particular combination of marker loci or a particular combination of haplotypes define the marker profile of a particular plant.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells and the like.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid," "nucleic acid molecule," "nucleic acid sequence," "nucleic acid fragment," and "oligonucleotide" are used interchangeably herein. These terms encompass nucleotide sequences and the like. A polynucleotide is a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide (synthetic or occurring naturally) that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Resistance and "improved resistance" are used interchangeably herein and refer to any type of increase in resistance or resistance to, or any type of decrease in susceptibility. A "resistant plant" or "resistant plant variety" need not possess absolute or complete resistance. Instead, a "resistant plant," "resistant plant variety," or a plant or plant variety with "improved resistance" will have a level of resistance or resistance which is higher than that of a comparable susceptible plant or variety.

"Self-crossing" or "self-pollination" or "selfing" is a process through which a breeder crosses a plant with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. Yield is the final culmination of all agronomic traits.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the invention or biologically active portion thereof is recombinantly produced, optimally culture medium represents less than about 30%, 20%, 10%, 5%, or 1% (by dry weight) of chemical precursors or non-protein-of-interest chemicals.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Methods are provided for identifying and/or selecting a soybean plant or soybean germplasm that displays improved resistance to Frogeye Leaf Spot (FEY) and/or Brown Stem Rot (BSR). The method comprises detecting in the soybean plant or germplasm, or a part thereof, at least one marker locus and/or a haplotype associated with resistance to FEY and/or BSR. Also provided are isolated polynucleotides and kits for use in identifying and/or detecting a soybean plant or soybean germplasm that displays improved resistance to FEY and/or BSR. Further provided are methods and compositions for breeding a soybean plant or a soybean germplasm that displays improved resistance to FEY, improved resistance to BSR, or improved resistance to FEY and BSR.

These findings have important implications for soybean production, as identifying markers that can be used for selection of FEY resistance and/or BSR resistance will greatly expedite the development of such resistances into elite cultivars.

Marker loci, haplotypes and marker profiles associated with resistance to Frogeye Leaf Spot are provided. Further provided are genomic loci that are associated with improved soybean resistance to FEY.

In certain embodiments, soybean plants or germplasm are identified that have at least one favorable allele, marker locus, haplotype or marker profile that positively correlates with resistance or improved resistance to FEY. However, in other embodiments, it is useful for exclusionary purposes during breeding to identify alleles, marker loci, haplotypes, or marker profiles that negatively correlate with resistance, for example, to eliminate such plants or germplasm from subsequent rounds of breeding.

In one embodiment, marker loci useful for identifying a first soybean plant or first soybean germplasm that displays improved resistance to FEY comprises S06363-1, S14236-1, S00005-01 and/or a marker closely linked thereto. See Table 1. Non-limiting examples of marker loci located within, linked to, or closely linked to these genomic loci are provided in FIG. 3.

TABLE 1

Marker Positions For Marker Loci Associated With Resistance to Frogeye Leaf Spot.

| Marker Name | Locus Name | Linkage Group | SNP name | Flanking Markers* | Public Map Marker Position (estimated)* | Marker Physical Map Position* | Allele (R/S) |
|---|---|---|---|---|---|---|---|
| S00005-01-A | S00005-01 | J_(16) | Gm16:33387556; Gm16:33387560 | BARC-024115-04764 and BARC-040393-07727 | 73.19 | 33387556 and 33387560 | T, C/A, T |
| S06363-1-Q1 | S06363-1 | J_(16) | Gm16:33328806 | BARC-024115-04764 and BARC-040393-07727 | 73.01 | 33,328,806 | C/T |
| S14236-1-Q3 | S14236-1 | J_(16) | Gm16:33368242 | BARC-024115-04764 and BARC-040393-07727 | 73.13 | 33,368,242 | G/A |

*Gm composite Genetic Map (Hyten et al. (2010) Crop Sci. 50: 960-968)

Markers, primers, haplotypes, and marker profiles, and methods of their use for identifying and/or selecting soybean plants with improved FEY resistance are provided. The method for determining the presence/absence/allele of a particular marker associated with soybean FEY resistance and within or linked to an interval in soybean plant or germplasm, and in turn determining the FEY haplotype or the Rcs3 haplotype and/or marker profile of the plant/germplasm, comprises analyzing genomic DNA from a soybean plant or germplasm to determine if at least one, or a plurality, of such markers is present or absent and in what allelic form. Using this information regarding the FEY-associated markers present in the particular plant or germplasm in turn allows a FEY haplotype and/or an Rcs3 haplotype to be assigned to that plant/germplasm. If multiple FEY haplotypes or Rcs3 haplotypes are deduced for a plant, a marker profile can in turn be assigned by combining all of these FEY haplotypes or Rcs3 haplotypes.

In certain examples, plants or germplasm are identified that have at least one favorable allele, haplotype, or marker profile that positively correlates with resistance or improved resistance. However, in other examples, it is useful for exclusionary purposes during breeding to identify alleles, haplotypes, or marker profiles that negatively correlate with resistance, for example to eliminate such plants or germplasm from subsequent rounds of breeding.

Marker loci are especially useful when they are closely linked to S00005-01, S06363-1, or S14236-1. Thus, in one example, marker loci display an inter-locus cross-over frequency of about 10% or less, about 9% or less, about 8% or less, about 7% or less, about 6% or less, about 5% or less, about 4% or less, about 3% or less, about 2% or less, about 1% or less, about 0.75% or less, about 0.5% or less, or about 0.25% or less to any one of S00005-01, S06363-1, or S14236-1 could be used. Thus, the loci are separated from any one of S00005-01, S06363-1, or S14236-1 by about 10 cM, 9 cM, 8 cM, 7 cM, 6 cM, 5 cM, 4 cM, 3 cM, 2 cM, 1 cM, 0.75 cM, 0.5 cM, or 0.25 cM or less.

In certain examples, multiple marker loci that collectively make up the FEY haplotype of interest are investigated, for instance 2, 3, 4, 5, 6, 7, 8, 9, 10, 11, 12, 13, 14, 15, 16, 17, 18, 19, 20, 21, 22, 23, 24, 25, 26, 27, 28, 29, 30, or more marker loci.

In certain examples, markers useful for defining a FEY haplotype or the Rsc3 haplotype are linked or are closely linked to the interval flanked by and including the marker loci BARC-032663-09006 and Satt431 in the Soybase database (soybase.org). See FIG. 3.

Markers within, linked to, or closely linked to these intervals are illustrated in the genetic map of FIG. 3. Numerous such markers are also well known in the art, and for example, are described in the USDA's soybase database, available at soybase.org, and Hyten et al. (2010) Crop Sci. 50:960-968.

Exemplary markers useful for defining the FEY haplotype or the Rcs3 haplotype are provided in Table 1. Tables 5, 6, 7 and 8 provide the target regions containing the markers, as well as primers and probes that can be used to amplify and detect the markers. In certain examples the marker loci used to define the FEY haplotype or the Rcs3 haplotype are one or more of S06363-1, S14236-1, S00005-01 and/or a marker closely linked thereto. In other examples, the marker loci used to define the FEY haplotype or the Rcs3 haplotype are two or more of S06363-1, S14236-1, S00005-01 and/or a marker closely linked thereto. In further examples, the marker loci used to define the FEY haplotype are each of S06363-1, S14236-1, S00005-01 and/or a marker closely linked thereto. Table 2 provides non-limiting examples of FEY haplotypes and also marker combinations for the Rcs3 haplotype type which also displays increased resistance to FEY.

TABLE 2

Non-limiting examples of marker combinations for selected Frogeye Leaf Spot resistance haplotypes. Table denotes various marker combinations and the allele call for the given haplotype.

| | Marker name | | |
|---|---|---|---|
| Phenotype | S00005-01 | S06363-1 | S14236-1 |
| FEY | T, C | C | G |
| | T, C | | |
| | | C | |
| | | C | G |
| | | | G |
| | T, C | | G |
| | T, C | C | |
| Rcs3 | T, C | | G |
| | T, C | | |
| | | | G |

In one embodiment, the method of identifying a first soybean plant or a first soybean germplasm that displays improved resistance to FEY comprises detecting in the genome of the first soybean plant or in the genome of the first soybean germplasm at least one haplotype that is associated with the resistance, wherein the at least one haplotype comprises at least two of the various marker loci provided herein or any maker combination as set forth in Table 2. Not only can one detect the various markers provided herein, it is recognized that one could detect any markers that are closely linked to the various markers discussed herein.

In addition to the markers discussed herein, information regarding useful soybean markers can be found, for example, on the USDA's Soybase website, available at soybase.org. One of skill in the art will recognize that the identification of favorable marker alleles may be germplasm-specific. The determination of which marker alleles correlate with resistance (or susceptibility) is determined for the particular germplasm under study. One of skill will also recognize that methods for identifying the favorable alleles are routine and well known in the art, and furthermore, that the identification and use of such favorable alleles is well within the scope of the invention.

Marker loci, haplotypes and marker profiles associated with resistance to FEY are provided. Further provided are genomic loci that are associated with soybean resistance to FEY.

In one embodiment, the method of identifying a first soybean plant or a first soybean germplasm that displays improved resistance to FEY comprises detecting in the genome of the first soybean plant or in the genome of the first soybean germplasm at least one marker locus that (A) can be interval flanked by and including the marker loci BARC-024115-04764 and BARC-040393-07727 on linkage group linkage Group J_(16); (B) can comprise one or more of S06363-1, S14236-1, S00005-01 and/or a marker closely linked thereto on linkage group J_(16); (C) can comprise a haplotype of marker loci on linkage group J_(16) comprising a T or C allele at S00005-01 and a G allele at S14236-1; (D) can comprise a haplotype of marker loci on linkage group J_(16) comprising a C allele at S06363-1 and a T or C allele at S00005-01; (E) can comprise a haplotype of marker loci on linkage group J_(16) comprising a C allele at S06363-1 and a G allele at S14236-1; and/or, (F) can comprise a haplotype of marker loci on linkage group J_(16) comprising a C allele at S06363-1, a G allele at S14236-1, and a T or a C allele at S00005-01.

IV. Genomic Loci, Marker Loci, and Haplotypes Associated with Resistance to Brown Stem Rot Marker loci, haplotypes and marker profiles associated with resistance to Brown Stem Rot (BSR) are provided. Further provided are genomic loci that are associated with improved soybean resistance to BSR.

In certain embodiments, soybean plants or germplasm are identified that have at least one favorable allele, marker locus, haplotype or marker profile that positively correlates with resistance or improved resistance to BSR. However, in other embodiments, it is useful for exclusionary purposes during breeding to identify alleles, marker loci, haplotypes, or marker profiles that negatively correlate with resistance, for example, to eliminate such plants or germplasm from subsequent rounds of breeding.

In one embodiment, marker loci useful for identifying a first soybean plant or first soybean germplasm that displays improved resistance to BSR comprises S01584-1, S04831-1, S16015-001, S07157-1, S07157-2, S04857-1, and/or S16023-001. See Table 3. Non-limiting examples of marker loci located within, linked to, or closely linked to these genomic loci are provided in FIG. 3.

instance 2, 3, 4, 5, 6, 7, 8, 9, 10, 11, 12, 13, 14, 15, 16, 17, 18, 19, 20, 21, 22, 23, 24, 25, 26, 27, 28, 29, 30, or more marker loci.

TABLE 3

Marker Positions For Marker Loci Associated With Resistance to Brown Stem Rot.

| Marker Name | Marker Locus name | Linkage Group (ch) | SNP name | Flanking Public Markers* | Genetic Map Marker Position (estimated)* | Marker Physical Map Position* |
|---|---|---|---|---|---|---|
| S01584-1-Q5 | S01584-1 | J_(16) | Gm16:32308049 | BARC-010297-00580 and BARC-017835-02393 | 70.73 | 32,308,049 |
| S04831-1-Q2 | S04831-1 | J_(16) | Gm16:32352386 | BARC-010297-00580 and BARC-017835-02393 | 70.85 | 32,352,386 |
| S04857-1-A | S04857-1 | J_(16) | | BARC-010297-00580 and BARC-017835-02393 | 70.73 | 32,308,250 |
| S07157-1-Q1 | S07157-1 | J_(16) | Gm16:33636569 | Satt547and BARC-028589-05965 | 75.28 | 33,636,569 |
| S07157-2-Q1 | S07157-2 | J_(16) | Gm16:33636572 | Satt547and BARC-028589-05965 | 75.28 | 33,636,572 |
| S16015-001-Q001 | S16015-001 | J_(16) | Gm16:33564749 | Satt547and BARC-028589-05965 | 75.00 | 33,564,749 |
| S16023-001-Q002 | S16023-001 | J_(16) | Gm16:33636969 | Satt547and BARC-028589-05965 | 75.29 | 33,636,969 |

*Gm composite Genetic Map (Hyten et al. (2010) *Crop Sci* 50: 960-968.)

Markers, primers, haplotypes, and marker profiles, and methods of their use for identifying and/or selecting soybean plants with improved BSR resistance are provided. The method for determining the presence/absence/allele of a particular marker associated with soybean BSR resistance and within or linked to an interval in soybean plant or germplasm, and in turn determining the BSR haplotype and/or marker profile of the plant/germplasm, comprises analyzing genomic DNA from a soybean plant or germplasm to determine if at least one, or a plurality, of such markers is present or absent and in what allelic form. Using this information regarding the BSR-associated markers present in the particular plant or germplasm in turn allows a BSR haplotype to be assigned to that plant/germplasm. If multiple BSR haplotypes are deduced for a plant, a marker profile can in turn be assigned by combining all of these BSR haplotypes.

In certain examples, plants or germplasm are identified that have at least one favorable allele, haplotype, or marker profile that positively correlates with resistance or improved resistance. However, in other examples, it is useful for exclusionary purposes during breeding to identify alleles, haplotypes, or marker profiles that negatively correlate with resistance, for example to eliminate such plants or germplasm from subsequent rounds of breeding.

Marker loci are especially useful when they are closely linked to S01584-1, S04831-1, S16015-001, S07157-1, S07157-2, S04857-1, and/or S16023-001. Thus, in one example, marker loci display an inter-locus cross-over frequency of about 10% or less, about 9% or less, about 8% or less, about 7% or less, about 6% or less, about 5% or less, about 4% or less, about 3% or less, about 2% or less, about 1% or less, about 0.75% or less, about 0.5% or less, or about 0.25% or less to any one of S01584-1, S04857-1, S04831-1, S16015-001, S07157-1, S07157-2, and/or S16023-001 could be used. Thus, the loci are separated from any one of S01584-1, S04831-1, S04857-1, S16015-001, S07157-1, S07157-2, and/or S16023-001 by about 10 cM, 9 cM, 8 cM, 7 cM, 6 cM, 5 cM, 4 cM, 3 cM, 2 cM, 1 cM, 0.75 cM, 0.5 cM, or 0.25 cM or less.

In certain examples, multiple marker loci that collectively make up the BSR haplotype of interest are investigated, for In certain examples, markers useful for defining a BSR haplotype are linked or are closely linked to the interval flanked by and including the marker loci BARC-042193-08207 and BARC-011625-00310 in the Soybase database (soybase.org).

Markers within, linked to, or closely linked to these intervals are illustrated in the genetic map of FIG. 3. Numerous such markers are also well known in the art, for example, are described in the USDA's soybase database, available at soybase.org.

Exemplary markers useful for defining BSR haplotypes are provided in Table 4. Tables 9, 10, 11 and 12 provide the target regions containing the markers, as well as primers and probes that can be used to amplify and detect the markers. In certain examples the marker loci used to define the BSR haplotype are one or more of S01584-1, S04831-1, S16015-001, S07157-1, S04857-1, S07157-2, and/or S16023-001 and/or a marker closely linked thereto. In other examples, the marker loci used to define the BSR haplotype are two or more of S04857-1, S01584-1, S04831-1, S16015-001, S07157-1, S07157-2, and/or S16023-001 and/or a marker closely linked thereto. In other examples, the marker loci used to define the BSR haplotype are three or more of S04857-1, S01584-1, S04831-1, S16015-001, S07157-1, S07157-2, and/or S16023-001 and/or a marker closely linked thereto. In other examples, the marker loci used to define the BSR haplotype are four or more of S04857-1, S01584-1, S04831-1, S16015-001, S07157-1, S07157-2, and/or S16023-001 and/or a marker closely linked thereto. In other examples, the marker loci used to define the BSR haplotype are five or more of S04857-1, S01584-1, S04831-1, S16015-001, S07157-1, S07157-2, and/or S16023-001 and/or a marker closely linked thereto. In other examples, the marker loci used to define the BSR haplotype are six or more of S04857-1, S01584-1, S04831-1, S16015-001, S07157-1, S07157-2, and/or S16023-001 and/or a marker closely linked thereto. In further examples, the marker loci used to define the BSR haplotype are each of S04857-1, S01584-1, S04831-1, S16015-001, S07157-1, S07157-2, and/or S16023-001 and/or a marker closely linked thereto.

TABLE 4

Non-limiting examples of marker combinations for selected Brown Stem Rot resistance haplotypes alone or in combination with Frogeye Leaf Spot haplotypes. Table denotes various marker combinations and the allele call for the given haplotype.

| | Marker name | | | | | | | |
|---|---|---|---|---|---|---|---|---|
| Phenotype | S01584-1 | S04831-1 | S04857-1 | S07157-1 | S16015-1 | S14236-1 | S07157-2 | S16023-1 |
| Rbs3a | | A | | | | | | |
| | G | | | | | | | |
| | | | C | | | | | |
| | | | | T | | | | |
| | | | | | C | | | |
| | | A | | T | | | | |
| | | A | | | C | | | |
| | G | | | T | | | | |
| | G | | | | C | | | |
| | | | C | T | | | | |
| | | | C | | C | | | |
| | G | A | | T | | | | |
| | G | A | | | C | | | |
| | G | | C | T | | | | |
| | G | | C | | C | | | |
| | G | A | | T | C | | G | T |
| Rbs3a Hidden | | A | | | | | | |
| | G | | | | | | | |
| | | | C | | | | | |
| | | A | | C | | | | |
| | | A | | | T | | | |
| | G | | | C | | | | |
| | G | | | | T | | | |
| | | | C | C | | | | |
| | | | C | | T | | | |
| | G | A | | C | | | | |
| | G | A | | | T | | | |
| | G | | C | C | | | | |
| | G | | C | | T | | | |
| | G | A | | | | | | |
| | G | A | | C | T | | G | T |
| Rbs3b w/ Rcs3 | G | | | | | | | |
| | | | | | | G | | |
| | | | | | | | A | |
| | | | | | | | | C |
| | G | | | | | | A | |
| | G | | | | | | | C |
| | G | | | | | G | | |
| | G | | | | | G | | C |
| | G | | | | | G | A | |
| | | | | | | G | A | |
| BSR tolerant (hidden Rbs3b) | G | | | | | | | |
| | | | C | | | | | |
| | G | | C | | | | | |
| | G | G | | | | | | |
| | | G | C | | | | | |
| | G | | | | | | G | |
| | G | | | | | | | T |
| | G | | | | | G | | |
| | G | G | | C | T | | G | T |

In one embodiment, the method of identifying a first soybean plant or a first soybean germplasm that displays improved resistance to BSR comprises detecting in the genome of the first soybean plant or in the genome of the first soybean germplasm at least one haplotype that is associated with the resistance, wherein the at least one haplotype comprises at least two of the various marker loci provided herein (i.e., S04857-1, S01584-1, S04831-1, S16015-001, S07157-1, S07157-2, and/or S16023-001 and/or a marker closely linked thereto) or any marker combination as set forth in Table 4. Not only can one detect the various markers provided herein, it is recognized that one could detect any markers that are closely linked to the various markers discussed herein.

In addition to the markers discussed herein, information regarding useful soybean markers can be found, for example, on the USDA's Soybase website, available at soybase.org, and Hyten et al. (2010) Crop Sci. 50:960-968. One of skill in the art will recognize that the identification of favorable marker alleles may be germplasm-specific. The determination of which marker alleles correlate with resistance (or susceptibility) is determined for the particular germplasm under study. One of skill will also recognize that methods for identifying the favorable alleles are routine and well known in the art, and furthermore, that the identification and use of such favorable alleles is well within the scope of the invention.

Marker loci, haplotypes and marker profiles associated with resistance to BSR are provided. Further provided are genomic loci that are associated with soybean resistance to BSR.

In one embodiment, the method of identifying a first soybean plant or a first soybean germplasm that displays improved resistance to BSR comprises detecting in the genome of the first soybean plant or in the genome of the first soybean germplasm at least one marker locus that: (a) can be interval flanked by and including the marker loci BARC-042193-08207 and BARC-011625-00310 on linkage group linkage Group J_(16); (b) can comprise one or more of S01584-1, S04857-1, S04831-1, S16015-001, S07157-1, S07157-2, and/or S16023-001 and/or a marker closely linked thereto on linkage group J_(16); (c) can comprise a Rbs3a haplotype of marker loci on linkage group J_(16) comprising one or more of the following: a G allele at S01584-1, an A allele at S04831-1, a C allele at S16015-001, a T allele at S07157-1, a G allele at S07157-2, a T allele at S16023-001, and/or a C allele at S04857-1; (d) can comprise a Rbs3a haplotype of marker loci on linkage group J_(16) comprising an A allele at S04831-1 and a T allele at S07157-1; (e) can comprise a Rbs3a haplotype of marker loci on linkage group J_(16) comprising a G allele at S01584-1 and a T allele at S07157-1; (f) can comprise a Rbs3a haplotype of marker loci on linkage group J_(16) comprising a C allele at S16015-1 and an A allele at S04831-1; (g) can comprise a Rbs3a haplotype of marker loci on linkage group J_(16) comprising G allele at S01584-1 and a C allele at S16015-1; (h) can comprise a Rbs3a haplotype of marker loci on linkage group J_(16) comprising a C allele at S04857-1 and a T allele at S07157-1; (i) can comprise a Rbs3a haplotype of marker loci on linkage group J_(16) comprising a C allele at S04857-1 and a C allele at S16015-1; (j) can comprise a Rbs3a haplotype of marker loci on linkage group J_(16) comprising a G allele at S01584-1, an A allele at S04831-1, and a T allele at S07157-1; (k) can comprise a Rbs3a haplotype of marker loci on linkage group J_(16) comprising a G allele at S01584-1, an A allele at S04831-1, and a C allele at S16015-1; (1) can comprise a Rbs3a haplotype of marker loci on linkage group J_(16) comprising a G allele at S01584-1, a C allele at S04857-1, and a T allele at S07157-1; (m) can comprise a Rbs3a haplotype of marker loci on linkage group J_(16) comprising a G allele at S01584-1, a C allele at S04857-1, and a C allele at S16015-1; (n) can comprise a Rbs3a haplotype of marker loci on linkage group J_(16) comprising a G allele at S01584-1, an A allele at S04831-1, a T allele at S07157-1, and a C allele at S16015-1; a G allele at S07157-2 and a T allele at S16023-1; (o) can comprise a Rbs3b haplotype of marker loci on linkage group J_(16) comprising one or more of the following: a G allele at S01584-1, a G allele at S04831-1, a T allele at S16015-001, a C allele at S07157-1, an A allele at S07157-2, a C allele at S16023-001, and/or a C allele at S04857-1; (p) can comprise a Rbs3a hidden haplotype of marker loci on linkage group J_(16) comprising one or more of the following: a G allele at S01584-1, an A allele at S04831-1, a T allele at S16015-001, a C allele at S07157-1, a G allele at S07157-2, a T allele at S16023-001, and/or a C allele at S04857-1; (q) can comprise a Rbs3a hidden haplotype of marker loci on linkage group J_(16) comprising an allele A at S04831-1 and a C allele at S07157-1; (r) can comprise a Rbs3a hidden haplotype of marker loci on linkage group J_(16) comprising an A allele at S04831-1 and a T allele at S16015-1; (s) can comprise a Rbs3a hidden haplotype of marker loci on linkage group J_(16) comprising a G allele at S01584-1 and a C allele at S07157-1; (t) can comprise a Rbs3a hidden haplotype of marker loci on linkage group J_(16) comprising a G allele at S01584-1 and a T allele at S16015-1; (u) can comprise a Rbs3a hidden haplotype of marker loci on linkage group J_(16) comprising a C allele at S04857-1 and a C allele at S07157-1; (v) can comprise a Rbs3a hidden haplotype of marker loci on linkage group J_(16) comprising a C allele at S04857-1 and a T allele at S16015-1; (w) can comprise a Rbs3a hidden haplotype of marker loci on linkage group J_(16) comprising a G allele at S01584-1, an A allele at S04831-1, and a C allele at S07157-1; (x) can comprise a Rbs3a hidden haplotype of marker loci on linkage group J_(16) comprising a G allele at S01584-1, an A allele at S04831-1, and a T allele at S16015-1; (y) can comprise a Rbs3a hidden haplotype of marker loci on linkage group J_(16) comprising a G allele at S01584-1, a C allele at S04857-1 and a C allele at S07157-1; (z) can comprise a Rbs3a hidden haplotype of marker loci on linkage group J_(16) comprising a G allele at S01584-1, a C allele at S04857-1, and a T allele at S16015-1; (aa) can comprise a Rbs3a hidden haplotype of marker loci on linkage group J_(16) comprising a G allele at S01584-1 and an A allele at S04831-1; (ab) can comprise a Rbs3a hidden haplotype of marker loci on linkage group J_(16) comprising a G allele at S01584-1, an A allele at S04831-1, a C allele at S07157-1, a T allele at S16015-1, a G allele at S07157-2 and a T allele at S16023-1; (ac) can comprise a Rbs3b hidden haplotype of marker loci on linkage group J_(16) comprising one or more of the following: a G allele at S01584-1, an A allele at S04831-1, a T allele at S16015-001, a C allele at S07157-1, a G allele at S07157-2, a T allele at S16023-001, and/or a C allele at S04857-1; (ad) can comprise a Rbs3b hidden haplotype of marker loci on linkage group J_(16) comprising a G allele at S01584-1 and a C allele at S04857-1; (ae) can comprise a Rbs3b hidden haplotype of marker loci on linkage group J_(16) comprising a G allele at S01584-1 and a G allele at S04831-1; (af) can comprise a Rbs3b hidden haplotype of marker loci on linkage group J_(16) comprising a G allele at S04831-1 and a C allele at S04857-1; (ag) can comprise a Rbs3b hidden haplotype of marker loci on linkage group J_(16) comprising a G allele at S01584-1 and a G allele at S07157-2; (ah) can comprise a Rbs3b hidden haplotype of marker loci on linkage group J_(16) comprising a G allele at S01584-1 and a T allele at S16023-1; (ai) can comprise a Rbs3b hidden haplotype of marker loci on linkage group J_(16) comprising a G allele at S01584-1 and a G allele at S14236-1; (aj) can comprise a Rbs3b hidden haplotype of marker loci on linkage group J_(16) comprising a G allele at S01584-1, a G allele at S04831-1, a C allele at S07157-1, a T allele at S16015-1, a G allele at S07157-2, and a T allele S16023-1; or any other combination set forth in Table 4.

Not only can one detect the various markers provided herein, it is recognized that one could detect any markers that are closely linked to the various markers discussed herein.

Various methods are provided to identify soybean plants and/or germplasm with improved resistance to BSR and/or FEY. In one embodiment, the method of identifying comprises detecting at least one marker locus associated with resistance to BSR and/or FEY. The term "associated with" in connection with a relationship between a marker locus and a phenotype refers to a statistically significant dependence of marker frequency with respect to a quantitative scale or qualitative gradation of the phenotype. Thus, an allele of a marker is associated with a trait of interest when the allele of the marker locus and the trait phenotypes are found together in the progeny of an organism more often than if the marker genotypes and trait phenotypes segregated separately.

Any combination of the marker loci provided herein can be used in the methods to identify a soybean plant or soybean germplasm that displays improved resistance to FEY. Any one marker locus or any combination of the markers set forth in Table 1 or 2 or any closely linked marker can be used to aid in identifying and selecting soybean plants or soybean germplasm with improved resistance to FEY.

In one embodiment, a method of identifying a first soybean plant or a first soybean germplasm that displays improved resistance to FEY is provided. The method comprises detecting in the genome of the first soybean plant or first soybean germplasm at least one marker locus that is associated with resistance. In such a method, the at least one marker locus: (A) can be interval flanked by and including the marker loci BARC-024115-04764 and BARC-040393-07727 on linkage group linkage Group J_(16); (B) can comprise one or more of S06363-1, S14236-1, S00005-01 and/or a marker closely linked thereto on linkage group J_(16); (C) can comprise a haplotype of marker loci on linkage group J_(16) comprising a T or C allele at S00005-01 and a G allele at S14236-1; (D) can comprise a haplotype of marker loci on linkage group J_(16) comprising a C allele at S06363-1 and a T or C allele at S00005-01; (E) can comprise a haplotype of marker loci on linkage group J_(16) comprising a C allele at S06363-1 and a G allele at S14236-1; and/or, (F) can comprise a haplotype of marker loci on linkage group J_(16) comprising a C allele at S06363-1, a G allele at S14236-1, and a T or a C allele at S00005-01.

Any combination of the marker loci provided herein can be used in the methods to identify a soybean plant or soybean germplasm that displays improved resistance to BSR. Any one marker locus or any combination of the markers set forth in Table 3 or 4 or any closely linked marker can be used to aid in identifying and selecting soybean plants or soybean germplasm with improved resistance to BSR.

In one embodiment, a method of identifying a first soybean plant or a first soybean germplasm that displays improved resistance to BSR is provided. The method comprises detecting in the genome of the first soybean plant or first soybean germplasm at least one marker locus that is associated with resistance. In such a method, the at least one marker locus: (a) can be interval flanked by and including the marker loci BARC-042193-08207 and BARC-011625-00310 on linkage group linkage Group J_(16); (b) can comprise one or more of S01584-1, S04857-1, S04831-1, S16015-001, S07157-1, S07157-2, and/or S16023-001 and/or a marker closely linked thereto on linkage group J_(16); (c) can comprise a Rbs3a haplotype of marker loci on linkage group J_(16) comprising one or more of the following: a G allele at S01584-1, an A allele at S04831-1, a C allele at S16015-001, a T allele at S07157-1, a G allele at S07157-2, a T allele at S16023-001, and/or a C allele at S04857-1; (d) can comprise a Rbs3a haplotype of marker loci on linkage group J_(16) comprising an A allele at S04831-1 and a T allele at S07157-1; (e) can comprise a Rbs3a haplotype of marker loci on linkage group J_(16) comprising a G allele at S01584-1 and a T allele at S07157-1; (f) can comprise a Rbs3a haplotype of marker loci on linkage group J_(16) comprising a C allele at S16015-1 and an A allele at S04831-1; (g) can comprise a Rbs3a haplotype of marker loci on linkage group J_(16) comprising G allele at S01584-1 and a C allele at S16015-1; (h) can comprise a Rbs3a haplotype of marker loci on linkage group J_(16) comprising a C allele at S04857-1 and a T allele at S07157-1; (i) can comprise a Rbs3a haplotype of marker loci on linkage group J_(16) comprising a C allele at S04857-1 and a C allele at S16015-1; (j) can comprise a Rbs3a haplotype of marker loci on linkage group J_(16) comprising a G allele at S01584-1, an A allele at S04831-1, and a T allele at S07157-1; (k) can comprise a Rbs3a haplotype of marker loci on linkage group J_(16) comprising a G allele at S01584-1, an A allele at S04831-1, and a C allele at S16015-1; (1) can comprise a Rbs3a haplotype of marker loci on linkage group J_(16) comprising a G allele at S01584-1, a C allele at S04857-1, and a T allele at S07157-1; (m) can comprise a Rbs3a haplotype of marker loci on linkage group J_(16) comprising a G allele at S01584-1, a C allele at S04857-1, and a C allele at S16015-1; (n) can comprise a Rbs3a haplotype of marker loci on linkage group J_(16) comprising a G allele at S01584-1, an A allele at S04831-1, a T allele at S07157-1, and a C allele at S16015-1; a G allele at S07157-2 and a T allele at S16023-1; (o) can comprise a Rbs3b haplotype of marker loci on linkage group J_(16) comprising one or more of the following: a G allele at S01584-1, a G allele at S04831-1, a T allele at S16015-001, a C allele at S07157-1, an A allele at S07157-2, a C allele at S16023-001, and/or a C allele at S04857-1; (p) can comprise a Rbs3a hidden haplotype of marker loci on linkage group J_(16) comprising one or more of the following: a G allele at S01584-1, an A allele at S04831-1, a T allele at S16015-001, a C allele at S07157-1, a G allele at S07157-2, a T allele at S16023-001, and/or a C allele at S04857-1; (q) can comprise a Rbs3a hidden haplotype of marker loci on linkage group J_(16) comprising an allele A at S04831-1 and a C allele at S07157-1; (r) can comprise a Rbs3a hidden haplotype of marker loci on linkage group J_(16) comprising an A allele at S04831-1 and a T allele at S16015-1; (s) can comprise a Rbs3a hidden haplotype of marker loci on linkage group J_(16) comprising a G allele at S01584-1 and a C allele at S07157-1; (t) can comprise a Rbs3a hidden haplotype of marker loci on linkage group J_(16) comprising a G allele at S01584-1 and a T allele at S16015-1; (u) can comprise a Rbs3a hidden haplotype of marker loci on linkage group J_(16) comprising a C allele at S04857-1 and a C allele at S07157-1; (v) can comprise a Rbs3a hidden haplotype of marker loci on linkage group J_(16) comprising a C allele at S04857-1 and a T allele at S16015-1; (w) can comprise a Rbs3a hidden haplotype of marker loci on linkage group J_(16) comprising a G allele at S01584-1, an A allele at S04831-1, and a C allele at S07157-1; (x) can comprise a Rbs3a hidden haplotype of marker loci on linkage group J_(16) comprising a G allele at S01584-1, an A allele at S04831-1, and a T allele at S16015-1; (y) can comprise a Rbs3a hidden haplotype of marker loci on linkage group J_(16) comprising a G allele at S01584-1, a C allele at S04857-1 and a C allele at S07157-1; (z) can comprise a Rbs3a hidden haplotype of marker loci on linkage group J_(16) comprising a G allele at S01584-1, a C allele at S04857-1, and a T allele at S16015-1; (aa) can comprise a Rbs3a hidden haplotype of marker loci on linkage group J_(16) comprising a G allele at S01584-1 and an A allele at S04831-1; (ab) can comprise a Rbs3a hidden haplotype of marker loci on linkage group J_(16) comprising a G allele at S01584-1, an A allele at S04831-1, a C allele at S07157-1, a T allele at S16015-1, a G allele at S07157-2 and a T allele at S16023-1; (ac) can comprise a Rbs3b hidden haplotype of marker loci on linkage group J_(16) comprising one or more of the following: a G allele at S01584-1, an A allele at S04831-1, a T allele at S16015-001, a C allele at S07157-1, a G allele at S07157-2, a T allele at S16023-001, and/or a C allele at S04857-1; (ad) can comprise a Rbs3b hidden haplotype of marker loci on linkage group J_(16) comprising a G allele at S01584-1 and a C allele at S04857-1; (ae) can comprise a Rbs3b hidden haplotype of marker loci on linkage group J_(16) comprising a G allele at S01584-1 and a G allele at S04831-1; (af) can comprise a Rbs3b hidden haplotype of marker loci on linkage group J_(16) comprising a G allele at S04831-1 and a C allele at S04857-1; (ag) can comprise a Rbs3b hidden haplotype of marker loci on linkage group J_(16) comprising a G allele at S01584-1 and a G allele at S07157-2; (ah) can comprise a Rbs3b hidden haplotype of marker loci on linkage group J_(16) comprising a G allele at S01584-1 and a T allele at S16023-1; (ai) can comprise a Rbs3b hidden haplotype of marker loci on linkage group J_(16) comprising a G allele at S01584-1 and a G allele at S14236-1; (aj) can comprise a Rbs3b hidden haplotype of marker loci on linkage group J_(16) comprising a G allele at S01584-1, a G allele at S04831-1, a C allele at S07157-1, a T allele at S16015-1, a G allele at S07157-2, and a T allele S16023-1; or any other combination set forth in Table 4.

In other embodiments, two or more marker loci are detected in the method. While in other embodiments, a method of identifying a first soybean plant or a first soybean germplasm that displays improved resistance to BSR and improved resistance to FEY is provided. Such methods can employ one or more marker locus associated with BSR in combination with one or more marker locus associated with FEY. In a specific embodiment, the germplasm is a soybean variety.

In other embodiments, the method further comprises crossing the selected first soybean plant or first soybean germplasm with a second soybean plant or second soybean germplasm. In a further embodiment of the method, the second soybean plant or second soybean germplasm comprises an exotic soybean strain or an elite soybean strain.

In specific embodiments, the first soybean plant or first soybean germplasm comprises a soybean variety. Any soybean line known to the art or disclosed herein may be used. Non-limiting examples of soybean varieties and their associated BSR and/or FEY resistance alleles encompassed by the methods provided herein.

In another embodiment, the detection method comprises amplifying at least one marker locus and detecting the resulting amplified marker amplicon. In such a method, amplifying comprises (a) admixing an amplification primer or amplification primer pair for each marker locus being amplified with a nucleic acid isolated from the first soybean plant or the first soybean germplasm such that the primer or primer pair is complementary or partially complementary to a variant or fragment of the genomic locus comprising the marker locus and is capable of initiating DNA polymerization by a DNA polymerase using the soybean nucleic acid as a template; and (b) extending the primer or primer pair in a DNA polymerization reaction comprising a DNA polymerase and a template nucleic acid to generate at least one amplicon. In such a method, the primer or primer pair can comprise a variant or fragment of one or more of the genomic loci provided herein.

Methods and compositions are further provided to stack robust BSR resistance with robust Frogeye Leaf Spot resistance. The genetic haplotype referred to herein as Rbs3a has a very high level of resistance to Brown Stem Rot. The genetic haplotype referred to herein as “Rbs3b” has moderate levels of resistance to Brown Stem Rot. Rbs3b (Brown Stem Rot resistance) and Rcs3 (Frogeye Leaf Spot resistance) are linked in coupling on Lg J and our data suggest these two genes are 3 cM apart.

Methods and compositions are provided to directly track the FEY resistance and use such markers to stack the FEY resistance with the Rbs3a haplotype. Thus, methods of breeding a soybean plant or a soybean germplasm that displays improved resistance to FEY and improved resistance to BSR are provided and comprises: (a) detecting in the genome of a first soybean plant or in the genome of the first soybean germplasm at least one marker locus that is associated with an improved resistance to FEY and selecting said first soybean plant or the first soybean germplasm having said marker locus; (b) detecting in the genome of a second soybean plant or in the genome of the second soybean germplasm at least one marker locus that is associated the Rbs3a BSR haplotype which is associated with resistance to Brown Stem Rot and selecting the second soybean plant or the second soybean germplasm having said marker locus; (c) crossing the selected first soybean plant or first soybean germplasm with the selected second soybean plant or the second soybean germplasm; and, (d) selecting progeny having in their genome the at least one marker locus that is associated with an improved resistance to FEY and the at least one marker locus that is associated with the Rbs3a BSR haplotype.

While any known marker associated with FEY resistance can be used in this method, in specific embodiment the FEY marker employed (A) can be interval flanked by and including the marker loci BARC-024115-04764 and BARC-040393-07727 on linkage group linkage Group J_(16); (B) can comprise one or more of S06363-1, S14236-1, S00005-01 and/or a marker closely linked thereto on linkage group J_(16); (C) can comprise a haplotype of marker loci on linkage group J_(16) comprising a T or C allele at S00005-01 and a G allele at S14236-1; (D) can comprise a haplotype of marker loci on linkage group J_(16) comprising a C allele at S06363-1 and a T or C allele at S00005-01; (E) can comprise a haplotype of marker loci on linkage group J_(16) comprising a C allele at S06363-1 and a G allele at S14236-1; and/or, (F) can comprise a haplotype of marker loci on linkage group J_(16) comprising a C allele at S06363-1, a G allele at S14236-1, and a T or a C allele at S00005-01. In one non-limiting example, the FEY marker employed is S00005-01a. In such methods, the BSR Rbs3a haplotype can be followed by using markers associated with the Rbs3a BSR haplotype which can comprise (a) a Rbs3a haplotype of marker loci on linkage group J_(16) comprising one or more of the following: a G allele at S01584-1, an A allele at S04831-1, a C allele at S16015-001, a T allele at S07157-1, a G allele at S07157-2, a T allele at S16023-001, and/or a C allele at S04857-1; (b) a Rbs3a haplotype of marker loci on linkage group J_(16) comprising an A allele at S04831-1 and a T allele at S07157-1; (c) a Rbs3a haplotype of marker loci on linkage group J_(16) comprising a G allele at S01584-1 and a T allele at S07157-1; (d) a Rbs3a haplotype of marker loci on linkage group J_(16) comprising a C allele at S16015-1 and an A allele at S04831-1; (e) a Rbs3a haplotype of marker loci on linkage group J_(16) comprising G allele at S01584-1 and a C allele at S16015-1; (f) a Rbs3a haplotype of marker loci on linkage group J_(16) comprising a C allele at S04857-1 and a T allele at S07157-1; (g) a Rbs3a haplotype of marker loci on linkage group J_(16) comprising a C allele at S04857-1 and a C allele at S16015-1; (h) a Rbs3a haplotype of marker loci on linkage group J_(16) comprising a G allele at S01584-1, an A allele at S04831-1, and a T allele at S07157-1; (i) a Rbs3a haplotype of marker loci on linkage group J_(16) comprising a G allele at S01584-1, an A allele at S04831-1, and a C allele at S16015-1; (j) a Rbs3a haplotype of marker loci on linkage group J_(16) comprising a G allele at S01584-1, a C allele at S04857-1, and a T allele at S07157-1; (k) a Rbs3a haplotype of marker loci on linkage group J_(16) comprising a G allele at S01584-1, a C allele at S04857-1, and a C allele at S16015-1; (l) a Rbs3a haplotype of marker loci on linkage group J_(16) comprising a G allele at S01584-1, an A allele at S04831-1, a T allele at S07157-1, and a C allele at S16015-1; a G allele at S07157-2 and a T allele at S16023-1; (m) a Rbs3a haplotype of marker loci on linkage group J_(16) comprising one or more of the following: a G allele at S01584-1, an A allele at S04831-1, a C allele at S16015-001, a T allele at S07157-1, a G allele at S07157-2, a T allele at S16023-001, and/or a C allele at S04857-1; or (n) any haplotype of marker combination set forth in Table 4.

In still other embodiments, the BSR tolerance can be followed using any marker combinations set forth in Table 4 including markers that (a) can be interval flanked by and including the marker loci BARC-042193-08207 and BARC-011625-00310 on linkage group linkage Group J_(16); (b) can comprise one or more of S01584-1, S04857-1, S04831-1, S16015-001, S07157-1, S07157-2, and/or S16023-001 and/or a marker closely linked thereto on linkage group J_(16); (c) can comprise a Rbs3b haplotype of marker loci on linkage group J_(16) comprising one or more of the following: a G allele at S01584-1, a G allele at S04831-1, a T allele at S16015-001, a C allele at S07157-1, an A allele at S07157-2, a C allele at S16023-001, and/or a C allele at S04857-1; (d) can comprise a Rbs3a hidden haplotype of marker loci on linkage group J_(16) comprising one or more of the following: a G allele at S01584-1, an A allele at S04831-1, a T allele at S16015-001, a C allele at S07157-1, a G allele at S07157-2, a T allele at S16023-001, and/or a C allele at S04857-1; (d) can comprise a Rbs3a hidden haplotype of marker loci on linkage group J_(16) comprising an allele A at S04831-1 and a C allele at S07157-1; (f) can comprise a Rbs3a hidden haplotype of marker loci on linkage group J_(16) comprising an A allele at S04831-1 and a T allele at S16015-1; (j) can comprise a Rbs3a hidden haplotype of marker loci on linkage group J_(16) comprising a G allele at S01584-1 and a C allele at S07157-1; (k) can comprise a Rbs3a hidden haplotype of marker loci on linkage group J_(16) comprising a G allele at S01584-1 and a T allele at S16015-1; (1) can comprise a Rbs3a hidden haplotype of marker loci on linkage group J_(16) comprising a C allele at S04857-1 and a C allele at S07157-1; (m) can comprise a Rbs3a hidden haplotype of marker loci on linkage group J_(16) comprising a C allele at S04857-1 and a T allele at S16015-1; (n) can comprise a Rbs3a hidden haplotype of marker loci on linkage group J_(16) comprising a G allele at S01584-1, an A allele at S04831-1, and a C allele at S07157-1; (o) can comprise a Rbs3a hidden haplotype of marker loci on linkage group J_(16) comprising a G allele at S01584-1, an A allele at S04831-1, and a T allele at S16015-1; (p) can comprise a Rbs3a hidden haplotype of marker loci on linkage group J_(16) comprising a G allele at S01584-1, a C allele at S04857-1 and a C allele at S07157-1; (q) can comprise a Rbs3a hidden haplotype of marker loci on linkage group J_(16) comprising a G allele at S01584-1, a C allele at S04857-1, and a T allele at S16015-1; (r) can comprise a Rbs3a hidden haplotype of marker loci on linkage group J_(16) comprising a G allele at S01584-1 and an A allele at S04831-1; (s) can comprise a Rbs3a hidden haplotype of marker loci on linkage group J_(16) comprising a G allele at S01584-1, an A allele at S04831-1, a C allele at S07157-1, a T allele at S16015-1, a G allele at S07157-2 and a T allele at S16023-1; (t) can comprise a Rbs3b hidden haplotype of marker loci on linkage group J_(16) comprising one or more of the following: a G allele at S01584-1, an A allele at S04831-1, a T allele at S16015-001, a C allele at S07157-1, a G allele at S07157-2, a T allele at S16023-001, and/or a C allele at S04857-1; (u) can comprise a Rbs3b hidden haplotype of marker loci on linkage group J_(16) comprising a G allele at S01584-1 and a C allele at S04857-1; (v) can comprise a Rbs3b hidden haplotype of marker loci on linkage group J_(16) comprising a G allele at S01584-1 and a G allele at S04831-1; (w) can comprise a Rbs3b hidden haplotype of marker loci on linkage group J_(16) comprising a G allele at S04831-1 and a C allele at S04857-1; (x) can comprise a Rbs3b hidden haplotype of marker loci on linkage group J_(16) comprising a G allele at S01584-1 and a G allele at S07157-2; (y) can comprise a Rbs3b hidden haplotype of marker loci on linkage group J_(16) comprising a G allele at S01584-1 and a T allele at S16023-1; (z) can comprise a Rbs3b hidden haplotype of marker loci on linkage group J_(16) comprising a G allele at S01584-1 and a G allele at S14236-1; (aa) can comprise a Rbs3b hidden haplotype of marker loci on linkage group J_(16) comprising a G allele at S01584-1, a G allele at S04831-1, a C allele at S07157-1, a T allele at S16015-1, a G allele at S07157-2, and a T allele S16023-1; or any other combination set forth in Table 4.

In one non-limiting embodiment, the (a) at least one marker locus that is associated with an improved resistance to FEY comprises a haplotype that is associated with said resistance to FEY and the haplotype comprises the following marker locus: a G allele at S14236-1 and a T or a C allele at S00005-01; and, (b) a haplotype that is associated with the Rbs3a BSR haplotype and shows an improved resistance to BSR said haplotype comprises the following marker locus: an A allele at S04831-1 and a T allele at S07157-1.

In one embodiment, the method involves amplifying a variant or fragment of one or more polynucleotides comprising SEQ ID NOS: 13, 14, 15, 16, 17, 18, 49, 50, 51, 52, 53, 54, 55, 56, 57, 58, 59, 60, 77, and/or 78 or variants or fragments thereof. In one embodiment, the primer or primer pair can comprise a variant or fragment of one or more polynucleotides comprising SEQ ID NOS: 13, 14, 15, 16, 17, 18, 49, 50, 51, 52, 53, 54, 55, 56, 57, 58, 59, 60, 77 and/or 78 or complements thereof. In specific embodiments, the primer or primer pair comprises a nucleic acid sequence comprising SEQ ID NOS: 1, 2, 3, 4, 5, 6, 25, 26, 27, 28, 29, 30, 31, 32, 33, 34, 35, 36, 73 or 74 or variants or fragments thereof.

In a specific embodiment, the primer pair comprises SEQ ID NOS: 1 and 2; SEQ ID NOS: 3 and 4; SEQ ID NOS: 5 and 6; SEQ ID NOS: 25 and 26; SEQ ID NOS: 27 and 28; SEQ ID NOS: 29 and 30; SEQ ID NOS: 31 and 32; SEQ ID NOS: 33 and 34; SEQ ID NOS: 35 and 36; or SEQ ID NOS: 73 and 74.

In another embodiment, the method further comprises providing one or more labeled nucleic acid probes suitable for detection of each marker locus being amplified. In such a method, the labeled nucleic acid probe can comprise a sequence comprising a variant or fragment of one or more of the genomic loci provided herein. In one embodiment, the labeled nucleic acid probe can comprise a sequence comprising a variant or fragment of one or more polynucleotides comprising SEQ ID NOS: 13, 14, 15, 16, 17, 18, 49, 50, 51, 52, 53, 54, 55, 56, 57, 58, 59, 60, 77 and/or 78. In specific embodiments, the labeled nucleic acid probe comprises a nucleic acid sequence comprising SEQ ID NOS: 7, 8, 9, 10, 11, 12, 37, 38, 39, 40, 41, 42, 43, 44, 45, 46, 47, 48 75 and/or 76 or variants or fragments thereof.

Non-limiting examples of primers, probes, genomic loci and amplicons that can be used in the methods and compositions provided herein are summarized in Tables 5, 6, 7, 8, 9, 10, 11, and 12.

TABLE 5

Non-Limiting Examples of Primer Sequences Related to Frogeye Leaf Spot resistance markers.

| Marker Name | Locus Name | Marker Type | RES | SUS | TaqMan Allele-FAM | TaqMan Allele-VIC | FwdPrimer-Name | SEQ ID NO | FwdPrimer-Sequence | RevPrimer-Name | SEQ ID NO | RevPrimer-Sequence |
|---|---|---|---|---|---|---|---|---|---|---|---|---|
| S00005-01-A | S00005-01 | Two SNPs | T, C | A, T | T, C | A, T | S00005-F1 | 1 | GAATGGGTGTGACCTTCCTG | S00005-R1 | 2 | CAGTTTGAAAAGGGTTCAGCA |
| S06363-1-Q1 | 606363-1 | SNP | C | T | C | T | S06363-F1 | 3 | AGTTGCTGCCGTCATTTGAT | S06363-R1 | 4 | AATGAGGATTTGGTCGTTGTG |
| S14236-1-Q3 | S14236-1 | SNP | G | A | G | A | S14236-F1 | 5 | CTCCGCTCAGGATCCTCTAAA | S14236-R1 | 6 | TCACTATTCTCTGATGTTGACACG |

TABLE 6

Non-Limiting Examples of Probe Sequences for FEY resistance markers.

| Marker Name | Locus Name | FAMProbe-Name | FAMProbe-Sequence | SEQ ID NO | VICProbe-Name | VICProbe-Sequence | SEQ ID NO |
|---|---|---|---|---|---|---|---|
| S00005-01-A | S00005-01 | S00005-01-PB1 | 6FAM-AGCTTGAGGATAGGATA | 7 | S00005-01-PB2 | VIC-AAGCTTGAAGATTGGATAT | 8 |
| S06363-1-Q1 | S06363-1 | S06363-1-P1 | 6FAM-actattCggttctggac | 9 | S06363-1-P2 | VIC-ccgactattTggttct | 10 |
| S14236-1-Q3 | S14236-1 | S14236-1-PB7 | 6FAM-atcatccGtttgaagaa | 11 | S14236-1-PB8 | VIC-atcatccAtttgaagaag | 12 |

TABLE 7

Non-Limiting Examples of Genomic Loci Comprising the Various FEY Marker Loci Provided Herein.

| Marker Name | SEQ ID NO (Res/Sus) | Genomic region |
|---|---|---|
| S00005-01-A | 13/14 | GATTTGGAGTAGAGAGCACAATTTGATAAGTTTTTCCTCCAAATATYGTCAATCTAGAAAGGGTAGAATTAGATATRCGGAGGACTTGTGCATCATCATGMAAAGAACAACCTATAAGCATCAAAGAATTTAAAACAASACAGTTTGAAAAGGGTTCAGCACAGTCATTGTCAGTTGCAGTAAATTTGAAATATCC[T/A]ATC[C/T]TCAAGCTTTTTAATGCAGGCAGGTTAAGAGATTTTGGAAGTATTATTTCAGGAAGGTCACACCCATTCCAAATCTCAAGATATGTCAAAGACTTAGAGRAAAAGATTAAAGGGATGGACTCAAAGTTGGGTCTAAAGCCTGAATATATACGCAATGTCAAGTGCTGGACATTRTGAAACACAGCATATTTAATGATCCTA |
| S06363-1-Q1 | 15/16 | ATCTAAAGTTCACAATTTTAAGGAATAATTAATTTTDAAGTCCTTGAATTTTTCTAAATTTTAAATTTCAGTTCCTAAATAAAGATTTAACTTGTAAAAGTGCTCAAAATTWTATTTAGTTACAACTTTTAGTTGCTGCCGTCATTTGATGATGANGTGGTGTCATGYGAAACAANATAAGATAATCAACCCCGACTATT[C/T]GGTTCTGGACCTCGGCTVTCAGTTGTCAAARCTTGGGTCAACCCTTYCACAACRACCAAATCCTCATTAAATTTATAATTTTAKAATTTATTTTTATTTTTACTGTYCACTATTCACCAAATAATGCACATGATAAAAAGTTATCAATGCATCMTTTGTAACTTTATGTTTGTGATRCTTTATTCTCCTTGTATTATACT |
| 514236-1-Q3 | 17/18 | CATGTCTAGAAAGATTAAATGTTGTTAGAGGAAATATATAATGGATGAATATAATTACACAGGGTAAGAAGTAAAATAAATTCAGGCACTCCGTTCACAAGAAGAAACAAACTTGTAAAAAATAGAATTAGGGCATCATCAGAGCATCTGGGCTCYGCTCAGGATCCTCTAAAGAAAAATGAGAAGCCATCCTATCATCC[A/G]TTTGAAGAAGTTGCCGTGTCAACATCAGAGAATAGTGAAGATGCTACACTYACTGCAGCAGAAACAAGTAGAACAATTATTGAGGTACTCAGTTGTATTAATTTTGCTARTCAATGATGTAATGTAACCTCACAGAACGAGGAAATTTTTTTTGGCAAACATTTAGGTTTTCTCATTTTAGTGCTATATTTTTACAACAG |

TABLE 8

Non-limiting Examples of Amplicons Comprising the Various FEY Marker Loci Provided Herein.

| Marker Name | SEQ ID NO (Res/Sus) | Amplicon Sequence |
|---|---|---|
| S00005-01-A | 19/20 | CAGTTTGAAAAGGGTTCAGCACAGTCATTGTCAGTTGCAGTAAATTTGAAATATCC[T/A]ATC[C/T]TCAAGCTTTTTAATGCAGGCAGGTTAAGAGATTTTGGAAGTATTATTTCAGGAAGGTCACACCCATTC |
| S06363-1-Q1 | 21/22 | AGTTGCTGCCGTCATTTGATGATGANGTGGTGTCATGYGAAACAANATAAGATAATCAACCCCGACTATT[C/T]GGTTCTGGACCTCGGCTVTCAGTTGTCAAARCTTGGGTCAACCCTTYCACAACRACCAAATCCTCATT |
| 514236-1-Q3 | 23/24 | CTCYGCTCAGGATCCTCTAAAGAAAAATGAGAAGCCATCCTATCATCC[A/G]TTTGAAGAAGTTGCCGTGTCAACATCAGAGAATAGTGA |

TABLE 9

Non-Limiting Examples of Primer Sequences Related to Brown Stem Rot resistance markers.

| Marker Name | Locus Name | Marker Type | RES | SUS | TaqMan Allele-FAM | TaqMan Allele-VIC | FwdPrimer-Name | SEQ ID NO | FwdPrimer-Sequence | RevPrimer-Name | SEQ ID NO | RevPrimer-Sequence |
|---|---|---|---|---|---|---|---|---|---|---|---|---|
| S01584-1-Q5 | S01584-1 | SNP | G | A | A | G | S01584-F3 | 25 | TCAACTTCAAACATGGCCTCT | S01584-R1 | 26 | gcctctccatttgcaacaat |
| S04831-1-Q2 | S04831-1 | SNP | A | G | A | G | S04831-F2 | 27 | GGAGAACGAGTAACACACAACAAG | S04831-R3 | 28 | AGGCACAAGGTGCTCAAGAC |
| S07157-1-Q1 | S07157-1 | SNP | A | C | T | C | S07157-F1 | 29 | TGAAGGCATTGCTCTCCTTT | S07157-R1 | 30 | CTGACCAAAGACCCTGTTGAC |
| S07157-2-Q1 | S07157-2 | SNP | A | C | A | G | S07157-F2 | 31 | TGAAGGCATTGCTCTCCTTT | S07157-R2 | 32 | CTGACCAAAGACCCTGTTGAC |
| S16015-001-Q001 | S16015-001 | SNP | C | T | T | C | S16015-F001 | 33 | TGGAATAGGTGGGTATGGTGA | S16015-R002 | 34 | GCCTACTCATGTAGTTGAAGATGACC |
| S16023-001-Q002 | S16023-001 | SNP | C | T | T | C | S16023-F002 | 35 | ATCTTGAATGCTGCTGTTCATC | S16023-R002 | 36 | GTTGGTTCATCTGAGTCTTATCCA |
| S04857-1-A | S0485T-1-A | SNP | C | A | | | PrimerFOR | 73 | ttcacttgcaaaacattgaaca | PrimerREV | 74 | aaggaatcctcccaccaaat |

TABLE 10

Non-Limiting Examples of Probe Sequences for BSR resistance markers.

| Marker Name | Locus Name | FAMProbe-Name | FamProbe-Sequence | SEQ ID NO | VICProbe-Name | VICProbe-Sequence | SEQ ID NO |
|---|---|---|---|---|---|---|---|
| S015841-Q5 | S01584-1 | S01584-1-PB1 | 6FAM-tcctcTaggtagacagc | 37 | S01584-1-PB2 | VIC-ttgttccctcCaggtaga | 38 |
| S04831-1-Q2 | S04831-1 | S04831-1-P1 | 6FAM-ctccattccTacttact | 39 | S04831-1-P2 | VIC-tccattccCacttact | 40 |
| S07157-1-Q1 | S07157-1 | S07157-1-P1 | 6FAM-TACACGCaTTACAGC | 41 | S07157-1-P2 | VIC-ctgtacacgcGttaca | 42 |
| S07157-2-Q1 | S07157-2 | S-7157-2-P1 | 6FAM-CTGTACAtGCGTTACA | 43 | S07157-2-P2 | VIC-ctgtacaCgcgttaca | 44 |
| S16015-001-Q001 | S16015-001 | S16015-001-X003 | 6FAM-ttaaacctAcatcctttg | 45 | S16015-001-X004 | VIC-ttaaacctGcatcctt | 46 |

TABLE 10-continued

Non-Limiting Examples of Probe Sequences for BSR resistance markers.

| Marker Name | Locus Name | FAMProbe-Name | FamProbe-Sequence | SEQ ID NO | VICProbe-Name | VICProbe-Sequence | SEQ ID NO |
|---|---|---|---|---|---|---|---|
| S16023-001-Q002 | S16023-001 | S16023-001-X005 | 6FAM-caatttactacaAtttcctc | 47 | S16023-001-X006 | VIC-caatttactacaGtttacct | 48 |
| S04857-1-A | S04857-1 | | acgatgttacatAccgga | 75 | | VIC-ttacatCccggaagc | 76 |

TABLE 11

Non-Limiting Examples of Genomic Loci Comprising the Various BSR Marker Loci Provided Herein.

| Marker Name | SEQ ID NO (Res/Sus) | Genomic region |
|---|---|---|
| S01584-1-Q5 | 49/50 | TATCAGCAAAATTATAWTGAGTAGTTATTTTCTGACAACATTTTATGCTCTGTTCCTGCTTTTATTTMATTCCTCAGGATTTAMTCTCGGATTAAATGGGTCACTTAAAAGTYCTDAGGCAAAGTGCAGAGAGAGGGAGAGACAAGCACTCCTCAACTTCAAACATGGCCTCTRAGATGACTCTGGCATGCTGTCTACCT[**A/G**]GAGGAACAATGACAATAATAGAGATTGTTGCAAATDGAGAGGCATTCAATGCAAYGATGAAACTGGTCACGTACAAGTACTCAATCTTCATTGTCCAGATAGACATTATTTGACAGGTGCAATNAATCTCACTTCRTTGATTCACTTGCAAAACATTGAACATCTGATCTCAGCAATAATGATTTTTTACGATGTTACNT |
| 504831-1-Q2 | 51/52 | TTTTGGATTTACTGCTTCAAAATGTTCACARTASATGTCGTCACCTTTACAAAGTAATTTTGGCCTGCAGTTTAATTGACTACAATATAGATATAAATATAAACATCTTCTTTATRTCAAATCTTAAATCTATCACTAATGTCCTAGGCACAAGGTGCTCAAGACAGATACAACTAATAGTTGCACCTTGTATAGTAAGT[**A/G**]GGAATGGAGCTGATCATTTTGCTGCTCTCGTTGRTCCTTTCCTCNTTAGTGTTAATGGTTCTCTTCTTGTTGTGTGTTACTCGTTCTCCTAAAGCAATGGAAGGCATCCCTGGCAGCCTTGGTTGGYCTATTGTGGGAGAGAGTTTCTCATTCCTCTCTGATTTTTCAAGTCCCTCYGGAATCTTTAGCTTCATGAACAA |
| 507157-1-Q1 | 53/54 | TCAGACAATGGACATCCAAGCAATGCAACATTGGTTGATCACAGAGTTTCATTTGAATTAACCGGGGAAGATGTTGCYCGGTGTCTTGCAAATAAAACTGGGGTATTGCTTCGAAACATGTCAGGGTCTTCACAAGGTATACTGACCAAAGACCCTGTTGACAGAGAAAGGGTGCAAATAGACACCAATAGTAGCTGTAA[**C/T**]GCRTGTACAGAGAAAACTGACGATAAGCCTGACAATCCTGTAGGAAAAGGAGAGCAATGCCTTCACAAGCAAAATTCTGTAAATTCTTCCAAAGAATTCAATTTTGACAACAGGAAAGGTGATGTTTCTGTTACTACTGGCAGTGGCTATGAGTGGTGGACTAACAGGAAGGTTGCTGGGAAGGAAGGTAGATCAGCCAA |
| 507157-2-Q1 | 55/56 | GACAATGGACATCCAAGCAATGCAACATTGGTTGATCACAGAGTTTCATTTGAATTAACCGGGGAAGATGTTGCYCGGTGTCTTGCAAATAAAACTGGGGTATTGCTTCGAAACATGTCAGGGTCTTCACAAGGTATACTGACCAAAGACCCTGTTGACAGAGAAAGGGTGCAAATAGACACCAATAGTAGCTGTAAYGC[**A/G**]TGTACAGAGAAAACTGACGATAAGCCTGACAATCCTGTAGGAAAAGGAGAGCAATGCCTTCACAAGCAAAATTCTGTAAATTCTTCCAAAGAATTCAATTTTGACAACAGGAAAGGTGATGTTTCTGTTACTACTGGCAGTGGCTATGAGTGGTGGACTAACAGGAAGGTTGCTGGGAAGGAAGGTAGATCAGCCAACAG |
| 516015-001-Q001 | 57/58 | AGACATTCTGATTGTTAACTCCCTCCASAATCTCATCTCCAAACACAACTTCTGAATCGATCAMCGAGTTTTTAATAGGCTAGGCAGCATCATTTGCAACTTGTGGTGGTGTTGATCACTTATGTCTATATAACAGCTTTGCCCTTCGGTAAGAAAGAGATAATAGAGTGGAATAGRTGGGTATGGTGAAGCAAAGGATG[**C/T**]AGGTTTAATAACAGGTACTAAGTCTTGGTGGTCATCTTCAACTACATGAGTAGGCAACAATTTGGTATTAGGCATATGGTGGGTCTTGATTCATACAGCAAGGAACAGGAAATTATACAAAATTCCGTTGATAATTGTTGATAGTACTCATTTGGAGAATGATTATAGAGATTTAAGTTAAAAAAATCTATAAAATAAAT |
| 516023-001-Q002 | 59/60 | ACAGCTGGGCTTTCTTCCCAATGTTACAGTCAGAAATGAATTGAGGTTTTAGTGTATTGCAACATGACTTAACCTGTATGGTATAAAAGCAAAAAGGATTTTCCATTTCTCTGCAGAACCTTTAGTATACTGAAATGTATATTTGAATATTTGAAGACCTTATCTTGAATGCTGCTGTTCATCATATACCTTTGAGGAAA[**C/T**]TGTAGTAAATTGATGATTGGATAAGACTCAGATGAACCAACAGTTGTTATATTCCTTGAGGACCTAAAGTAGAATGCAAGGGGAGCATAGTGGTAGTAGGTAGGGACCAATAGTGGGTTATATTATATTTATATAATTGTGAAACATTACTTCTTGCATTTCATCCTTTCAAATATACAGAAATAGCAAAGTACAGGTAT |
| S04857-1-A | 77/78 | ACATGGCCTCTRAGATGACTCTGGCATGCTGTCTACCTRGAGGAACAATGACAATAATAGAGATTGTTGCAAATGGAGAGGCATTCAATGCAAYGATGAAACTGGTCACGTACAAGTACTCAATCTTCATTGTCCAGATAGACATTATTTGACAGGTGCAATMAATCTCACTTCATTGATTCACTTGCAAAACATTGAACATCTGATCTCAGCAATAATGATTTTTTACGATGTTACAT[**C/A**]CCGGAAGCCATGGGCTCCTTCACCAACTTAAGATATCTCAATCTCTCRTATTCTGTATTTGGTGGGAGGATTCCTTCTAAACTTGGAAATCTTTCGCAACTACGATATCTAGAACTCGGGGGAAATCATCTTTGAGGAGCAATTCCTTTTCAGATGGGGAATCTCATG |

TABLE 12

Non-limiting Examples of Amplicons Comprising the Various BSR Marker Loci Provided Herein.

| Marker Name | SEQ ID NO (Res/Sus) | Amplicon Sequence |
|---|---|---|
| 501584-1-Q5 | 61/62 | TCAACTTCAAACATGGCCTCTRAGATGACTCTGGCATGCTGTCTACCT[A/G]GAGGAACAATGACAATAATAGAGATTGTTGCAAATDGAGAGGC |
| 504831-1-Q2 | 63/64 | AGGCACAAGGTGCTCAAGACAGATACAACTAATAGTTGCACCTTGTATAGTAAGT[A/G]GGAATGGAGCTGATCATTTTGCTGCTCTCGTTGRTCCTTTCCTCNTTAGTGTTAATGGTTCTCTTCTTGTTGTGTGTTACTCGTTCTCC |
| 507157-1-Q1 | 65/66 | CTGACCAAAGACCCTGTTGACAGAGAAAGGGTGCAAATAGACACCAATAGTAGCTGTAA[C/T]GCRTGTACAGAGAAAACTGACGATAAGCCTGACAATCCTGTAGGAAAAGGAGAGCAATGCCTTCA |
| 507157-2-Q1 | 67/68 | CTGACCAAAGACCCTGTTGACAGAGAAAGGGTGCAAATAGACACCAATAGTAGCTGTAAYGC[A/G]TGTACAGAGAAAACTGACGATAAGCCTGACAATCCTGTAGGAAAAGGAGAGCAATGCCTTCA |
| S16015-001-Q001 | 69/70 | TGGAATAGRTGGGTATGGTGAAGCAAAGGATG[C/T]AGGTTTAATAACAGGTACTAAGTCTTGGTGGTCATCTTCAACTACATGAGTAGGC |
| S16023-001-0002 | 71/72 | ATCTTGAATGCTGCTGTTCATCATATACCTTTGAGGAAA[C/T]TGTAGTAAATTGATGATTGGATAAGACTCAGATGAACCAAC |
| S04857-1 | 79/80 | TTCACTTGCAAAACATTGAACATCTGATCTCAGCAATAATGATTTTTTACGATGTTACAT[**C/A**]CCGGAAGCCATGGGCTCCTTCACCAACTTAAGATATCTCAATCTCTCRTATTCTGTATTTGGTGGGAGGATTCCTT |

In another embodiment, the method of detecting comprises DNA sequencing of at least one of the marker loci provided herein. As used herein, "sequencing" refers to sequencing methods for determining the order of nucleotides in a molecule of DNA. Any DNA sequencing method known in the art can be used in the methods provided herein. Non-limiting examples of DNA sequencing methods useful in the methods provided herein include Next Generation Sequencing (NGS) technologies, for example, as described in Egan, A. N, et al. (2012) *American Journal of Botany* 99(2):175-185; genotyping by sequencing (GBS) methods, for example, as described in Elshire, R. J., et al. (2011) *PLoS ONE* 6(5):e19379; Molecular Inversion Probe (MIP) genotyping, as described, for example, in Hardenbol, P., et al. (2003) *Nature Biotechnology* 21(6):673-678; or high throughput genotyping by whole-genome resequencing, as described, for example in Huang, X et al., (2009) *Genome Research* 19:1068-1076. Each of the above references is incorporated by reference in their entirety herein.

An active variant of any one of SEQ ID NOS: 1-78 can comprise a polynucleotide having at least 75%, 80% 85%, 90%, 91%, 92%, 93%, 94%, 95%, 96%, 97%, 98% or 99% sequence identity to SEQ ID NOS: 1-78 as long as it is capable of amplifying and/or detecting the marker locus of interest. By "fragment" is intended a portion of the polynucleotide. A fragment or portion can comprise at least 5, 6, 7, 8, 9, 10, 11, 12, 13, 14, 15, 16, 17, 18, 19, 20, 25, 30, 40, 50, 75, 100, 150, 200, 250, 300, 350, 400 contiguous nucleotides of SEQ ID NOS: 1-78 as long as it is capable of amplifying and/or detecting the marker locus of interest.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; or any equivalent program thereof. By "equivalent program" is intended any sequence comparison program that, for any two sequences in question, generates an alignment having identical nucleotide residue matches and an identical percent sequence identity when compared to the corresponding alignment generated by GAP Version 10.

The use of marker assisted selection (MAS) to select a soybean plant or germplasm which has a certain marker locus, haplotype or marker profile is provided. For instance, in certain examples a soybean plant or germplasm possessing a certain predetermined favorable marker locus or haplotype will be selected via MAS. In certain other examples, a soybean plant or germplasm possessing a certain predetermined favorable marker profile will be selected via MAS.

Using MAS, soybean plants or germplasm can be selected for markers or marker alleles that positively correlate with BSR resistance and/or FEY resistance, without actually raising soybean and measuring for resistance (or, contrawise, soybean plants can be selected against if they possess markers that negatively correlate with resistance). MAS is a powerful tool to select for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some embodiments, the molecular markers or marker loci are detected using a suitable amplification-based detection method. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage and Caruthers (1981) Tetrahedron Letts 22:1859-1862, e.g., using a commercially available automated synthesizer, e.g., as described in Needham-VanDevanter, et al. (1984) Nucleic Acids Res. 12:6159-6168. Oligonucleotides, including modified oligonucleotides, can also be ordered from a variety of commercial sources known to persons of skill in the art.

It will be appreciated that suitable primers and probes to be used can be designed using any suitable method. It is not intended that the invention be limited to any particular primer, primer pair or probe. For example, primers can be designed using any suitable software program, such as LASERGENE® or Primer3.

It is not intended that the primers be limited to generating an amplicon of any particular size. For example, the primers used to amplify the marker loci and alleles herein are not limited to amplifying the entire region of the relevant locus. In some embodiments, marker amplification produces an amplicon at least 20 nucleotides in length, or alternatively, at least 50 nucleotides in length, or alternatively, at least 100 nucleotides in length, or alternatively, at least 200 nucleotides in length.

Non-limiting examples of polynucleotide primers useful for detecting the marker loci provided herein are provided in Tables 5 and 9 and include, for example, SEQ ID NOS: 1-78 or variants or fragments thereof.

PCR, RT-PCR, and LCR are in particularly broad use as amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous journal and patent references, such as Mullis, et al. (1987) U.S. Pat. No. 4,683,202; Arnheim & Levinson (Oct. 1, 1990) C&EN 36-47; Kwoh, et al. (1989) Proc. Natl. Acad. Sci. USA 86:1173; Guatelli, et al., (1990) Proc. Natl. Acad. Sci. USA87:1874; Lomell, et al., (1989) J. Clin. Chem. 35:1826; Landegren, et al., (1988) Science 241:1077-1080; Van Brunt, (1990) Biotechnology 8:291-294; Wu and Wallace, (1989) Gene 4:560; Barringer, et al., (1990) Gene 89:117, and Sooknanan and Malek, (1995) Biotechnology 13:563-564.

Such nucleic acid amplification techniques can be applied to amplify and/or detect nucleic acids of interest, such as nucleic acids comprising marker loci. Amplification primers for amplifying useful marker loci and suitable probes to detect useful marker loci or to genotype SNP alleles are provided. For example, exemplary primers and probes are provided in SEQ ID NOS: 1-78 and in Tables 5, 6, 9 and 10, and the genomic loci comprising the various marker loci provided herein are provided in SEQ ID NOS: 13-18 and 49-60 and in Tables 7 and 11. Non-limiting examples of amplicon sequences comprising the marker loci provided herein are provided in Tables 8 and 12. However, one of skill will immediately recognize that other primer and probe sequences could also be used. For instance primers to either side of the given primers can be used in place of the given primers, so long as the primers can amplify a region that includes the allele to be detected, as can primers and probes directed to other SNP marker loci. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the compositions and methods are not limited to the primers and probes specifically recited herein.

In certain examples, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.).

Detectable labels may also include reporter-quencher pairs, such as are employed in Molecular Beacon and TaqMan™ probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent, depending on the embodiment. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules,* 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland, *Handbook of Fluorescent Probes and Research Chemicals*, Molecular Probes of Eugene, Oreg., 1992, the content of which is incorporated herein by reference.

In certain examples, reporter-quencher pairs are selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters are the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like. In certain other examples, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7,7'-tetrachlorofluorescein (6-TET™ available from Applied Biosystems), carboxy-X-rhodamine (ROX), 6-carboxy-4',5'-dichloro-2',7'-dimethoxyfluorescein (6-JOE™ available from Applied Biosystems), VIC™ dye products available from Molecular Probes, Inc., NED™ dye products available from Applied Biosystems, and the like. Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

In one aspect, real time PCR or LCR is performed on the amplification mixtures described herein, e.g., using molecular beacons or TaqMan™ probes. A molecular beacon (MB) is an oligonucleotide which, under appropriate hybridization conditions, self-hybridizes to form a stem and loop structure. The MB has a label and a quencher at the termini of the oligonucleotide; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone, et al., (1995) Molecular beacon probes combined with amplification by NASBA enable homogenous real-time detection of RNA, Nucleic Acids Res. 26:2150-2155; Tyagi and Kramer, (1996) Molecular beacons: probes that fluoresce upon hybridization, Nature Biotechnology 14:303-308; Blok and Kramer, (1997) Amplifiable hybridization probes containing a molecular switch, Mol Cell Probes 11:187-194; Hsuih. et al., (1997) Novel, ligation-dependent PCR assay for detection of hepatitis C in serum, J Clin Microbiol 34:501-507; Kostrikis, et al., (1998) Molecular beacons: spectral genotyping of human alleles, Science 279:1228-1229; Sokol, et al., (1998) Real time detection of DNA:RNA hybridization in living cells, Proc. Natl. Acad. Sci. U.S.A. 95:11538-11543; Tyagi, et al., (1998) Multicolor molecular beacons for allele discrimination, Nature Biotechnology 16:49-53; Bonnet, et al., (1999) Thermodynamic basis of the chemical specificity of structured DNA probes, Proc. Natl. Acad. Sci. U.S.A. 96:6171-6176; Fang, et al. (1999) Designing a novel molecular beacon for surface-immobilized DNA hybridization studies, J. Am. Chem. Soc. 121:2921-2922; Marras, et al., (1999) Multiplex detection of single-nucleotide variation using molecular beacons, Genet. Anal. Biomol. Eng. 14:151-156; and Vet, et al., (1999) Multiplex detection of four pathogenic retroviruses using molecular beacons, Proc. Natl. Acad. Sci. U.S.A. 96:6394-6399. Additional details regarding MB construction and use is found in the patent literature, e.g., U.S. Pat. Nos. 5,925,517; 6,150,097; and 6,037,130.

Another real-time detection method is the 5'-exonuclease detection method, also called the TaqMan™ assay, as set forth in U.S. Pat. Nos. 5,804,375; 5,538,848; 5,487,972; and 5,210,015, each of which is hereby incorporated by reference in its entirety. In the TaqMan™ assay, a modified probe, typically 10-25 nucleic acids in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are preferably attached to the probe within a few nucleotides of one another, usually within 30 nucleotides of one another, more preferably with a separation of from about 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook, et al., *Molecular Cloning—A Laboratory Manual* (3d ed.), Vol. 1-3, Cold Spring Harbor Laboratory, Cold Spring Harbor, N.Y., 2000 ("Sambrook"); *Current Protocols in Molecular Biology*, F. M. Ausubel, et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis, et al., eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

Other techniques for detecting SNPs can also be employed, such as allele specific hybridization (ASH). ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Real-time amplification assays, including MB or TaqMan™ based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain examples, each allele-specific probe for a certain SNP locus is 11-20 nucleotides in length, dual-labeled with a florescence quencher at the 3' end and either the 6-FAM (6-carboxyfluorescein) or VIC (4,7,2'-trichloro-7'-phenyl-6-carboxyfluorescein) fluorophore at the 5' end.

To effectuate SNP allele detection, a real-time PCR reaction can be performed using primers that amplify the region including the SNP locus, for instance the sequences listed in Table 5, the reaction being performed in the presence of all allele-specific probes for the given SNP locus. By then detecting signal for each detectable label employed and determining which detectable label(s) demonstrated an increased signal, a determination can be made of which allele-specific probe(s) bound to the amplicon and, thus, which SNP allele(s) the amplicon possessed. For instance, when 6-FAM- and VIC-labeled probes are employed, the distinct emission wavelengths of 6-FAM (518 nm) and VIC (554 nm) can be captured. A sample that is homozygous for one allele will have fluorescence from only the respective 6-FAM or VIC fluorophore, while a sample that is heterozygous at the analyzed locus will have both 6-FAM and VIC fluorescence.

The KASPar® and Illumina® Detection Systems are additional examples of commercially-available marker detection systems. KASPar® is a homogeneous fluorescent genotyping system which utilizes allele specific hybridization and a unique form of allele specific PCR (primer extension) in order to identify genetic markers (e.g. a particular SNP locus associated with BSR resistance and/or FEY resistance). Illumina® detection systems utilize similar technology in a fixed platform format. The fixed platform utilizes a physical plate that can be created with up to 384 markers. The Illumina® system is created with a single set of markers that cannot be changed and utilizes dyes to indicate marker detection.

These systems and methods represent a wide variety of available detection methods which can be utilized to detect markers associated with improved resistance to BSR and/or FEY, but any other suitable method could also be used.

Introgression of BSR resistance and/or FEY resistance into non-resistant or less-resistant soybean germplasm is provided. Any method for introgressing one or more marker loci into soybean plants known to one of skill in the art can be used. Typically, a first soybean germplasm that contains BSR resistance and/or FEY resistance derived from a particular marker locus, haplotype or marker profile and a second soybean germplasm that lacks such resistance derived from the marker locus, haplotype or marker profile are provided. The first soybean germplasm may be crossed with the second soybean germplasm to provide progeny soybean germplasm. These progeny germplasm are screened to determine the presence of BSR resistance and/or FEY resistance derived from the marker locus, haplotype or marker profile, and progeny that tests positive for the presence of resistance derived from the marker locus, haplotype or marker profile are selected as being soybean germplasm into which the marker locus, haplotype or marker profile has been introgressed. Methods for performing such screening are well known in the art and any suitable method can be used.

One application of MAS is to use the resistance markers, haplotypes or marker profiles to increase the efficiency of an introgression or backcrossing effort aimed at introducing a resistance trait into a desired (typically high yielding) background. In marker assisted backcrossing of specific markers from a donor source, e.g., to an elite genetic background, one selects among backcross progeny for the donor trait and then uses repeated backcrossing to the elite line to reconstitute as much of the elite background's genome as possible.

Thus, the markers and methods can be utilized to guide marker assisted selection or breeding of soybean varieties with the desired complement (set) of allelic forms of chromosome segments associated with superior agronomic performance (resistance, along with any other available markers for yield, disease resistance, etc.). Any of the disclosed marker loci, marker alleles, haplotypes, or marker profiles can be introduced into a soybean line via introgression, by traditional breeding (or introduced via transformation, or both) to yield a soybean plant with superior agronomic performance. The number of alleles associated with resistance that can be introduced or be present in a soybean plant ranges from 1 to the number of alleles disclosed herein, each integer of which is incorporated herein as if explicitly recited.

The markers and methods provided herein can also be utilized to guide marker assisted selection or breeding of soybean varieties comprising other BSR resistance and/or FEY resistance markers or alleles to create a molecular stack for BSR resistance and/or FEY resistance.

This also provides a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with resistance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant in that it comprises at least one of the marker loci or marker profiles, such that the progeny are capable of inheriting the marker locus or marker profile.

Often, a method is applied to at least one related soybean plant such as from progenitor or descendant lines in the subject soybean plants pedigree such that inheritance of the desired resistance can be traced. The number of generations separating the soybean plants being subject to the methods provided herein will generally be from 1 to 20, commonly 1 to 5, and typically 1, 2, or 3 generations of separation, and quite often a direct descendant or parent of the soybean plant will be subject to the method (i.e., 1 generation of separation).

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provides an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers, haplotypes, primers, probes, and marker profiles can be used for MAS in crosses involving elite×exotic soybean lines by subjecting the segregating progeny to MAS to maintain major yield alleles, along with the resistance marker alleles herein.

As an alternative to standard breeding methods of introducing traits of interest into soybean (e.g., introgression), transgenic approaches can also be used to create transgenic plants with the desired traits. In these methods, exogenous nucleic acids that encode a desired marker loci, marker profile or haplotype are introduced into target plants or germplasm. For example, a nucleic acid that codes for a resistance trait is cloned, e.g., via positional cloning, and introduced into a target plant or germplasm.

Experienced plant breeders can recognize resistant soybean plants in the field, and can select the resistant individuals or populations for breeding purposes or for propagation. In this context, the plant breeder recognizes "resistant" and "non-resistant" or "susceptible" soybean plants. However, plant resistance is a phenotypic spectrum consisting of extremes in resistance and susceptibility, as well as a continuum of intermediate resistance phenotypes. Evaluation of these intermediate phenotypes using reproducible assays are of value to scientists who seek to identify genetic loci that impart resistance, to conduct marker assisted selection for resistant populations, and to use introgression techniques to breed a resistance trait into an elite soybean line, for example.

By "improved resistance" is intended that the plants show a decrease in the disease symptoms that are the outcome of plant exposure to Brown Stem Rot and/or Frogeye Leaf Spot. That is, the damage caused by Brown Stem Rot and/or Frogeye Leaf Spot is prevented, or alternatively, the disease symptoms caused by Brown Stem Rot and/or Frogeye Leaf Spot is minimized or lessened. Thus, improved resistance to Brown Stem Rot and/or Frogeye Leaf Spot can result in reduction of the disease symptoms by at least about 2% to at least about 6%, at least about 5% to about 50%, at least about 10% to about 60%, at least about 30% to about 70%, at least about 40% to about 80%, or at least about 50% to about 90% or greater. Hence, the methods provided herein can be utilized to protect plants from Brown Stem Rot and/or Frogeye Leaf Spot.

Brown stem rot (BSR) of soybean (*Glycine max* (L.) Merrill) is caused by the fungal pathogen *Phialophora gregata*. Screening and selection of Brown Stem Rot resistant soybean plants may be performed, for example, by exposing plants to *Phialophora gregata* and selecting those plants showing resistance to Brown Stem Rot. Various assays can be used to measure resistance or improved resistance to BSR. For example, BSR resistance can be determined by visual observations after plant exposure to *Phialophora gregata*. Scores range from 1 to 9 and indicate visual observations of resistance as compared to other genotypes in the test. A score of 1 indicates *Phialophora gregata* is able to infect the plant and cause yield loss.

Non-limiting examples of BSR phenotypic screening are described in detail below. Phenotypic resistance or tolerance to brown stem rot can be evaluated in the field. The fields are selected based on a strong history of BSR infection. Generally, BSR severity increases as soil pH decreases. BSR severity is generally greatest at pH 6.0 and declines as the pH increases. It has been observed that cool temperatures during the pod filling stage can also be a major factor in BSR development. Yield trial sites are valuable sources of good BSR ratings as well. Susceptible and resistant varieties are grown as checks.

The plants are observed in mid-August for any stem browning or leaf chlorosis. BSR infection can be scored using stem and/or leaf tissues: (i) Split stem symptoms (BRS™) and/or (ii) leaf scorch symptoms (BSRLF).

The scoring system for the BSRLF trait is an estimate of affected leaf area based on a visual assessment of incidence-by-severity for the plot. A 1-9 scale is used based on total leaf area of plot affected:

9=no symptoms,
8=slight symptoms (a few chlorotic spots can be found),
7=about 15% affected leaf area,
6=30% affected leaf area,
5=about 40% total leaf area affected,
4=50% affected leaf area,
3=60% affected leaf area,
2=70% affected leaf area,
1=>80% affected leaf area).

Stems are periodically split to confirm if stem browning is present in plants showing leaf symptoms. As is known to those skilled in the art, there are two BSR pathogen types. Type A produces stem and leaf symptoms while Type B produces stem symptoms only. Split stems are scored based on the percent of brown nodes as follows:

9=clean
8=slight browning (1 or 2 nodes)
1=nearly the entire plant with brown nodes The pathology of the affected plants is evaluated to ensure that the symptoms are not being confused with sudden death syndrome.

The plots are scored approximately 2-3 times at 5-7 day intervals until the plot reached R7. R7 is a stage at the beginning of maturity, with seed in one or more pods that are physiologically mature.

Frogeye leaf spot is caused by *Cercospora sojina*. Screening and selection of Frogeye Leaf Spot resistant soybean plants may be performed, for example, by exposing plants to *Cercospora sojina* and selecting those plants showing resistance to developing Frogeye Leaf Spot. Various assays can be used to measure resistance or improved resistance to Frogeye Leaf Spot. For example, soybean Frogeye Leaf Spot resistance can be determined by visual observations after plant exposure to *Cercospora sojina*. Scores range from 1 to 9 and indicate visual observations of resistance as compared to other genotypes in the test. See, Table 15. A score of 1 indicates *Cercospora sojina* is able to infect the plant and cause yield loss. Frogeye leaf spot disease symptoms can be visually evaluated and scored from 1 to 9 comparing all genotypes in a given trial to known resistant and susceptible checks in the trial. The score is based upon the number and size of leaf lesions. A score of 1 indicates severe leaf necrosis lesions, whereas a score of 9 indicates no lesions. Disease symptoms can also appear on stem, pod, and seed.

In some examples, a kit or an automated system for detecting marker loci, haplotypes, and marker profiles, and/or correlating the marker loci, haplotypes, and marker profiles with a desired phenotype (e.g., resistance Frogeye Leaf Spot and/or Brown Stem Rot) are provided. As used herein, "kit" refers to a set of reagents for the purpose of performing the various methods of detecting or identifying herein, more particularly, the identification and/or the detection of a soybean plant or germplasm having improved resistance to Frogeye Leaf Spot and/or Brown Stem Rot.

In one embodiment, a kit for detecting or selecting at least one soybean plant or soybean germplasm with improved resistance to Frogeye Leaf Spot is provided. Such a kit comprises (a) primers or probes for detecting one or more marker loci associated with resistance to FEY, wherein at least one of the primers and probes in the kit are capable of detecting a marker locus, wherein the marker locus that: (A) can be interval flanked by and including the marker loci BARC-024115-04764 and BARC-040393-07727 on linkage group linkage Group J_(16); (B) can comprise one or more of S06363-1, S14236-1, S00005-01 and/or a marker closely linked thereto on linkage group J_(16); (C) can comprise a haplotype of marker loci on linkage group J_(16) comprising a T or C allele at S00005-01 and a G allele at S14236-1; (D) can comprise a haplotype of marker loci on linkage group J_(16) comprising a C allele at S06363-1 and a T or C allele at S00005-01; (E) can comprise a haplotype of marker loci on linkage group J_(16) comprising a C allele at S06363-1 and a G allele at S14236-1; and/or, (F) can comprise a haplotype of marker loci on linkage group J_(16) comprising a C allele at S06363-1, a G allele at S14236-1, and a T or a C allele at S00005-01; and, (b) instructions for using the primers or probes for detecting the one or more marker loci and correlating the detected marker loci with predicted resistance to FEY.

In another embodiment, a kit for detecting or selecting at least one soybean plant or soybean germplasm with improved resistance to Brown Stem Rot is provided. Such a kit comprises (a) primers or probes for detecting one or more marker loci associated with resistance to BSR, wherein at least one of the primers and probes in the kit are capable of detecting a marker locus, wherein the marker locus is: (a) can be interval flanked by and including the marker loci BARC-042193-08207 and BARC-011625-00310 on linkage group linkage Group J_(16); (b) can comprise one or more of S01584-1, S04857-1, S04831-1, S16015-001, S07157-1, S07157-2, and/or S16023-001 and/or a marker closely linked thereto on linkage group J_(16); (c) can comprise a Rbs3a haplotype of marker loci on linkage group J_(16) comprising one or more of the following: a G allele at S01584-1, an A allele at S04831-1, a C allele at S16015-001, a T allele at S07157-1, a G allele at S07157-2, a T allele at S16023-001, and/or a C allele at S04857-1; (d) can comprise a Rbs3a haplotype of marker loci on linkage group J_(16) comprising an A allele at S04831-1 and a T allele at S07157-1; (e) can comprise a Rbs3a haplotype of marker loci on linkage group J_(16) comprising a G allele at S01584-1 and a T allele at S07157-1; (f) can comprise a Rbs3a haplotype of marker loci on linkage group J_(16) comprising a C allele at S16015-1 and an A allele at S04831-1; (g) can comprise a Rbs3a haplotype of marker loci on linkage group J_(16) comprising G allele at S01584-1 and a C allele at S16015-1; (h) can comprise a Rbs3a haplotype of marker loci on linkage group J_(16) comprising a C allele at S04857-1 and a T allele at S07157-1; (i) can comprise a Rbs3a haplotype of marker loci on linkage group J_(16) comprising a C allele at S04857-1 and a C allele at S16015-1; (j) can comprise a Rbs3a haplotype of marker loci on linkage group J_(16) comprising a G allele at S01584-1, an A allele at S04831-1, and a T allele at S07157-1; (k) can comprise a Rbs3a haplotype of marker loci on linkage group J_(16) comprising a G allele at S01584-1, an A allele at S04831-1, and a C allele at S16015-1; (l) can comprise a Rbs3a haplotype of marker loci on linkage group J_(16) comprising a G allele at S01584-1, a C allele at S04857-1, and a T allele at S07157-1; (m) can comprise a Rbs3a haplotype of marker loci on linkage group J_(16) comprising a G allele at S01584-1, a C allele at S04857-1, and a C allele at S16015-1; (n) can comprise a Rbs3a haplotype of marker loci on linkage group J_(16) comprising a G allele at S01584-1, an A allele at S04831-1, a T allele at S07157-1, and a C allele at S16015-1; a G allele at S07157-2 and a T allele at S16023-1; (o) can comprise a Rbs3b haplotype of marker loci on linkage group J_(16) comprising one or more of the following: a G allele at S01584-1, a G allele at S04831-1, a T allele at S16015-001, a C allele at S07157-1, an A allele at S07157-2, a C allele at S16023-001, and/or a C allele at S04857-1; (p) can comprise a Rbs3a hidden haplotype of marker loci on linkage group J_(16) comprising one or more of the following: a G allele at S01584-1, an A allele at S04831-1, a T allele at S16015-001, a C allele at S07157-1, a G allele at S07157-2, a T allele at S16023-001, and/or a C allele at S04857-1; (q) can comprise a Rbs3a hidden haplotype of marker loci on linkage group J_(16) comprising an allele A at S04831-1 and a C allele at S07157-1; (r) can comprise a Rbs3a hidden haplotype of marker loci on linkage group J_(16) comprising an A allele at S04831-1 and a T allele at S16015-1; (s) can comprise a Rbs3a hidden haplotype of marker loci on linkage group J_(16) comprising a G allele at S01584-1 and a C allele at S07157-1; (t) can comprise a Rbs3a hidden haplotype of marker loci on linkage group J_(16) comprising a G allele at S01584-1 and a T allele at S16015-1; (u) can comprise a Rbs3a hidden haplotype of marker loci on linkage group J_(16) comprising a C allele at S04857-1 and a C allele at S07157-1; (v) can comprise a Rbs3a hidden haplotype of marker loci on linkage group J_(16) comprising a C allele at S04857-1 and a T allele at S16015-1; (w) can comprise a Rbs3a hidden haplotype of marker loci on linkage group J_(16) comprising a G allele at S01584-1, an A allele at S04831-1, and a C allele at S07157-1; (x) can comprise a Rbs3a hidden haplotype of marker loci on linkage group J_(16) comprising a G allele at S01584-1, an A allele at S04831-1, and a T allele at S16015-1; (y) can comprise a Rbs3a hidden haplotype of marker loci on linkage group J_(16) comprising a G allele at S01584-1, a C allele at S04857-1 and a C allele at S07157-1; (z) can comprise a Rbs3a hidden haplotype of marker loci on linkage group J_(16) comprising a G allele at S01584-1, a C allele at S04857-1, and a T allele at S16015-1; (aa) can comprise a Rbs3a hidden haplotype of marker loci on linkage group J_(16) comprising a G allele at S01584-1 and an A allele at S04831-1; (ab) can comprise a Rbs3a hidden haplotype of marker loci on linkage group J_(16) comprising a G allele at S01584-1, an A allele at S04831-1, a C allele at S07157-1, a T allele at S16015-1, a G allele at S07157-2 and a T allele at S16023-1; (ac) can comprise a Rbs3b hidden haplotype of marker loci on linkage group J_(16) comprising one or more of the following: a G allele at S01584-1, an A allele at S04831-1, a T allele at S16015-001, a C allele at S07157-1, a G allele at S07157-2, a T allele at S16023-001, and/or a C allele at S04857-1; (ad) can comprise a Rbs3b hidden haplotype of marker loci on linkage group J_(16) comprising a G allele at S01584-1 and a C allele at S04857-1; (ae) can comprise a Rbs3b hidden haplotype of marker loci on linkage group J_(16) comprising a G allele at S01584-1 and a G allele at S04831-1; (af) can comprise a Rbs3b hidden haplotype of marker loci on linkage group J_(16) comprising a G allele at S04831-1 and a C allele at S04857-1; (ag) can comprise a Rbs3b hidden haplotype of marker loci on linkage group J_(16) comprising a G allele at S01584-1 and a G allele at S07157-2; (ah) can comprise a Rbs3b hidden haplotype of marker loci on linkage group J_(16) comprising a G allele at S01584-1 and a T allele at S16023-1; (ai) can comprise a Rbs3b hidden haplotype of marker loci on linkage group J_(16) comprising a G allele at S01584-1 and a G allele at S14236-1; (aj) can comprise a Rbs3b hidden haplotype of marker loci on linkage group J_(16) comprising a G allele at S01584-1, a G allele at S04831-1, a C allele at S07157-1, a T allele at S16015-1, a G allele at S07157-2, and a T allele S16023-1; or any other combination set forth in Table 4; and (b) instructions for using the primers or probes for detecting the one or more marker loci and correlating the detected marker loci with predicted resistance to BSR.

In still another embodiment, a kit for detecting or selecting at least one soybean plant or soybean germplasm with improved resistance to Frogeye Leaf Spot and Brown Stem Rot is provided. Such a kit comprises (a) primers or probes for detecting one or more marker loci associated with resistance to BSR and (b) primers or probes for detecting one or more maker loci associate with FEY. In such kit, any marker loci or haplotype associate with BSR and any marker loci associated with FEY can be used including any combination of marker loci or haplotypes set forth in any one of Tables 5-12 or the marker loci shown in FIG. 3.

Thus, a typical kit or system can include a set of marker probes or primers configured to detect at least one favorable allele of one or more marker loci associated with resistance to Frogeye Leaf Spot and/or Brown Stem Rot, for instance a favorable marker locus, haplotype or marker profile. These probes or primers can be configured, for example, to detect the marker loci noted in the tables and examples herein, e.g., using any available allele detection format, such as solid or liquid phase array based detection, microfluidic-based sample detection, etc. The systems and kits can further include packaging materials for packaging the probes, primers, or instructions, controls such as control amplification reactions that include probes, primers or template nucleic acids for amplifications, molecular size markers, or the like.

A typical system can also include a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, scanning detectors, phototubes and photodiodes, microscope stations, galvo-scans, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector examples include light (e.g., fluorescence) detectors or radioactivity detectors. For example, detection of a light emission (e.g., a fluorescence emission) or other probe label is indicative of the presence or absence of a marker allele. Fluorescent detection is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele. The detector(s) optionally monitors one or a plurality of signals from an amplification reaction. For example, the detector can monitor optical signals which correspond to "real time" amplification assay results.

System or kit instructions that describe how to use the system or kit or that correlate the presence or absence of the favorable allele with the predicted resistance are also provided. For example, the instructions can include at least one look-up table that includes a correlation between the presence or absence of the favorable alleles, haplotypes, or marker profiles and the predicted resistance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical example, the system instructions include at least one look-up table that includes a correlation between the presence or absence of the favorable alleles and predicted resistance. The instructions also typically include instructions providing a user interface with the system, e.g., to permit a user to view results of a sample analysis and to input parameters into the system.

Isolated polynucleotides comprising the nucleic acid sequences of the primers and probes provided herein are also encompassed herein. In one embodiment, the isolated polynucleotide comprises a polynucleotide capable of detecting a marker locus of the soybean genome (A) interval flanked by and including the marker loci BARC-032663-09006 and Satt431 on linkage group linkage Group J_(16); (B) comprising one or more of S06363-1, S14236-1, S00005-01 and/or a marker closely linked thereto on linkage group J_(16); (C) interval flanked by and including the marker loci BARC-042193-08207 and BARC-011625-00310 on linkage group linkage Group J_(16); or (D) can comprise one or more of S01584-1, S04831-1, S16015-001, S07157-1, S07157-2, S04857-1 and/or S16023-001 and/or a marker closely linked thereto on linkage group J_(16).

In specific embodiments, the isolated polynucleotide comprises: (a) a polynucleotide comprising SEQ ID NOS: 1-78; (b) a polynucleotide having at least 80%, 85%, 90%, 91%, 92%, 93%, 94%, 95%, 96%, 97%, 98%, or 99% sequence identity to SEQ ID NOs: 1-78; or (c) a polynucleotide comprising at least 10 contiguous nucleotides of SEQ ID NOs: 1-78.

In certain embodiments, the isolated nucleic acids are capable of hybridizing under stringent conditions to nucleic acids of a soybean cultivar resistant to FEY and/or BSR, for instance to particular SNPs that comprise a marker locus, haplotype or marker profile.

As used herein, a substantially identical or complementary sequence is a polynucleotide that will specifically hybridize to the complement of the nucleic acid molecule to which it is being compared under high stringency conditions. A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Appropriate stringency conditions which promote DNA hybridization, for example, 6×sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at S5 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Non-limiting embodiments include:

1. A method of identifying a first soybean plant or a first soybean germplasm that displays improved resistance to Frogeye Leaf Spot, the method comprising detecting in the genome of said first soybean plant or in the genome of said first soybean germplasm at least one marker locus that is associated with the resistance, wherein the at least one marker locus comprises S06363-1, S00005-01, S14236-1 or a marker closely linked thereto on linkage group J_(16).

2. The method of embodiment 1 (a), wherein at least two marker loci are detected.

3. The method of embodiment 2, wherein the at least two marker loci comprise a haplotype that is associated with said resistance.

4. The method of embodiment 3, wherein said haplotype associated with said resistance to Frogeye Leaf Spot comprises:

(a) a T or C allele at S00005-01 and a G allele at S14236-1;

(b) a C allele at S06363-1 and a T or C allele at S00005-01;

(c) a C allele at S06363-1 and a G allele at S14236-1; and/or, (d) a C allele at S06363-1, a G allele at S14236-1, and a T or a C allele at S00005-01.

5. The method of any one of embodiments 1-4, wherein the germplasm is a soybean variety.

6. The method of any one of embodiments 1-5, wherein the method further comprises selecting the first soybean plant or first soybean germplasm or a progeny thereof having the at least one marker locus.

7. The method of embodiment 6, further comprising crossing the selected first soybean plant or first soybean germplasm with a second soybean plant or second soybean germplasm.

8. The method of embodiment 7, wherein the second soybean plant or second soybean germplasm comprises an exotic soybean strain or an elite soybean strain.

9. The method of any one of embodiments 1-8, wherein the detecting comprises amplifying at least one of said marker loci and detecting the resulting amplified marker amplicon.

10. The method of embodiment 9, wherein the amplifying comprises:

a) admixing an amplification primer or amplification primer pair for each marker locus being amplified with a nucleic acid isolated from the first soybean plant or the first soybean germplasm, wherein the primer or primer pair is complementary or partially complementary to a variant or fragment of the genomic locus comprising the marker locus, and is capable of initiating DNA polymerization by a DNA polymerase using the soybean nucleic acid as a template; and b) extending the primer or primer pair in a DNA polymerization reaction comprising a DNA polymerase and a template nucleic acid to generate at least one amplicon.

11. The method of embodiment 10, wherein said method comprises amplifying a variant or fragment of one or more polynucleotides comprising SEQ ID NOs: 13, 14, 15, 16, 17 and/or 18.

12. The method of embodiment 10, wherein said primer or primer pair comprises a variant or fragment of one or more polynucleotides comprising SEQ ID NOs: 13, 14, 15, 16, 17 and/or 18 or complements thereof.

13. The method of embodiment 12, wherein said primer or primer pair comprises a nucleic acid sequence comprising SEQ ID NOs: 1, 2, 3, 4, 5, and/or 6 or variants or fragments thereof.

14. The method of embodiment 13, wherein said primer pair comprises:

a) SEQ ID NOS: 1 and 2;

b) SEQ ID NOS: 3 and 4; and/or c) SEQ ID NOS: 5 and 6.

15. The method of embodiment 10, wherein the method further comprises providing one or more labeled nucleic acid probes suitable for detection of each marker locus being amplified.

16. The method of embodiment 15, wherein said labeled nucleic acid probe comprises a nucleic acid sequence comprising a variant or fragment of one or more polynucleotides comprising SEQ ID NOs: 13, 14, 15, 16, 17 and/or 18 or complements thereof.

17. The method of embodiment 16, wherein the labeled nucleic acid probe comprises a nucleic acid sequence comprising SEQ ID NOs: 7, 8, 9, 10, 11, and/or 12.

18. The method of any one of embodiments 1-8, wherein the detecting comprises DNA sequencing of at least one of said marker loci.

19. An isolated polynucleotide capable of detecting a marker locus of the soybean genome that is associated with improved resistance to Frogeye Leaf Spot comprising S14236-1, S06363-1, S00005-01 or a marker closely linked thereto.

20. The isolated polynucleotide of embodiment 19, wherein the polynucleotide comprises:

(a) a polynucleotide comprising SEQ ID NOs: 1, 2, 3, 4, 5, 6, 7, 8, 9, 10, 11, and/or 12;

(b) a polynucleotide having at least 90% sequence identity to the polynucleotides set forth in part (a); or (d) a polynucleotide comprising at least 10 contiguous nucleotides of the polynucleotides set forth in part (a).

21. A kit for detecting or selecting at least one soybean plant or soybean germplasm with improved resistance to Frogeye Leaf Spot, the kit comprising:

a) at least a first primer or a first probe for detecting one or more marker loci associated with resistance to Frogeye Leaf Spot, wherein the primer or probe are capable of detecting a marker locus comprising S06363-1, S00005-01, S14236-1 or a marker closely linked thereto on linkage group J_(16); and, b) instructions for using the primers or probes for detecting the one or more marker loci and correlating the detected marker loci with predicted resistance to Frogeye Leaf Spot.

22. The kit of embodiment 21, wherein the kit comprises the first and a second probe or the first and a second primer for detecting one or more marker loci associate with resistance to Frogeye Leaf Spot, wherein (a) the first probe or primer is capable of detecting a marker locus comprising a C allele at S06363-1 and the second the second probe or primer is capable of detecting a marker locus comprising a G allele at S14236-1; or, (b) the first probe or primer is capable of detecting a marker locus comprising a C allele at S06363-1 and the second the second probe or primer is capable of detecting a marker locus comprising an A or a C allele at S00005-01.

(a) the first probe or primer is capable of detecting a marker locus comprising a T or C allele at S00005-01 and the second the second probe or primer is capable of detecting a marker locus comprising a G allele at S14236-1, (b) the first probe or primer is capable of detecting a marker locus comprising a C allele at S06363-1 and the second the second probe or primer is capable of detecting a marker locus comprising a T or a C allele at S00005-01; and/or, (c) the first probe or primer is capable of detecting a marker locus; comprising a C allele at S06363-1 and the second the second probe or primer is capable of detecting a marker locus comprising a G allele at S14236-1.

23. The kit of embodiment 21, wherein the kit comprises the first, a second and a third probe or the first, a second, or a third primer for detecting one or more marker loci associate with resistance to Frogeye Leaf Spot, wherein (a) the first probe or primer is capable of detecting a marker locus comprising a C allele at S06363-1;

(b) the second probe or primer is capable of detecting a marker locus comprising a G allele at S14236-1; and, (c) the third probe or primer is capable of detecting a marker locus comprising and a T or a C allele at S00005-01.

24. A method of identifying a first soybean plant or a first soybean germplasm that displays improved resistance to Brown Stem Rot (BSR), the method comprising detecting in the genome of said first soybean plant or in the genome of said first soybean germplasm at least one marker locus that is associated with the resistance wherein the at least one marker locus comprises one or more of S01584-1, S04857-1, S04831-1, S16015-001, S07157-1, S07157-2, and/or S16023-001 and/or a marker closely linked thereto on linkage group J_(16).

25. The method of embodiment 24, wherein at least two marker loci are detected and comprise:

(a) a Rbs3a haplotype of marker loci on linkage group J_(16) comprising one or more of the following: a G allele at S01584-1, an A allele at S04831-1, a C allele at S16015-001, a T allele at S07157-1, a G allele at S07157-2, a T allele at S16023-001, and/or a C allele at S04857-1;

(b) a Rbs3a haplotype of marker loci on linkage group J_(16) comprising an A allele at S04831-1 and a T allele at S07157-1;

(c) a Rbs3a haplotype of marker loci on linkage group J_(16) comprising a G allele at S01584-1 and a T allele at S07157-1;

(d) a Rbs3a haplotype of marker loci on linkage group J_(16) comprising a C allele at S16015-1 and an A allele at S04831-1;

(e) a Rbs3a haplotype of marker loci on linkage group J_(16) comprising G allele at S01584-1 and a C allele at S16015-1;

(f) a Rbs3a haplotype of marker loci on linkage group J_(16) comprising a C allele at S04857-1 and a T allele at S07157-1;

(g) a Rbs3a haplotype of marker loci on linkage group J_(16) comprising a C allele at S04857-1 and a C allele at S16015-1;

(h) a Rbs3a haplotype of marker loci on linkage group J_(16) comprising a G allele at S01584-1, an A allele at S04831-1, and a T allele at S07157-1;

(i) a Rbs3a haplotype of marker loci on linkage group J_(16) comprising a G allele at S01584-1, an A allele at S04831-1, and a C allele at S16015-1;

(j) a Rbs3a haplotype of marker loci on linkage group J_(16) comprising a G allele at S01584-1, a C allele at S04857-1, and a T allele at S07157-1;

(k) a Rbs3a haplotype of marker loci on linkage group J_(16) comprising a G allele at S01584-1, a C allele at S04857-1, and a C allele at S16015-1; or, (l) a Rbs3a haplotype of marker loci on linkage group J_(16) comprising a G allele at S01584-1, an A allele at S04831-1, a T allele at S07157-1, and a C allele at S16015-1; a G allele at S07157-2 and a T allele at S16023-1.

26. The method of embodiment 24, wherein at least two marker loci are detected and comprise a Rbs3b haplotype of marker loci on linkage group J_(16) comprising one or more of the following: a G allele at S01584-1, a G allele at S04831-1, a T allele at S16015-001, a C allele at S07157-1, an A allele at S07157-2, a C allele at S16023-001, and/or a C allele at S04857-1.

27. The method of embodiment 24, wherein at least two marker loci are detected and comprise:

(a) a Rbs3a hidden haplotype of marker loci on linkage group J_(16) comprising one or more of the following: a G allele at S01584-1, an A allele at S04831-1, a T allele at S16015-001, a C allele at S07157-1, a G allele at S07157-2, a T allele at S16023-001, and/or a C allele at S04857-1;

(b) a Rbs3a hidden haplotype of marker loci on linkage group J_(16) comprising an allele A at S04831-1 and a C allele at S07157-1;

(c) a Rbs3a hidden haplotype of marker loci on linkage group J_(16) comprising an A allele at S04831-1 and a T allele at S16015-1;

(d) a Rbs3a hidden haplotype of marker loci on linkage group J_(16) comprising a G allele at S01584-1 and a C allele at S07157-1;

(e) a Rbs3a hidden haplotype of marker loci on linkage group J_(16) comprising a G allele at S01584-1 and a T allele at S16015-1;
(f) a Rbs3a hidden haplotype of marker loci on linkage group J_(16) comprising a C allele at S04857-1 and a C allele at S07157-1;
(g) a Rbs3a hidden haplotype of marker loci on linkage group J_(16) comprising a C allele at S04857-1 and a T allele at S16015-1;
(h) a Rbs3a hidden haplotype of marker loci on linkage group J_(16) comprising a G allele at S01584-1, an A allele at S04831-1, and a C allele at S07157-1;
(i) a Rbs3a hidden haplotype of marker loci on linkage group J_(16) comprising a G allele at S01584-1, an A allele at S04831-1, and a T allele at S16015-1;
(j) a Rbs3a hidden haplotype of marker loci on linkage group J_(16) comprising a G allele at S01584-1, a C allele at S04857-1 and a C allele at S07157-1;
(k) a Rbs3a hidden haplotype of marker loci on linkage group J_(16) comprising a G allele at S01584-1, a C allele at S04857-1, and a T allele at S16015-1;
(l) a Rbs3a hidden haplotype of marker loci on linkage group J_(16) comprising a G allele at S01584-1 and an A allele at S04831-1; or,
(m) a Rbs3a hidden haplotype of marker loci on linkage group J_(16) comprising a G allele at S01584-1, an A allele at S04831-1, a C allele at S07157-1, a T allele at S16015-1, a G allele at S07157-2 and a T allele at S16023-1.

28. The method of embodiment 24, wherein the at least two marker loci comprise a haplotype that is associated with said resistance to BSR and comprises
(a) a Rbs3b hidden haplotype of marker loci on linkage group J_(16) comprising one or more of the following: a G allele at S01584-1, an A allele at S04831-1, a T allele at S16015-001, a C allele at S07157-1, a G allele at S07157-2, a T allele at S16023-001, and/or a C allele at S04857-1;
(b) a Rbs3b hidden haplotype of marker loci on linkage group J_(16) comprising a G allele at S01584-1 and a C allele at S04857-1;
(c) a Rbs3b hidden haplotype of marker loci on linkage group J_(16) comprising a G allele at S01584-1 and a G allele at S04831-1;
(d) a Rbs3b hidden haplotype of marker loci on linkage group J_(16) comprising a G allele at S04831-1 and a C allele at S04857-1;
(e) a Rbs3b hidden haplotype of marker loci on linkage group J_(16) comprising a G allele at S01584-1 and a G allele at S07157-2;
(f) a Rbs3b hidden haplotype of marker loci on linkage group J_(16) comprising a G allele at S01584-1 and a T allele at S16023-1;
(g) a Rbs3b hidden haplotype of marker loci on linkage group J_(16) comprising a G allele at S01584-1 and a G allele at S14236-1; or,
(h) a Rbs3b hidden haplotype of marker loci on linkage group J_(16) comprising a G allele at S01584-1, a G allele at S04831-1, a C allele at S07157-1, a T allele at S16015-1, a G allele at S07157-2, and a T allele S16023-1.

29. The method of any one of embodiments 24-28, wherein the germplasm is a soybean variety.

30. The method of any one of embodiments 24-29, wherein the method further comprises selecting the first soybean plant or first soybean germplasm or a progeny thereof having said haplotype.

31. The method of embodiment 30, further comprising crossing the selected first soybean plant or first soybean germplasm with a second soybean plant or second soybean germplasm.

32. The method of embodiment 31, wherein the second soybean plant or second soybean germplasm comprises an exotic soybean strain or an elite soybean strain.

33. The method of any one of embodiments 24-28, wherein the detecting comprises amplifying said marker loci of said haplotype and detecting the resulting amplified marker amplicon.

34. The method of embodiment 33, wherein the amplifying comprises:
a) admixing an amplification primer or amplification primer pair for each marker locus being amplified with a nucleic acid isolated from the first soybean plant or the first soybean germplasm, wherein the primer or primer pair is complementary or partially complementary to a variant or fragment of the genomic locus comprising the marker locus, and is capable of initiating DNA polymerization by a DNA polymerase using the soybean nucleic acid as a template; and
b) extending the primer or primer pair in a DNA polymerization reaction comprising a DNA polymerase and a template nucleic acid to generate at least one amplicon.

35. The method of embodiment 33, wherein said method comprises amplifying a variant or fragment of one or more polynucleotides comprising SEQ ID NOs: 49, 50, 51, 52, 53, 54, 55, 56, 57, 58, 59, 60, 77 and/or 78.

36. The method of embodiment 33, wherein said primer or primer pair comprises a variant or fragment of one or more polynucleotides comprising SEQ ID NOs: 49, 50, 51, 52, 53, 54, 55, 56, 57, 58, 59, 60, 77 and/or 78.

37. The method of embodiment 36, wherein said primer or primer pair comprises a nucleic acid sequence comprising SEQ ID NOs: 25, 26, 27, 28, 29, 30, 31, 32, 33, 34, 35, 36, 73 and/or 74 or variants or fragments thereof.

38. The method of embodiment 37, wherein said primer pair comprises:
a) SEQ ID NOS: 25 and 26;
b) SEQ ID NOS: 27 and 28;
c) SEQ ID NOS: 29 and 30;
d) SEQ ID NOS: 31 and 32;
e) SEQ ID NOS: 33 and 34;
f) SEQ ID NOS: 35 and 36; or,
g) SEQ ID NOS: 73 and 74.

39. The method of embodiment 33, wherein the method further comprises providing one or more labeled nucleic acid probes suitable for detection of each marker locus being amplified.

40. The method of embodiment 39, wherein said labeled nucleic acid probe comprises a nucleic acid sequence comprising a variant or fragment of one or more polynucleotides comprising SEQ ID NOs: 49, 50, 51, 52, 53, 54, 55, 56, 57, 58, 59, 60, 77 and/or 78 or complements thereof.

41. The method of embodiment 40, wherein the labeled nucleic acid probe comprises a nucleic acid sequence comprising SEQ ID NOs: 37, 38, 39, 40, 41, 42, 43, 44, 45, 46, 47, 48, 75 and/or 76.

42. The method of any one of embodiments 24-28, wherein the detecting comprises DNA sequencing of at least one of said marker loci.

43. An isolated polynucleotide capable of detecting a marker locus of the soybean genome that is associated with improved resistance to Brown Stem Rot (BSR) comprising S01584-1, S04831-1, S16015-001, S04857-1, S07157-1, S07157-2, or S16023-001 or a marker closely linked thereto.

44. The isolated polynucleotide of embodiment 43, wherein the polynucleotide comprises:
(a) a polynucleotide comprising SEQ ID NOs: 25, 26, 27, 28, 29, 30, 31, 32, 33, 34, 35, 36, 37, 38, 39, 40, 41, 42, 43, 44, 45, 46, 47, 48, 75 and/or 76;
(b) a polynucleotide having at least 90% sequence identity to the polynucleotides set forth in part (a); or
(d) a polynucleotide comprising at least 10 contiguous nucleotides of the polynucleotides set forth in part (a).

45. A kit for detecting or selecting at least one soybean plant or soybean germplasm with improved resistance to Brown Stem Rot, the kit comprising:
a) a set of primers or a set of probes for detecting at least one marker locus comprising S01584-1, S04857-1, S04831-1, S16015-001, S07157-1, S07157-2, or S16023-001 or a marker closely linked thereto on linkage group J_(16); and,
b) instructions for using the set of primers or the set of probes for detecting the haplotype and correlating the detected marker loci with predicted resistance to Brown Stem Rot.

46. The kit of embodiment 45, wherein said kit comprises sets of primers or probes that can detect a Rbs3a haplotype of a marker loci on linkage group J_(16), wherein each primer pair or each probe in said kit can detect one of the marker locus comprising:
(a) a G allele at S01584-1, an A allele at S04831-1, a C allele at S16015-001, a T allele at S07157-1, a G allele at S07157-2, a T allele at S16023-001, and/or a C allele at S04857-1;
(b) an A allele at S04831-1 and a T allele at S07157-1;
(c) a G allele at S01584-1 and a T allele at S07157-1;
(d) a C allele at S16015-1 and an A allele at S04831-1;
(e) a G allele at S01584-1 and a C allele at S16015-1;
(f) a C allele at S04857-1 and a T allele at S07157-1;
(g) a C allele at S04857-1 and a C allele at S16015-1;
(h) a G allele at S01584-1, an A allele at S04831-1, and a T allele at S07157-1;
(i) a G allele at S01584-1, an A allele at S04831-1, and a C allele at S16015-1;
(j) a G allele at S01584-1, a C allele at S04857-1, and a T allele at S07157-1;
(k) a G allele at S01584-1, a C allele at S04857-1, and a C allele at S16015-1; or,
(l) a G allele at S01584-1, an A allele at S04831-1, a T allele at S07157-1, and a C allele at S16015-1; a G allele at S07157-2 and a T allele at S16023-1.

47. The kit of embodiment 45, wherein said kit comprises sets of primers or probes that can detect a Rbs3b haplotype of a marker loci on linkage group J_(16), wherein each primer pair or each probe in said kit can detect one of the marker locus comprising a G allele at S01584-1, a G allele at S04831-1, a T allele at S16015-001, a C allele at S07157-1, an A allele at S07157-2, a C allele at S16023-001, and/or a C allele at S04857-1.

48. The kit of embodiment 45, wherein said kit comprises sets of primers or probes that can detect a Rbs3a hidden haplotype of a marker loci on linkage group J_(16), wherein each primer pair or each probe in said kit can detect one of the marker locus comprising:
(a) a G allele at S01584-1, an A allele at S04831-1, a T allele at S16015-001, a C allele at S07157-1, a G allele at S07157-2, a T allele at S16023-001, and/or a C allele at S04857-1;
(b) an A allele at S04831-1 and a C allele at S07157-1;
(c) an A allele at S04831-1 and a T allele at S16015-1;
(d) a G allele at S01584-1 and a C allele at S07157-1;
(e) a G allele at S01584-1 and a T allele at S16015-1;
(f) a C allele at S04857-1 and a C allele at S07157-1;
(g) a C allele at S04857-1 and a T allele at S16015-1;
(h) a G allele at S01584-1, an A allele at S04831-1, and a C allele at S07157-1;
(i) a G allele at S01584-1, an A allele at S04831-1, and a T allele at S16015-1;
(j) a G allele at S01584-1, a C allele at S04857-1 and a C allele at S07157-1;
(k) a G allele at S01584-1, a C allele at S04857-1, and a T allele at S16015-1;
(l) a G allele at S01584-1 and an A allele at S04831-1; or,
(m) a G allele at S01584-1, an A allele at S04831-1, a C allele at S07157-1, a T allele at S16015-1, a G allele at S07157-2 and a T allele at S16023-1.

49. The kit of embodiment 45, wherein said kit comprises sets of primers or probes that can detect a Rbs3b hidden haplotype of a marker loci on linkage group J_(16), wherein each primer pair or each probe in said kit can detect one of the marker locus comprising:
(a) a G allele at S01584-1, an A allele at S04831-1, a T allele at S16015-001, a C allele at S07157-1, a G allele at S07157-2, a T allele at S16023-001, and/or a C allele at S04857-1;
(b) a G allele at S01584-1 and a C allele at S04857-1;
(c) a G allele at S01584-1 and a G allele at S04831-1;
(d) a G allele at S04831-1 and a C allele at S04857-1;
(e) a G allele at S01584-1 and a G allele at S07157-2;
(f) a G allele at S01584-1 and a T allele at S16023-1;
(g) a G allele at S01584-1 and a G allele at S14236-1; or,
(h) a G allele at S01584-1, a G allele at S04831-1, a C allele at S07157-1, a T allele at S16015-1, a G allele at S07157-2, and a T allele S16023-1.

50. A method of breeding a soybean plant or a soybean germplasm that displays improved resistance to Frogeye Leaf Spot and improved resistance to Brown Stem Rot (BSR) comprising:
(a) detecting in the genome of a first soybean plant or in the genome of said first soybean germplasm at least one marker locus that is associated with an improved resistance to Frogeye Leaf Spot and selecting said first soybean plant or said first soybean germplasm having said marker locus;
(b) detecting in the genome of a second soybean plant or in the genome of said second soybean germplasm at least one marker locus that is associated the Rbs3a BSR haplotype which is associated with resistance to Brown Stem Rot and selecting said second soybean plant or said second soybean germplasm having said marker locus;
(c) crossing the selected first soybean plant or first soybean germplasm with the selected second soybean plant or the second soybean germplasm; and,
(d) selecting progeny having in their genome the at least one marker locus that is associated with an improved resistance to Frogeye Leaf Spot and the at least one marker locus that is associated with the Rbs3a BSR haplotype.

51. The method of embodiment 50, wherein at least one marker locus that is associated with an improved resistance to Frogeye Leaf Spot comprises:
(a) S06363-1, S00005-01, S14236-lor a marker closely linked thereto;
(b) a haplotype that is associated with said resistance to Frogeye Leaf Spot and said haplotype comprises the following marker locus: a C allele at S06363-1 and an A or C allele at S00005-01;

(b) a haplotype that is associated with said resistance to Frogeye Leaf Spot and said haplotype comprises the following marker locus: a T or C allele at S00005-01 and a G allele at S14236-1; or, (c) a haplotype that is associated with said resistance to Frogeye Leaf Spot and said haplotype comprises the following marker locus: a C allele at S06363-1 and a T or C allele at S00005-01; or, (d) a haplotype that is associated with said resistance to Frogeye Leaf Spot and said haplotype comprises the following marker locus: a C allele at S06363-1 and a G allele at S14236-1; and/or, (e) a haplotype that is associated with said resistance to Frogeye Leaf Spot and said haplotype comprises the following marker locus: a C allele at S06363-1, a G allele at S14236-1, and a T or a C allele at S00005-01.

52. The method of embodiment 50, wherein at least one marker locus that is associated with the Rbs3a BSR haplotype and shows an improved resistance to BSR comprises:

(a) a Rbs3a haplotype of marker loci on linkage group J_(16) comprising one or more of the following: a G allele at S01584-1, an A allele at S04831-1, a C allele at S16015-001, a T allele at S07157-1, a G allele at S07157-2, a T allele at S16023-001, and/or a C allele at S04857-1;

(b) a Rbs3a haplotype of marker loci on linkage group J_(16) comprising an A allele at S04831-1 and a T allele at S07157-1;

(c) a Rbs3a haplotype of marker loci on linkage group J_(16) comprising a G allele at S01584-1 and a T allele at S07157-1;

(d) a Rbs3a haplotype of marker loci on linkage group J_(16) comprising a C allele at S16015-1 and an A allele at S04831-1;

(e) a Rbs3a haplotype of marker loci on linkage group J_(16) comprising G allele at S01584-1 and a C allele at S16015-1;

(f) a Rbs3a haplotype of marker loci on linkage group J_(16) comprising a C allele at S04857-1 and a T allele at S07157-1;

(g) a Rbs3a haplotype of marker loci on linkage group J_(16) comprising a C allele at S04857-1 and a C allele at S16015-1;

(h) a Rbs3a haplotype of marker loci on linkage group J_(16) comprising a G allele at S01584-1, an A allele at S04831-1, and a T allele at S07157-1;

(i) a Rbs3a haplotype of marker loci on linkage group J_(16) comprising a G allele at S01584-1, an A allele at S04831-1, and a C allele at S16015-1;

(j) a Rbs3a haplotype of marker loci on linkage group J_(16) comprising a G allele at S01584-1, a C allele at S04857-1, and a T allele at S07157-1;

(k) a Rbs3a haplotype of marker loci on linkage group J_(16) comprising a G allele at S01584-1, a C allele at S04857-1, and a C allele at S16015-1;

(l) a Rbs3a haplotype of marker loci on linkage group J_(16) comprising a G allele at S01584-1, an A allele at S04831-1, a T allele at S07157-1, and a C allele at S16015-1; a G allele at S07157-2 and a T allele at S16023-1;

(m) a Rbs3a haplotype of marker loci on linkage group J_(16) comprising one or more of the following: a G allele at S01584-1, an A allele at S04831-1, a C allele at S16015-001, a T allele at S07157-1, a G allele at S07157-2, a T allele at S16023-001, and/or a C allele at S04857-1; or (n) any haplotype of marker combination set forth in Table 4.

53. The method of embodiment 50, wherein (a) at least one marker locus that is associated with an improved resistance to Frogeye Leaf Spot comprises a haplotype that is associated with said resistance to Frogeye Leaf Spot and said haplotype comprises the following marker locus: a G allele at S14236-1 and a T or a C allele at S00005-01; and, (b) a haplotype that is associated with the Rbs3a BSR haplotype and shows an improved resistance to BSR said haplotype comprises the following marker locus: an A allele at S04831-1 and a T allele at S07157-1.

EXPERIMENTAL

The following examples are offered to illustrate, but not to limit the claimed invention. It is understood that the examples and embodiments described herein are for illustrative purposes only, and persons skilled in the art will recognize various reagents or parameters that can be altered without departing from the spirit of the invention or the scope of the appended claims.

Example 1: Marker Loci Associated with Frogeye Leaf Spot Resistance

Markers were developed to characterize, identify, and/or select resistant or susceptible alleles at the Rcs3 locus on linkage group J_(ch 16). Markers were screened against various known resistant and susceptible inbred lines.

Assays to marker loci S00005-01, S06363-1, and S14236-1 were developed to identify alleles at the Rcs3 locus that are associated with Frogeye Leaf Sport (FEY) resistance. Genotypic to phenotypic associations at these loci were validated within a panel of 23 FEY resistant and 26 FEY susceptible varieties, which included proprietary experimental lines and proprietary commercial lines (Table 13). The level of FEY resistance ranges from the most susceptible score of 1 to a fully resistant score of 9. Both growth chamber seedling screening and field screening across locations and years were used to characterize the lines reaction to Frogeye Leaf Spot. To ensure robust assay performance in a high throughput genotyping setting, marker assay optimization was completed by screening a variety of primer/probe combinations. The optimized assays S00005-01-A, S06363-1-Q1, and S14236-1-Q3 were selected; however, other assay variations can be used to detect the polymorphisms.

TABLE 13

Allele calls at S0005-01, S0636301, and S14236-1 in a panel of resistance and susceptible lines. Both growth chamber seedling screening and field screening across locations and years were used to characterize the lines reaction to Frogeye Leaf Spot.

| Variety | class | S06363-1-Q1 | S14236-1-Q1 | S00005-01 | FEY |
|---|---|---|---|---|---|
| V4 | Rcs3 | C | G | T, C | 8 |
| V5 | Rcs3 | C | G | T, C | 9 |
| V6 | Rcs3 | C | G | T, C | 8 |
| V7 | Rcs3 | C | G | T, C | 9 |
| V8 | Rcs3 | C | G | T, C | 9 |
| V9 | Rcs3 | C | G | T, C | 9 |
| V10 | Rcs3 | C | G | T, C | 9 |
| V11 | Rcs3 | C | G | T, C | 8 |
| V12 | Rcs3 | C | G | T, C | 8 |
| V13 | Rcs3 | C | G | T, C | 9 |
| V14 | Rcs3 | C | G | T, C | 8 |

TABLE 13-continued

Allele calls at S0005-01, S0636301, and S14236-1 in a panel of resistance and susceptible lines. Both growth chamber seedling screening and field screening across locations and years were used to characterize the lines reaction to Frogeye Leaf Spot.

| Variety | class | S06363-1-Q1 | S14236-1-Q1 | S00005-01 | FEY |
|---|---|---|---|---|---|
| V15 | Rcs3 | C | G | T, C | 8 |
| V16 | Rcs3 | C | G | T, C | 8 |
| V17 | Rcs3 | | G | T, C | 9 |
| V18 | Rcs3 | C | G | T, C | 9 |
| V19 | Rcs3 | C | G | T, C | 8 |
| V20 | Rcs3 | C | G | T, C | 9 |
| V21 | Rcs3 | C | G | T, C | 9 |
| V22 | Rcs3 | | G | T, C | 9 |
| V23 | Rcs3 | C | G | T, C | 9 |
| V24 | sus | T | A | A, T | 3 |
| V25 | sus | T | A | A, T | 4 |
| V26 | sus | T | A | A, T | 3 |
| V27 | sus | T | A | A, T | 3 |
| V28 | sus | T | A | A, T | 2 |
| V29 | sus | T | A | A, T | 2 |
| V30 | sus | T | A | A, T | 3 |
| V31 | sus | | A | A, T | 2 |
| V32 | sus | T | A | A, T | 4 |
| V33 | sus | T | A | A, T | 4 |
| V34 | sus | T | A | A, T | 4 |
| V35 | sus | T | A | A, T | 4 |
| V36 | sus | T | A | A, T | 3 |
| V37 | sus | T | A | A, T | 2 |
| V38 | sus | T | A | A, T | 2 |
| V39 | sus | T | A | A, T | 2 |
| V40 | sus | T | A | A, T | 4 |
| V41 | sus | T | A | A, T | 2 |
| V42 | sus | | A | A, T | 3 |
| V43 | sus | | | A, T | 2 |
| V44 | sus | T | A | A, T | 2 |
| V45 | sus | T | | A, T | 2 |
| V46 | sus | C | A | A, T | 2 |
| V47 | sus | C | A | A, T | 2 |
| V48 | sus | C | A | A, T | 3 |
| V49 | sus | C | A | | 2 |

TaqMan Assays were Performed Under the Following or Similar Conditions:

Genomic DNA was extracted for testing using a standard CTAB protocol and exemplary amplification conditions are described below in Table 14A and 14B

TABLE 14A

| Cycle settings: Taqman ™ assay | | |
|---|---|---|
| 94° C. | 2 min | 1 cycle |
| 94° C. | 30 sec | 40 cycles |
| 60° C. | 60 sec | |

TABLE 14B

| Amplification Mix (in microliters): | |
|---|---|
| H2O | 3.625 |
| hottub buffer | 0.5 |
| dNTP (2.5 mM each) | 0.375 |
| primer1 + primer2 (10 uM each) | 0.15 |
| primer3 + primer4 (10 uM each) | 0.15 |
| probe 1 (10 uM) | 0.05 |
| Probe 2 (10 uM) | 0.05 |
| hottub enzyme | 0.025 |
| Invitrogen rox dye (50X) | 0.075 |
| DNA | 0.05 |
| Total | 5.05 |

Example 2: FEY QTL Mapping and S06363-1

The association between marker S06363-1 and FEY resistance was additionally validated by genotyping a RIL mapping population segregating for the FEY resistance phenotype. One-hundred and eighty-four progeny derived from the cross between the resistant cultivar 93B66 and the susceptible cultivar XB29K04 were used in the analysis. Each progeny was genotyped with four markers on Lg J. Interval mapping and single marker regression analysis suggests a significant QTL on Lg J that is tightly associated with marker S06363-1.

Methods:

Linkage Analysis:

Map Manager QTX.b20 was used to construct the linkage map and perform QTL analysis. The initial Map Manager Parameters were set to:

1) Linkage Evaluation: Intercross
2) Search Criteria: $P=1e^{-5}$
3) Map Function: Kosambi
4) Cross Type: Line Cross QTL Analysis:

Single marker analysis was performed using an additive regression model. Interval mapping was performed using a constrained additive model. A permutation test was run 1000 times using the free model to establish the threshold for statistical significance (LOD ratio statistic—LRS) to determine putative QTL.

TABLE 15

Description of FEY Scores

| Scale 1-9 | Code | Interaction phenotype |
|---|---|---|
| 9 | HR | No symptoms (immune; e.g., Davis) |
| 8 | HR | Few pinpoint necrotic flecks (hypersensitive reaction) |
| 7 | R | A few small lesions; may or may not have flecks |
| 5-6 | MR | Small-to-medium sized lesions with chlorotic flecks (mesothetic); occasionally few large lesions |
| 4 | MS | Tiny, discrete lesions; no flecks (e.g., Kent) |
| 3 | S | Many medium-to-large sized lesions; typically coalesced at leaf edges |
| 1-2 | HS | leaflets laden with lesions; coalesced at the leaf edges and between veins |

TABLE 16

Results of QTL mapping at marker S06363-1

| Marker | Analysis | LRS | p value | Additive effect | Percent variation explained |
|---|---|---|---|---|---|
| S06363-1 | Single Marker Regression | 143.7 | 0.00000 | −1.61 | 56 |
| S06363-1 | Interval Mapping | 142.4 | | −1.61 | 55 |

Example 3: Marker Loci Associated with Brown Stem Rot Resistance

Markers were developed to characterize, identify, and/or select resistant or susceptible alleles at the Rbs3 locus on linkage group J_(ch 16). Markers were screened against various known resistant and susceptible parents.

Assays to marker loci S01584-1, S04831-1, S07157-1, S07157-2, S16015-001, and S16023-001, were developed to identify the brown stem rot (BSR) resistance alleles Rbs3a and Rbs3b. These marker assays were validated against a panel of 12 resistant and 22 susceptible varieties (Table 17). To ensure robust assay performance in a high throughput genotyping setting, marker assay optimization was completed by screening a variety of primer/probe combinations. The optimized assays S01584-1-Q5, S04831-1-Q2, S07157-1-Q1, S07157-2-Q1, S16015-001-Q001, and S16023-001-Q002 were selected; however, other assay versions can be used to detect the polymorphism.

TABLE 17

Allele calls at marker loci associated with BSR resistance in a panel of known resistant and susceptible lines.

| Variety | Pheno Class | Rbs3 Allele | BSR Score | S01584-1 | S04831-1 | S16015-001 | S07157-1 | S07157-2 | S16023-001 |
|---|---|---|---|---|---|---|---|---|---|
| V21 | RES | Rbs3b | 7 | G | G | T | C | A | C |
| V50 | RES | Rbs3b | 9 | G | G | T | C | A | C |
| V11 | RES | Rbs3b | 7 | G | G | T | C | A | C |
| V51 | RES | Rbs3b | 7 | G | G | T | C | A | C |
| V52 | RES | Rbs3b | 7 | G | G | T | C | A | C |
| V6 | RES | Rbs3b | 7 | G | G | T | C | A | C |
| V53 | RES | Rbs3a | 7 | G | A | C | T | G | T |
| V54 | RES | Rbs3a | 8 | G | A | C | T | G | T |
| V55 | RES | Rbs3a | 8 | G | A | C | T | G | T |
| V56 | RES | Rbs3a | 8 | G | A | . | T | G | T |
| V57 | RES | Rbs3a | 7 | G | A | C | T | G | T |
| V58 | RES | Rbs3a | 7 | G | A | C | T | G | T |
| V33 | sus | . | 5 | A | A | T | C | G | T |
| V59 | sus | . | 5 | A | A | T | C | G | T |
| V60 | sus | . | 5 | A | A | T | C | G | T |
| V61 | sus | . | 5 | A | A | T | C | G | T |
| V62 | sus | . | 5 | A | A | T | C | G | T |
| V63 | sus | . | 5 | A | A | T | C | G | T |
| V64 | sus | . | 4 | A | A | T | C | G | T |
| V65 | sus | . | 4 | A | A | T | C | G | T |
| V66 | sus | . | 4 | A | A | T | C | G | T |
| V67 | sus | . | 4 | A | A | T | C | G | T |
| V68 | sus | . | 3 | A | A | T | C | G | T |
| V69 | sus | . | 3 | A | A | T | C | G | T |
| V70 | sus | . | 2 | A | A | T | C | G | T |
| V71 | sus | . | 2 | A | A | T | C | G | T |
| V10 | sus | . | 5 | A | A | T | C | A | C |
| Ml 2 | sus | . | 5 | A | A | T | C | A | C |
| V73 | sus | . | 4 | A | A | T | C | A | C |
| V74 | sus | . | 3 | A | A | T | C | A | C |
| V75 | sus | . | 4 | A | A | T | C | G | T |
| V76 | sus | . | 5 | G | G | T | C | G | T |
| V77 | sus | . | 4 | G | G | C | T | G | T |
| V78 | Res | Rbs3b hidden | 7 | G | G | T | C | G | T |
| V79 | Res | Rbs3b hidden | 6 | G | G | T | C | G | T |
| V80 | Res | Rbs3b hidden | 6 | G | G | T | C | G | T |
| V81 | Res | Rbs3b hidden | 7 | G | G | T | C | G | T |
| V82 | Res | Rbs3b hidden | 6 | G | G | T | C | G | T |
| V83 | Res | Rbs3b hidden | 5 | G | G | T | C | G | T |
| V84 | Res | Rbs3b hidden | 5 | G | G | T | C | G | T |
| V85 | Res | Rbs3b hidden | 6 | G | G | T | C | G | T |
| V86 | Res | Rbs3b hidden | 5 | G | G | T | C | G | T |
| V87 | Res | Rbs3b hidden | 8 | G | G | T | C | G | T |
| V88 | Res | Rbs3b hidden | 5 | G | G | T | C | G | T |
| V89 | Res | Rbs3b hidden | 6 | G | G | T | C | G | T |
| V90 | Res | Rbs3b hidden | 8 | G | G | T | C | G | T |
| V91 | Res | Rbs3a hidden | 8 | G | A | T | C | G | T |
| V2 | Res | Rbs3a hidden | 9 | G | A | T | C | G | T |
| V92 | Res | Rbs3a hidden | 7 | G | A | T | C | G | T |
| V93 | Res | Rbs3a hidden | 9 | G | A | T | C | G | T |

TABLE 17-continued

Allele calls at marker loci associated with BSR resistance in a panel of known resistant and susceptible lines.

| Variety | Pheno Class | Rbs3 Allele | BSR Score | S01584-1 | S04831-1 | S16015-001 | S07157-1 | S07157-2 | S16023-001 |
|---|---|---|---|---|---|---|---|---|---|
| V94 | Res | Rbs3a hidden | 9 | G | A | T | C | G | T |
| V95 | Res | Rbs3a hidden | 7 | G | A | T | C | G | T |

*the BSR "Resistant" genotype denoted in Table 17 is similar to the Rbs3b phenotype but without the RES allele at the S07157-2 marker. This genotype predicts and average to above average resistance.

S07157-1 and S07157-2 are only three nucleotides apart and are not in linkage disequilibrium. The probes for assays, S07157-1-Q1 and S07157-2-Q1, are designed such they overlap SNPs S07157-1 and S07157-2. S07157-1 serves as a marker for the Rbs3a haplotype, and the S07157-1-Q1 assay probes "T/C" at S07157-1 and "G" at S07157-2. Conversely, S07157-2 serves as a marker for the Rbs3b allele, and the S07157-2-Q1 assay probes "C" at S07157-1 and "A/G" S07157-2. Thus, S07157-1-Q1 fails in samples with the Rbs3b haplotype and S07157-2-Q1 fails in samples with the Rbs3a haplotype (Table 18).

TABLE 18

Top: Summary of alleles at S07157-1 and S07157-2 in lines with Rbs3b, Rbs3a or susceptible (SUS) lines. Bottom: Summary of the marker assay output using S07157-1-Q1 and S07157-2-Q1 when genotyping the indicated genetic backgrounds (Rbs3b, Rbs3a, and SUS).

| | Rbs3b | Rbs3a | SUS |
|---|---|---|---|
| S07157-1 | C | T | C |
| S07157-2 | A | G | G |
| | **Rbs3b** | **Rbs3a** | **SUS** |
| S07157-1-Q1 | Fail | FAM | VIC |
| S07157-2-Q1 | FAM | Fail | VIC |

The SNPs S16015-001 and S16023-001 were found to be in close genomic proximity to and in high linkage disequilibrium with S07157-1 and S07157-2, and thus could serve as additional Rbs3 markers that are tightly associated with BSR resistance. The marker assays S16015-001-Q001 and S16023-001-Q002 were developed to query these SNPs. Allele "C" at S16015-001 is associated with the Rbs3a allele, while allele "C" at S16023-001 is associated with the Rbs3b allele.

Although S07157-1 and S16015-001 and S07157-2 and S16023-001 are robust for selection of Rbs3a and Rbs3b respectively, they are not in complete linkage disequilibrium with the Rbs3a and Rbs3b alleles. To ensure selection of these alleles in additional genetic backgrounds, assays to SNP loci S01584-1 and S04831-1 were developed. The haplotypes associated with Rbs3a and Rbs3b, and susceptible lines are shown in Table 19. In certain instances, S01584-1-Q5 and S04831-1-Q2 can be used independently to differentiate resistant and susceptible alleles at Rbs3a and Rbs3b.

TABLE 19

Rbs3b and Rbs3a and susceptible haplotypes using the BSR marker panel.

| | S01584-1 | S04831-1 | S16015-001 | S07157-1 | S07157-2 | S16023-001 |
|---|---|---|---|---|---|---|
| Rbs3b | G | G | T | C | A | C |
| Rbs3a | G | A | C | T | G | T |
| SUS | A | A | T | C | G | T |
| SUS | A | A | T | C | A | C |
| Hidden Rbs3a | G | A | T | C | G | T |
| Resistant | G | G | T | C | G | T |
| SUS | G | G | C | T | G | T |

Summary of selections of Brown Stem resistance and resistance via molecular markers:

- S01584-1 will indicate Brown stem rot resistance or resistance from several sources by selecting the G allele.
- Selections of S01584-1 works effectively in almost all cases except where S16015-001 is the C allele and S04831-1 is the G allele. This genotype (S01584-1=G, S16015-001=C, and S04831-1=G) would produce a susceptible phenotype.
- To better define the expected phenotype, one could run the S01584-1 and select those with G allele and then concurrently or simultaneously run the S04831-1, S16015-001 and S16023-001 to refine the expected phenotype and further discard those with the susceptible genotype.
- Lines with the Rbs3a genotype provide a high level of resistance.
- Lines with the "Hidden" Rbs3a genotype also provide a high level of resistance.
- Lines with the Rbs3b genotype or the Resistant genotype provide a moderate to high level of resistance.
- All other genotypes are typically susceptible or moderately susceptible.

Genomic DNA was extracted for testing using a standard CTAB protocol and exemplary amplification conditions are described below in Table 20A and B.

TABLE 20A

Cycle settings: Taqman ™ assay

| | | |
|---|---|---|
| 94° C. | 2 min | 1 cycle |
| 94° C. | 30 sec | 40 cycles |
| 60° C. | 60 sec | |

TABLE 20B

| Amplification Mix (in microliters): | |
|---|---|
| H2O | 3.625 |
| hottub buffer | 0.5 |
| dNTP (2.5 mM each) | 0.375 |
| primer1 + primer2 (10 uM each) | 0.15 |
| primer3 + primer4 (10 uM each) | 0.15 |
| probe 1 (10 uM) | 0.05 |
| Probe 2 (10 uM) | 0.05 |
| hottub enzyme | 0.025 |
| Invitrogen rox dye (50X) | 0.075 |
| DNA | 0.05 |
| Total | 5.05 |

Example 4: Recombination Breeding and Stacking Robust BSR Resistance with Robust Frogeye Leaf Spot Resistance The genetic haplotype we refer to as Rbs3a has a very high level of resistance to Brown Stem Rot. The genetic haplotype we refer to as "Rbs3b" has moderate levels of resistance to Brown Stem Rot. Rbs3b (Brown Stem Rot resistance) and Rcs3 (Frogeye Leaf Spot resistance) are linked in coupling on Lg J. Our molecular maps suggest these two genes are 3 cM apart Historically a BSR marker has been used in many breeding programs to select for Rbs3b BSR resistance, which would also bring along the linked Rcs3 gene. We have begun to employ a marker to directly characterize and select for Rcs3 (S00005-01). We have evidence through several cycles of breeding that recombination is rare between Rbs3b and Rcs3 markers, we have never found a line to carry Rbs3b and not be Frogeye Leaf Spot resistant in the field. Our estimates for recombination based on genetic maps would indicate that recombination could occur 3% of the time. The data presented below confirms that recombination is rare between these two genes, and likely occurs 3% or less of the time.

Two F3 populations were evaluated using MAS markers, including a marker for Rbs3a, Rbs3b, and Rcs3 (S00005-01a) The populations were crosses between one parent possessing Rbs3a (the other Brown Stem Rot resistance locus, allelic to Rbs3b) and another parent that possessed Rbs3b/Rcs3. This was done for two reasons:

1. Able to measure recombination rates between Rbs3b and Rcs3 markers
2. to acquire a line(s) that had Rbs3a and Rcs3 linked in coupling to create germplasm with Rbs3a and Rcs3.

Below are the results of the F3 population study.

1. F3 population
a. Punched 737 F3 plants
b. Found 4 plants that were homozygous Rbs3a and Rcs3
c. Found 11 plants that were heterozygous Rbs3a/Rbs3b and homozygous Rcs3
d. Found 10 plants that were homozygous Rbs3a and heterozygous Rcs3
2. F3 population
a. Punched 1105 F3 plants
b. Found 3 plants that were homozygous Rbs3a and Rcs3
c. Found 6 plants that were heterozygous Rbs3a/Rbs3b and homozygous Rcs3
d. Found 4 plants that were homozygous Rbs3a and heterozygous Rcs3

Confirmation of Recombinants:

We selected some of the recombination lines for additional testing. We retested them with additional MAS (8 single seed from each plant) to see if they were truly recombinations that were homozygous. We have lines from both populations confirmed across all 8 seeds to be homozygous Rbs3a and Rcs3 lines. Others lines and the parents were tested at the same time to compare and confirm genotypes.

Confirmation of Frogeye Leaf Spot Resistance

We wanted to confirm that the Rcs3 gene still provides resistance to FEY (Frogeye Leaf spot) in the recombinant lines. 21 plants from 3 of the recombinant plants were screened. Scores in Table 21 below show that the recombinant liens have high level of resistance like the known Rcs3 parent.

TABLE 21

| Variety | Pot1 | Pot2 | Pot3 | Pot1 | Pot2 | Pot3 | Pot4 | Pot5 | Pot6 |
|---|---|---|---|---|---|---|---|---|---|
| V96 | 999 | 988 | 998 | 999 | 999 | 999 | 999 | | |
| V97 | 999 | 999 | 999 | 99M | 7MM | 9MM | 8MM | | |
| V98 | 798 | 999 | 998 | 999 | 898 | 989 | 889 | | |
| V99 | 123 | 886 | 555 | 655 | 343 | 346 | 326 | | |
| V100 | 579 | 388 | 888 | 776 | 797 | 879 | 87M | | |
| V101 | 999 | 999 | 997 | 999 | 989 | 999 | 999 | | |
| V11 | 998 | 999 | 998 | 999 | 989 | 999 | 999 | | |
| V102 | 55M | 577 | 544 | 123 | 2MM | 2MM | 33M | 665 | 2MM |
| V103 | 333 | 322 | 112 | 2M5 | 111 | 13M | MMM | 123 | 113 |
| V104 | 467 | 455 | 323 | 122 | 113 | 234 | 265 | 442 | MMM |
| V105 | 999 | 999 | 999 | | | Not planted | | | |
| V106 | 334 | 475 | 324 | 133 | 334 | 44M | 265 | 442 | MMM |
| V107 | 447 | 457 | 457 | | | Not planted | | | |
| V108 | | | | 889 | 987 | 888 | 988 | 686 | 899 |
| V109 | | | | 334 | 223 | 333 | 2M5 | 244 | 245 |

We were not able to confirm the reaction to Brown Stem Rot thru field or laboratory observations. No data was available.

Example 5: Development of Recombinant BSR Isolines in Combination with Rcs3

Purpose of Trial:

To measure the agronomic and yield effects of stacking Rcs3 (FEY resistance) with the Rbs3a BSR haplotype. Rcs3 is already commonly linked in coupling with the Rbs3b BSR haplotype. In BSR screening results, we typically see the most robust and stable level of resistance to BSR come from the Rbs3a BSR haplotype. We have also observed that Rcs3 is the most affective FEY resistance gene identified to date.

Our BSR haplotype consists of two markers 8 cM apart, and the Rcs3 marker sits in between them, closest to S07157-2. We have used molecular markers to select for recombinant lines in this region and develop a set of isolines for further validation of the commercial value of these recombinants.

Material Development and Background for Single Recombinants:

1. (Rbs3b+Rcs3) was crossed to (Rbs3a), the population was selfed until F3 at which time we selected a recombinant plant from the population that had the S07157-1 marker of the Rbs3a haplotype and Rcs3 stacked in coupling.
2. (S07157-1 RES+Rcs3) was crossed to (Rbs3b+Rcs3) and that population was selfed until F3 generation, at which time we used markers to select heterozygous plants in this region on J.
3. Five R1 lines were selected that were agronomically acceptable and high yielding (not necessarily better than checks, but best of the sisters).
4. Via marker data two heterogeneous plants (segregating in the BSR region, all plants were fixed for Rcs3) were derived from within each of these F3:F5 R1 lines. Those reselected F3:F5:F6 plants were advanced to the field.
2. 92 F3:F5:F7 plants were leaf punched from each of the 10 entries (F3:F5:F6) for genotyping.
   4 heterozygous plants were selected from each entry
   17 homozygous Rbs3b+Rcs and 23 Rbs3a+Rcs3 (single recombinants) plants were selected from each population for yield and agronomic evaluation trials.

Experiments with Single Recombinants

1. Development of Isolines for Trials
   a. Seed of 1 heterozygous F3:F5:F7 plant from each of the 10 entries were planted.
   b. Sample 36 plants from each row during the summer were selected. Then 4 or 5 plants from within each row that were homozygous Rbs3b+Rcs3 or homozygous Rbs3a+Rcs3 (half recombinants) were selected.
   c. 3 rows were found that met the above criteria and 6 homozygous plants (3 with recombination and 3 without) from one of the rows and 8 homozygous plants (4 with recombination and 4 without) from both of the other two rows were selected. This should provide highly inbred isogenic lines to compare the recombination to the non-recombinant type isolines.
   d. These 22 plants were sent to (F3:F5:F8 NIL's) for seed increase and then placed in trials for yield, maturity, and disease evaluation. The trial will be planted at 7 locations with 2 reps per location.

Material Development and Background for Double Recombinants:

1. Three R1 lines that are homozygous for single recombination events were selected for agronomics and high yield trials.
2. These 3 lines were crossed to lines carrying Rbs3a. By making these crosses, additional recombination can be selected for and to get the haplotype for BSR on both sides of the Rcs3 locus so that it is similar to the original Rbs3a BSR haplotype. The intention is to find plants with resistant allele for the Rbs3a haplotype at both the S04831-1-marker and the S07157-1 markers and maintain the resistant allele for Rcs3 at S00005-01 and S14236-1.

Rbs3a+Rcs3 Stacking Work:

Single recombinant entries were crossed to a variety that carried the Rbs3a haplotype (S16015 and the flanking marker S04831). The population was selfed to the F3 generation.

Markers were applied to 2208 individuals and recombinant plants found that create the Rbs3a haplotype, but with the Rcs3 resistant marker call in the middle. Our hypothesis was that these plants would have high level BSR resistance like Rbs3a and high level FEY resistance like Rcs3.

The genotypic data for the double recombinants has been obtained. The number of recombinants we found in each population is summarized below in Table 22.

Two different recombination points can be identified in these populations. One involves a recombination between S04831-1 and S00134-1. The other recombination event involves a recombination between S00134-1 and S014236-1.

TABLE 22

| Total Number Plants Sampled | Number Homozygous Recombinants # | % Homozygous Recombinants | Number of Heterozygous Recombinants * | % Heterozygous Recombinants |
|---|---|---|---|---|
| 368 | 0 | 0.0% | 0 | 0.0% |
| 368 | 1 | 0.3% | 1 | 0.3% |
| 368 | 2 | 0.5% | 3 | 0.8% |
| 368 | 5 | 1.4% | 2 | 0.5% |
| 368 | 2 | 0.5% | 5 | 1.4% |
| 368 | 3 | 0.8% | 3 | 0.8% |
| 2208 | 13 | 0.6% | 14 | 0.6% |

plants that are homozygous resistant are both Rcs3 (S14236-1) and at S04831-1

* plants that are homozygous resistant for Rcs3 (S14236-1) and are heterozygous for S04831-1

Example 5

An F3:5 population from variety 1×variety 2, and an F3:5 population from variety 1×variety 3 segregating for brown stem rot response was used for Rbs# marker evaluation. Parental line variety 1 carries the Rbs# susceptible alleles, variety 2 and variety 3 are susceptible to Brown stem rot. These populations confirmed the association of S04857-1 on LG J_(16) with BSR resistance, wherein progeny having the favorable allele have a mean resistance score about 5 points higher than the segregating susceptible progeny within the population.

TABLE 23

| Population | Allele | Mean BSR score | # Progeny |
|---|---|---|---|
| Variety 1/Variety 2 | A_A | 1.9 | 23 |
| | C_C | 7.8 | 24 |
| Variety 3/Variety 1 | A_A | 3.5 | 31 |
| | C_C | 8.4 | 40 |

That which is claimed:

1. A method of breeding a soybean plant or a soybean germplasm that displays improved resistance to Frogeye Leaf Spot and improved resistance to Brown Stem Rot (BSR), the method comprising:

(a) detecting in the genome of a first soybean plant or in the genome of said first soybean germplasm at least one marker locus that is associated with an improved resistance to Frogeye Leaf Spot wherein the at least one marker locus that is associated with the improved resistance to Frogeye Leaf Spot comprises a G allele at S14236-1 and selecting said first soybean plant or said first soybean germplasm having said marker locus;

(b) detecting in the genome of a second soybean plant or in the genome of said second soybean germplasm at least one marker locus that is associated with a Rbs3a BSR haplotype which is associated with resistance to Brown Stem Rot wherein the at least one marker locus that is associated with the resistance to Brown Stem Rot comprises an A allele at S04831-1 and selecting said second soybean plant or said second soybean germplasm having said marker locus;

(c) crossing the selected first soybean plant or first soybean germplasm with the selected second soybean plant or the second soybean germplasm; and, (d) selecting progeny having in their genome the at least one marker locus that is associated with an improved resistance to Frogeye Leaf Spot and the at least one marker locus that is associated with the Rbs3a BSR haplotype.

2. The method of claim 1, wherein at least one marker locus that is associated with an improved resistance to Frogeye Leaf Spot comprises:

(a) S14236-1 or a marker closely linked thereto;

(b) a haplotype that is associated with said resistance to Frogeye Leaf Spot and said haplotype comprises the following marker locus: a T or C allele at S00005-01 and a G allele at S14236-1; or, (c) a haplotype that is associated with said resistance to Frogeye Leaf Spot and said haplotype comprises the following marker locus: a C allele at S06363-1 and a G allele at S14236-1; and/or, (d) a haplotype that is associated with said resistance to Frogeye Leaf Spot and said haplotype comprises the following marker locus: a C allele at S06363-1, a G allele at S14236-1, and a T or a C allele at S00005-01.

3. The method of claim 1, wherein at least one marker locus that is associated with the Rbs3a BSR haplotype and shows an improved resistance to BSR comprises:

(a) a Rbs3a haplotype of marker loci on linkage group J_(16) comprising an A allele at S04831-1;

(b) a Rbs3a haplotype of marker loci on linkage group J_(16) comprising an A allele at S04831-1 and a T allele at S07157-1;

(c) a Rbs3a haplotype of marker loci on linkage group J_(16) comprising a C allele at S16015-1 and an A allele at S04831-1;

(d) a Rbs3a haplotype of marker loci on linkage group J_(16) comprising a G allele at S01584-1, an A allele at S04831-1, and a T allele at S07157-1;

(e) a Rbs3a haplotype of marker loci on linkage group J_(16) comprising a G allele at S01584-1, an A allele at S04831-1, and a C allele at S16015-1;

(f) a Rbs3a haplotype of marker loci on linkage group J_(16) comprising a G allele at S01584-1, an A allele at S04831-1, a T allele at S07157-1, and a C allele at S16015-1; a G allele at S07157-2 and a T allele at S16023-1; or (g) a Rbs3a haplotype of marker loci on linkage group J_(16) comprising one or more of the following: a G allele at S01584-1, an A allele at S04831-1, a C allele at S16015-001, a T allele at S07157-1, a G allele at S07157-2, a T allele at S16023-001, and/or a C allele at S04857-1.

4. The method of claim 1, wherein (a) at least one marker locus that is associated with an improved resistance to Frogeye Leaf Spot comprises a haplotype that is associated with said resistance to Frogeye Leaf Spot and said haplotype further comprises the following marker locus: T or a C allele at S00005-01; and (b) a haplotype that is associated with the Rbs3a BSR haplotype and shows an improved resistance to BSR said haplotype comprises the following marker locus: a T allele at S07157-1.

* * * * *